(12) United States Patent
Walczak et al.

(10) Patent No.: US 10,696,709 B2
(45) Date of Patent: Jun. 30, 2020

(54) PHOSPHOTRIAZOLE MRNA 5'-END CAP ANALOGS, COMPOSITION COMPRISING THE SAME, RNA MOLECULE INCORPORATING THE SAME, USES THEREOF AND METHOD OF SYNTHESIZING RNA MOLECULE, PROTEIN OR PEPTIDE

(71) Applicant: UNIWERSYTET WARSZAWSKI, Warsaw (PL)

(72) Inventors: Sylwia Walczak, Opacz Kolonia (PL); Joanna Kowalska, Warsaw (PL); Jacek Jemielity, Warsaw (PL)

(73) Assignee: UNIWERSYTET WARSZAWSKI, Warsaw (PL)

( * ) Notice: Subject to any disclaimer, the term of this patent is extended or adjusted under 35 U.S.C. 154(b) by 0 days.

(21) Appl. No.: 16/318,126

(22) PCT Filed: Jul. 12, 2017

(86) PCT No.: PCT/IB2017/054221
§ 371 (c)(1),
(2) Date: Jan. 15, 2019

(87) PCT Pub. No.: WO2018/015845
PCT Pub. Date: Jan. 25, 2018

(65) Prior Publication Data
US 2020/0055891 A1    Feb. 20, 2020

(30) Foreign Application Priority Data
Jul. 16, 2016 (PL) .......................... 417980

(51) Int. Cl.
*C07H 19/207* (2006.01)
*C07H 21/02* (2006.01)
*C07H 21/04* (2006.01)
*C12P 19/34* (2006.01)
*C12P 21/00* (2006.01)

(52) U.S. Cl.
CPC .......... *C07H 19/207* (2013.01); *C07H 21/02* (2013.01); *C07H 21/04* (2013.01); *C12P 19/34* (2013.01); *C12P 21/00* (2013.01)

(58) Field of Classification Search
None
See application file for complete search history.

(56) References Cited

FOREIGN PATENT DOCUMENTS

WO    2013059475 A1    4/2013

OTHER PUBLICATIONS

Walczak et al. (2014) "Synthesis and properties of dinucleotide cap analogs containing a triazole ring within the oligophosphate bridge" Collection Symposium Series, vol. 14, pp. 289-290.

Walczak et al. (2017) "A novel route for preparing 5' cap mimics and capped RNAs: phosphate-modified cap analogues obtained via click chemistry" Chemical Science, vol. 8, No. 1, pp. 260-267.

Wanat et al. (2015) "Ethynyl, 2-Propynyl, and 3-Butynyl C-Phosphonate Analogues of Nucleoside Di- and Triphosphates: Synthesis and Reactivity in CuAAC", Organic Letters, vol. 17, No. 12, pp. 3062-3065.

*Primary Examiner* — Eric Olson
(74) *Attorney, Agent, or Firm* — ALGM LLP; Harry J. Guttman

(57) ABSTRACT

The object of the invention is a compound of formula (I), or a stereoisomer or salt thereof, wherein $R^1$ and $R^2$ are selected from the group consisting of N, N+—$CH_3$, $N^+$—$C_2H_5$, $N^+$—$C_3H_8$, $N^+$—$C_4H_5$, $N^+$—$CH_2C_6H_5$ wherein at least one of $R^1$, $R^2$ is not N. n and m are independently chosen from the group consisting of 0, 1 and 2; X is selected from the group consisting of O, NH, S, $CH_2$ k is 1 or 2 Y is either void or selected from the group of —$CH_2$—, —$CH_2CH_2$—, —$CH_2O$—, —$CH_2S$—, —$CH_2NH$—, —$CH_2CH_2O$—, —$CH_2CH_2NH$—, —$CH_2CH_2S$— $R^3$, $R^4$, $R^5$, $R^6$ are selected from the group consisting of H, OH, $OCH_3$, or $OCH_2CH_3$; wherein $R^3$ and $R^4$ may be the same or different; $R^5$ and $R^6$ may be the same or different; if either of $R^3$, $R^4$ is different than OH than $R^5$ and $R^6$ are both OH; if either of $R^5$, $R^6$ is different than OH than $R^3$ and $R^4$ are both OH. The object of the invention is also a composition comprising the compound of the invention, an RNA molecule incorporating the same, uses thereof and a method of synthesizing, in vitro or in vivo, the RNA molecule, as well as a method of synthesizing a protein or peptide in vitro, or in vivo or in cultured cells, said method comprising translating the RNA molecule.

9 Claims, 6 Drawing Sheets
Specification includes a Sequence Listing.

SEQUENCE LISTING

```
<160> NUMBER OF SEQ ID NOS: 7

<210> SEQ ID NO 1
<211> LENGTH: 57
<212> TYPE: DNA
<213> ORGANISM: Artificial Sequence
<220> FEATURE:
<223> OTHER INFORMATION: DNA template for  SEQ ID NO: 4 transcritpion;
      synthetic

<400> SEQUENCE: 1
atacgattta ggtgacacta tagaagaagc gggcatgcgg ccagccatag ccgatca         57

<210> SEQ ID NO 2
<211> LENGTH: 57
<212> TYPE: DNA
<213> ORGANISM: Artificial Sequence
<220> FEATURE:
<223> OTHER INFORMATION: DNA template for SEQ ID NO: 4 transcription;
      synthetic

<400> SEQUENCE: 2
tgatcggcta tggctggccg catgcccgct tcttctatag tgtcacctaa atcgtat         57

<210> SEQ ID NO 3
<211> LENGTH: 35
<212> TYPE: DNA
<213> ORGANISM: Artificial Sequence
<220> FEATURE:
<223> OTHER INFORMATION: DNazyme10-2312; synthetic
<400> SEQUENCE: 3
tgatcggcta ggctagctac aacgaggctg gccgc                                 35
```

```
<210> SEQ ID NO 4
<211> LENGTH: 35
<212> TYPE: RNA
<213> ORGANISM: Artificial Sequence
<220> FEATURE:
<223> OTHER INFORMATION: RNA substrate of DNA-catalyzed trimming;
      synthetic

<400> SEQUENCE: 4
gaagaagcgg gcaugcggcc agccauagcc gauca                              35

<210> SEQ ID NO 5
<211> LENGTH: 25
<212> TYPE: RNA
<213> ORGANISM: Artificial Sequence
<220> FEATURE:
<223> OTHER INFORMATION: RNA product of DNA-catalyzed trimming of SEQ ID
      NO: 4; synthetic

<400> SEQUENCE: 5
gaagaagcgg gcaugcggcc agcca                                         25

<210> SEQ ID NO 6
<211> LENGTH: 59
<212> TYPE: DNA
<213> ORGANISM: Artificial Sequence
<220> FEATURE:
<223> OTHER INFORMATION: DNA primer used for the synthesis of a template
      for luciferase mRNA transcription; synthetic

<400> SEQUENCE: 6
tttaggtgac actatagaag tactgttggt aaagccacca tggaagacgc caaaaacat    59

<210> SEQ ID NO 7
<211> LENGTH: 23
<212> TYPE: DNA
<213> ORGANISM: Artificial Sequence
<220> FEATURE:
<223> OTHER INFORMATION: DNA primer used for the synthesis of a template
      for luciferase mRNA transcription; synthetic

<400> SEQUENCE: 7
ttacaatttg gactttccgc cct                                           23
```

PHOSPHOTRIAZOLE MRNA 5'-END CAP ANALOGS, COMPOSITION COMPRISING THE SAME, RNA MOLECULE INCORPORATING THE SAME, USES THEREOF AND METHOD OF SYNTHESIZING RNA MOLECULE, PROTEIN OR PEPTIDE

TECHNICAL FIELD

This invention relates to novel phosphotriazole mRNA 5'-end cap analogs, a composition comprising the same, an RNA molecule incorporating the same, uses thereof and a method of synthesizing, in vitro or in vivo, the RNA molecule, as well as a method of synthesizing a protein or peptide in vitro, or in vivo or in cultured cells, said method comprising translating the RNA molecule.

STATE OF THE ART

The 7-methylguanosine ($m^7G$) cap present at the 5' end of eukaryotic mRNAs plays a crucial role in numerous fundamental cellular processes, mainly by protecting mRNA from premature cleavage and serving as a molecular platform for proteins acting in mRNA transport and translation.[1] Thus, chemical modifications of the 5' cap pave the way to design of molecular tools for selective modulation of cap-dependent processes and, consequently, mRNA metabolism.[2] The presence of the 5' cap is necessary for mRNA surveillance and efficient translation under normal conditions. Chemically synthesized mRNA cap analogs of $m^7GpppG$ type are utilized as reagents for in vitro synthesis of capped mRNAs.[3]

In vitro transcribed (IVT) 5'-capped mRNAs are useful tools for studying mRNA translation, transport, and turnover, and are an emerging class of highly promising therapeutic molecules. IVT mRNAs find application in protein expression in eukaryotic cell, extracts, cultured cells, or even whole organisms. Finally, IVT mRNAs have recently gained great attention as a tool for safe exogenous protein delivery for the purpose of anti-cancer vaccinations and gene-replacement therapies.[4]

The synthesis of 5'-capped mRNAs by using mRNA cap analogs can be achieved by in vitro transcription.[3] By this method, called co-transcriptional capping, the synthesis of RNA is performed by RNA polymerase on DNA template in the presence of all 4 NTPs and a cap dinucleotide, such as $m^7GpppG$. The DNA template is designed to incorporate G as the first transcribed nucleotide. The polymerase initiates the transcription from GTP or $m^7GpppG$, thereby incorporating one of the nucleotides at the 5' end of the nascent RNA. To increase the percentage of cap analogue incorporation (capping efficiency), the GTP concentration is decreased relative to the other NTPs, and the concentration of the cap dinucleotide is elevated (from 4- to 10-fold excess relative to GTP). Unfortunately, reverse incorporation of cap dinucleotides can potentially occur, resulting in a fraction of 'Gpppm$^7$G-capped' RNAs, which are translationally inactive. This problem has been solved by the discovery of 'anti-reverse cap analogs' (ARCAs) that are modified at the 2'- or 3'-positions of 7-methylguanosine (usually by replacing one of OH groups by $OCH_3$) to block reverse incorporation[5, 6]

It has been shown that co-transcriptional capping method enables incorporation at the RNA 5' end of various modified cap structures. These modified cap structures may carry molecular labels or confer new properties to mRNA such as increased translation efficiency and stability. Especially beneficial cap analogs are among those modified in the triphosphate bridge.[7] It has been shown that even single atom substitutions in the 5',5'-triphosphate bridge can affect the properties of mRNAs significantly. For example, a single atom substitution at the β-position of the oligophosphate bridge of the cap, introduced by the so-called β-S-ARCA, led to significant increase in translation efficiency of mRNA in vitro and in vivo,[8, 9] whereas a single O to $CH_2$ substitution at the α-β position led to decrease in translation efficiency.[10] The dramatically different biological effects of different single-atom substitutions within the cap indicates on high sensitivity of the translational machinery to oligophosphate chain modification and suggests this is a field for further exploration.

However, the development of novel cap analogues, either as research tools or compounds with medicinal potential, is limited by difficulties associated with the chemical synthesis of these compounds. The synthesis and purification of mono- and dinucleotide cap analogues are challenging due to their highly ionic nature and chemical lability of 7-methylguanosine.[11, 12] The usual synthetic approach, based on phosphorimidazolide chemistry and divalent-cation-excess-mediated pyrophosphate bond formation in organic solvent,[7, 13, 14] is both time-consuming and labour-intensive, challenging in upscaling, requires multiple purification steps, and occasionally results in complex mixtures of products and side-products that are difficult to separate. Occasionally, as in the case of β-S-ARCA,[15] this approach requires also generation of unstable mononucleotide intermediates, which are prone to spontaneous degradation upon storage. Hence, the typical synthetic approach is usually effective for production of cap analogs at low milligram scale, but is rather low throughput and very difficult scale-up. The ability to produce cap analogs in high purity and yield by an easily-scalable synthetic method would be critical for many applications, including in vivo and medicinal applications that require delivery of in vitro synthesized capped mRNAs into animals or humans.

"Click chemistry" is a term that describes a group of chemical reactions that are efficient, have a wide scope, are simple to perform and easy to scale-up, create products in a regio- and stereospecific manner with almost no side-products, and can be carried out in benign solvents such as water. Copper catalyzed azide-alkyne cycloaddition leading to formation of substituted 1,2,3-triazoles is a prime example of such reaction. CuAAC has been widely applied in functionalization of RNA and RNA components,[16, 17] including 5' end labeling,[18-22] bioconjugation,[23-26] and chemical ligation.[27] It has been found that the triazole moiety can replace one or more 5',3'-phosphodiester bonds in DNA[28, 29] and RNA[36-33] to generate functional mimics. Piecyk et al.[34] reported functionalization of mononucleotide cap analogs by CuAAC click chemistry to obtain analogs containing 1,2,3-triazole moiety at the N2-position of nucleobase, whereas Walczak et al.[45] reported cap analogs containing a 1,2,3-triazole moiety at the 5' position of the nucleoside moiety. However, such modification has never been investigated as an internal modification of the 5',5'-oligophosphate chain within the cap nor any other biologically active dinucleoside 5',5'-oligophoosphate.

DESCRIPTION OF THE INVENTION

The inventors obtained a novel class of dinucleotide cap analogues that can be provided by a simpler and more efficient synthetic approach, based on click chemistry.[35] The inventors employed copper(I)-catalyzed azide-alkyne cycloaddition (CuAAC) in aqueous medium to combine two 5'-mononucleotide subunits into one 5',5'-dinucleotide cap analog containing substituted 1,2,3-triazole as an internal modification of the oligophosphate chain. The analogs vary in the oligophosphate chain length, positioning of the triazole moiety within the oligophosphate chain, and type of spacers linking phosphate groups to the triazole moiety. Optionally, the new analogs have also a 2-O or 3'-O-alkyl group within 7-methylguanosine preferably a methyl group, producing analogs called anti-reverse cap analogs (ARCA). All new analogs were synthesized in aqueous medium under standard CuAAC catalytic conditions (CuSO$_4$, sodium ascorbate) from two chemically stable mononucleotide intermediates, in high yield, with formation of very little to no side-products. Several of the phosphotriazole analogues have high affinity for eukaryotic translation initiation factor 4E (eIF4E). mRNAs terminated with the new cap analogues can be obtained by standard in vitro transcription reaction. The efficiencies of cap incorporation into short RNA transcripts (% of capping) are comparable or slightly lower to those of unmodified caps. The short transcripts containing novel analogs are susceptible to decapping by Dcp2 decapping enzyme in vitro, thereby behaving like RNAs capped with unmodified cap structures. Surprisingly, luciferase-encoding mRNAs capped with some of the new phosphotriazole cap analogues had translational properties comparable to RNAs carrying standard 5' caps, despite the presence of the bulky triazole group. This is in contrast to previously reported cap analogs containing less bulky bridging modifications of oligophosphate e.g. (O to NH or O to CH$_2$ substitutions)[10, 36, 37] or analogs containing a 1,2,3-triazole moiety at the 5' position of the nucleoside moiety.[45]), which all have promoted translation less efficiently than standard cap analogs. Hence, the unexpected and unique property of phosphotriazole cap analogs is that they are good functional mimics of the natural cap. As such, phosphotriazole cap analogs are a viable alternative to the standard cap analogs that are obtained by more laborious chemical synthesis.

Therefore, the object of the invention is a compound of formula (I):

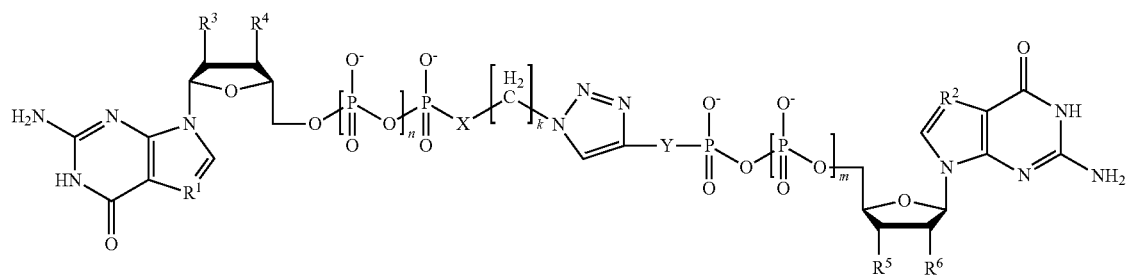

Formula I or a stereoisomer or salt thereof, wherein $R^1$ and $R^2$ are selected from the group consisting of N, $N^+$—CH$_3$, $N^+$—C$_2$H$_5$, $N^+$—C$_3$H$_8$, $N^+$—C$_4$H$_5$, $N^+$—CH$_2$C$_6$H$_5$ wherein at least one of $R^1$, $R^2$ is not N.

n and m are independently chosen from the group consisting of 0, 1 and 2;

X is selected from the group consisting of O, NH, S, CH$_2$ k is 1 or 2

Y is either void or selected from the group of —CH$_2$—, —CH$_2$CH$_2$—, —CH$_2$O—, —CH$_2$S—, —CH$_2$NH—, —CH$_2$CH$_2$O—, —CH$_2$CH$_2$NH—, —CH$_2$CH$_2$S—

$R^3$, $R^4$, $R^5$, $R^6$ are selected from the group consisting of H, OH, OCH$_3$, or OCH$_2$CH$_3$; wherein $R^3$ and $R^4$ may be the same or different; $R^5$ and $R^6$ may be the same or different; if either of $R^3$, $R^4$ is different than OH than $R^5$ and $R^6$ are both OH; if either of $R^5$, $R^6$ is different than OH than $R^3$ and $R^4$ are both OH.

In an embodiment of the compound according to the invention, $R^1$ is $N^+$—CH$_3$, $R^3$ and $R^4$ are selected from the group consisting of OH and OCH$_3$ and at least one of $R^3$, $R^4$ is not OH, $R^5$ and $R^6$ are both OH, n is at least 1.

In another embodiment of the compound according to the invention $R^2$ is $N^+$—CH$_3$, $R^5$ and $R^6$ are selected from the group consisting of OH and OCH$_3$ and at least one of $R^5$, $R^6$ is not OH, $R^3$ and $R^4$ are both OH, m is at least 1.

Preferably, the compound of the invention is selected from the group consisting of the following:

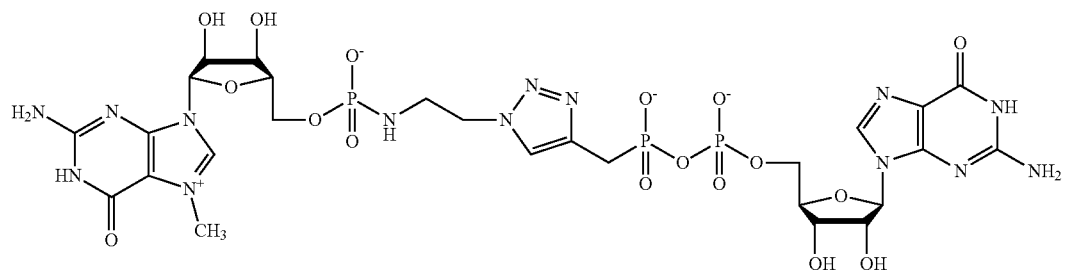
m⁷GpNHC₂H₄tCH₂ppG
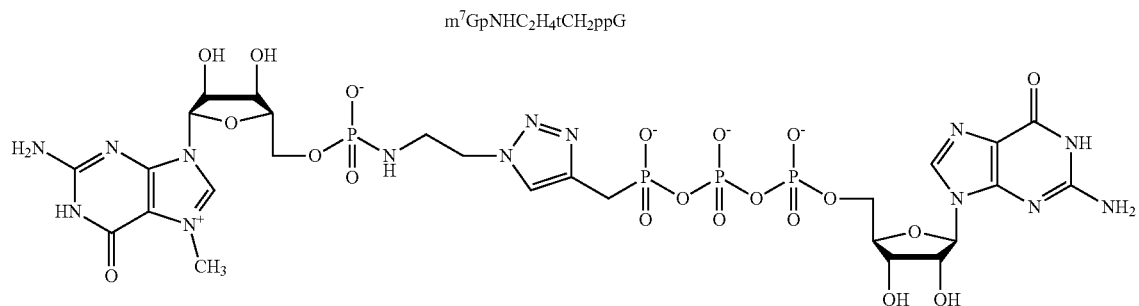
m⁷GpNHC₂H₄tCH₂pppG
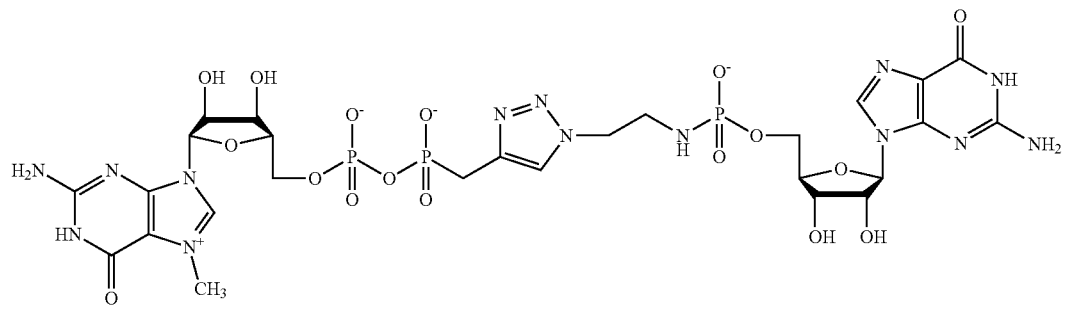
m⁷GppCH₂tC₂H₄NHpG
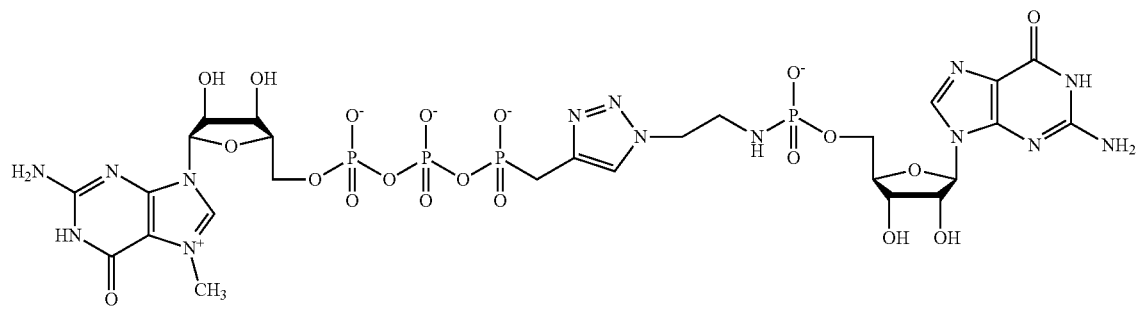
m⁷GpppCH₂tC₂H₄NHpG
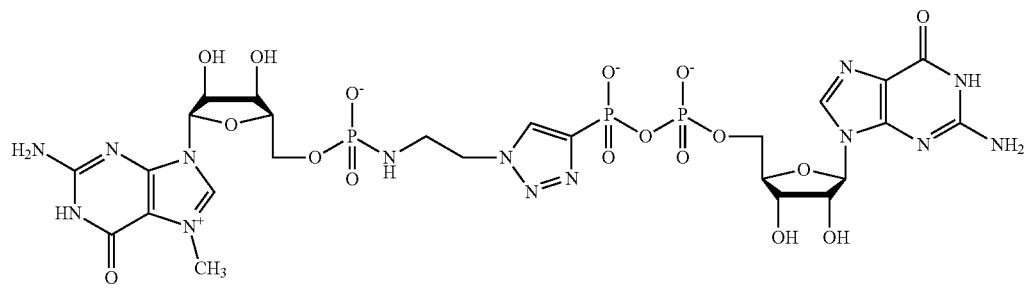
m⁷GpNHC₂H₄tppG -continued
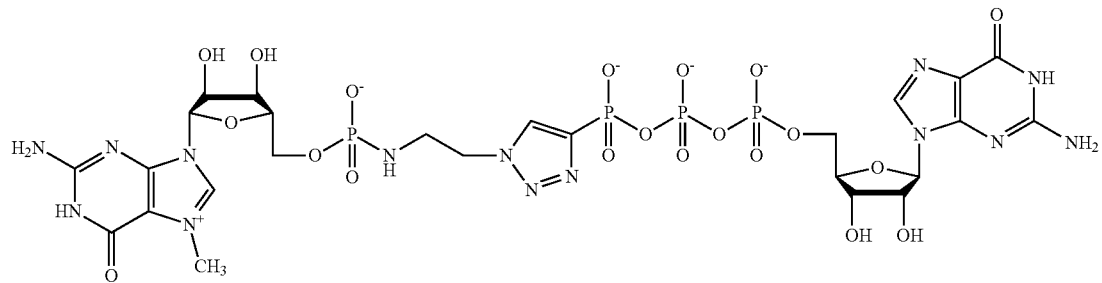
m⁷GpNHC₂H₄tpppG
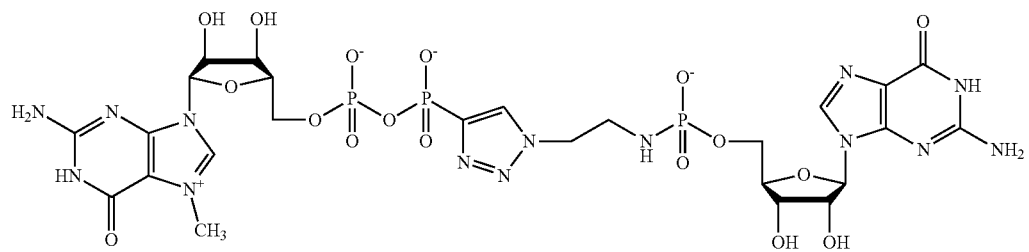
m⁷GpptC₂H₄NHpG
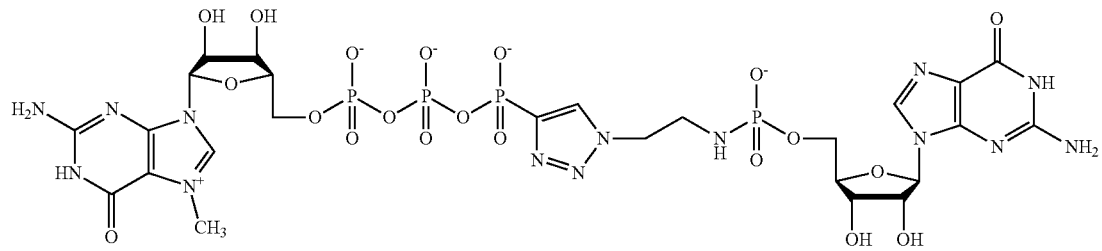
m⁷GppptC₂H₄NHpG
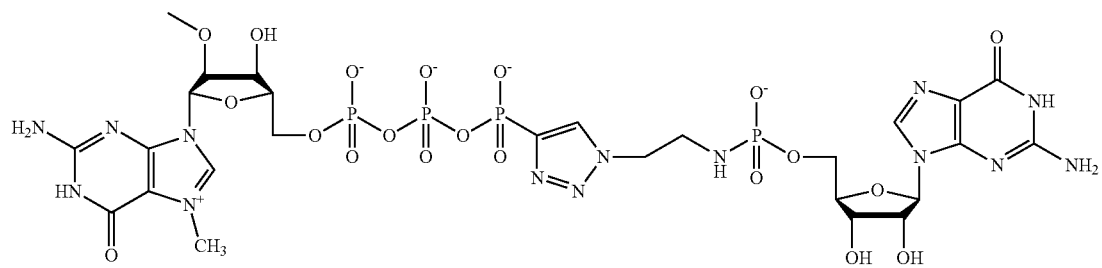
m₂^{7,2'-O}GppptC₂H₄NHpG
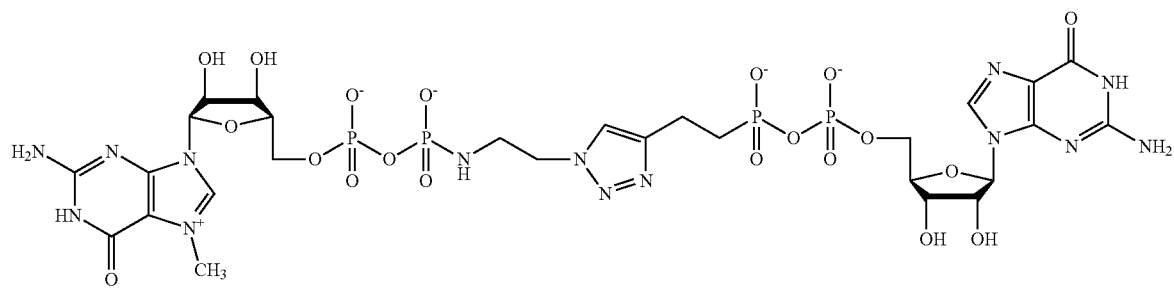
m⁷GppNHC₂H₄tppG

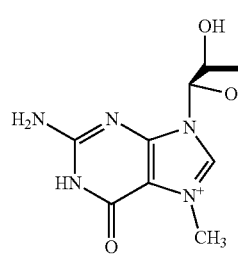
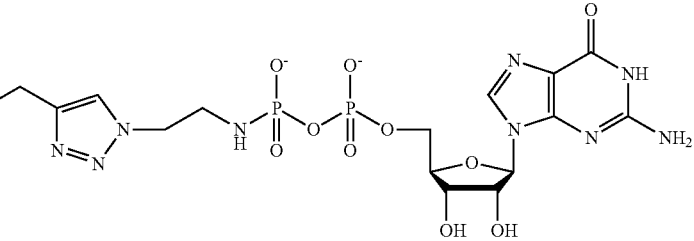

m⁷GppC₂H₄tC₂H₄NHppG

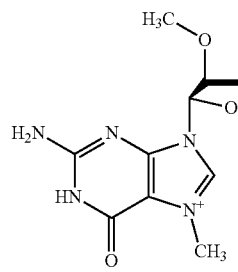

m$^{7,2'-O}$GppptC₂H₄NHppG

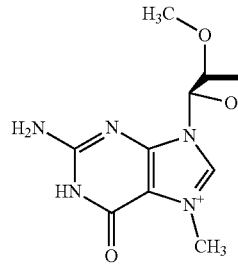

m$^{7,2'-O}$GppptC₂H₄OppG

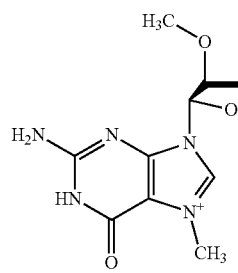

m$^{7,2'-O}$GppptC₂H₄OpG

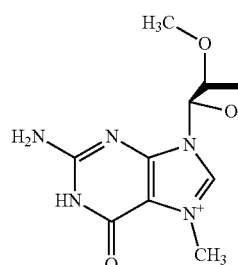

m$^{7,2'-O}$GpptC₂H₄OppG

The object of the invention is also a composition comprising at least one of the compounds of the invention or at least one stereoisomer or salt thereof and a suitable carrier or diluent.

The object of the invention is also an RNA molecule whose 5' end incorporates the compound of the invention.

The object of the invention is also a method of synthesizing, in vitro or in vivo, the RNA molecule of the invention, said method comprising reacting ATP, CTP, UTP, and GTP, the compound of the invention or the composition of the invention, and a polynucleotide template in the presence of RNA polymerase, in conditions enabling transcription by the RNA polymerase of the polynucleotide template into an RNA copy; whereby some of the RNA copies will incorporate the compound of the invention to make an RNA molecule of the invention.

The object of the invention is also a method of synthesizing a protein or peptide in vitro, said method comprising translating the RNA molecule of the invention in a cell-free protein synthesis system, wherein the RNA molecule comprises an open reading frame, in conditions enabling translation of the open reading frame of the RNA molecule into the protein or peptide encoded by the open reading frame.

The object of the invention is also a method of synthesizing a protein or peptide in vivo or in cultured cells, said method comprising translating the RNA molecule of the invention in vivo or in cultured cells, wherein the RNA molecule comprises an open reading frame, under conditions enabling translation of the open reading frame of the RNA molecule into the protein or peptide encoded by the open reading frame.

A further object of the invention is a use of the compound of the invention or the composition of the invention in an in vitro or in vivo synthesis of an RNA molecule.

A further object of the invention is a use of the RNA molecule of the invention in an in vitro or in vivo synthesis of a protein or peptide.

EXAMPLES

Example 1—Synthesis and Isolation of Cap Analogs

Figure 1:
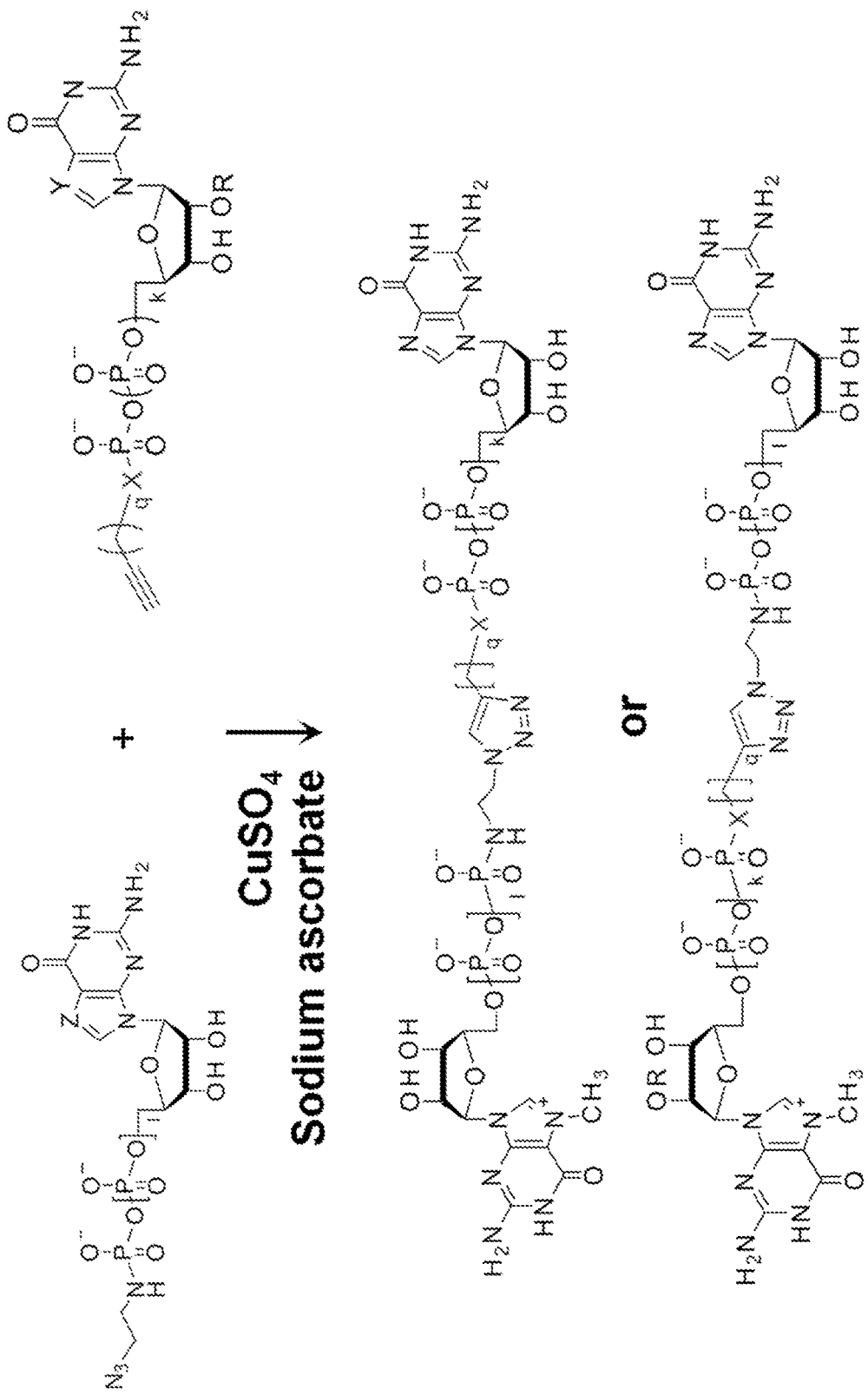
FIG. 1 depicts the synthesis of phosphotriazole cap analogues.

Phosphotriazole cap analogues were synthesized in CuAAC reactions between two "clickable" mononucleotide analogues, a guanine nucleotide containing a terminal alkyne within the phosphate chain and an appropriate azide-containing nucleotide (FIG. 1). The alkyne- and azide-containing reactants were coupled in different combinations under standard CuAAC conditions ($CuSO_4$, sodium ascorbate) in water or the mixture of water and tert-butanol (Table 1).

Table 1. lists several phosphotriazole cap analogs that were synthesized and characterized by chemical, biophysical, biochemical, and molecular biology methods. It also shows the structures of mononucleotides used as starting materials for the synthesis, and the HPLC yields of the corresponding syntheses. Compounds that are particularly favorable for production of capped mRNAs include $m^7GppptC_2H_4NHpG$, $m^7GpppCH_2tC_2H_4NHpG$, $m_2^{7,2'-O}GppptC_2H_4NHpG$, $m_2^{7,2'-O}GppptC_2H_4NHppG$, $m_2^{7,2'-O}GppptC_2H_4OppG$, $m_2^{7,2'-O}GppptC_2H_4OpG$, $m_2^{7,2'-O}GpptC_2H_4OppG$.

TABLE 1

| Azide-modified compound | Alkyne-modified compound |
|---|---|
| 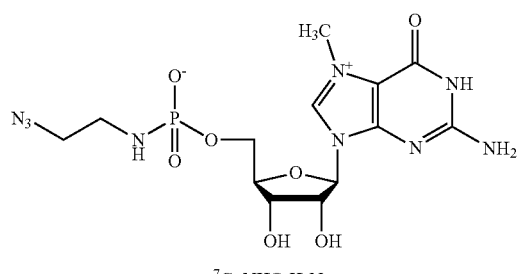<br>$m^7GpNHC_2H_4N_3$ | 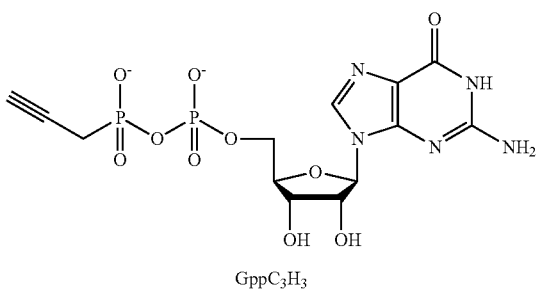<br>$GppC_3H_3$ |
| 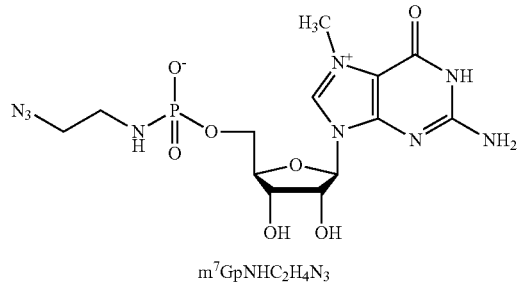<br>$m^7GpNHC_2H_4N_3$ | 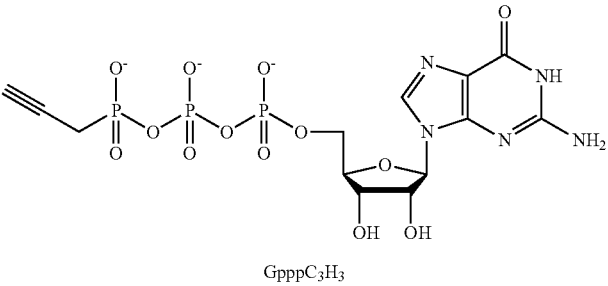<br>$GpppC_3H_3$ |

TABLE 1-continued
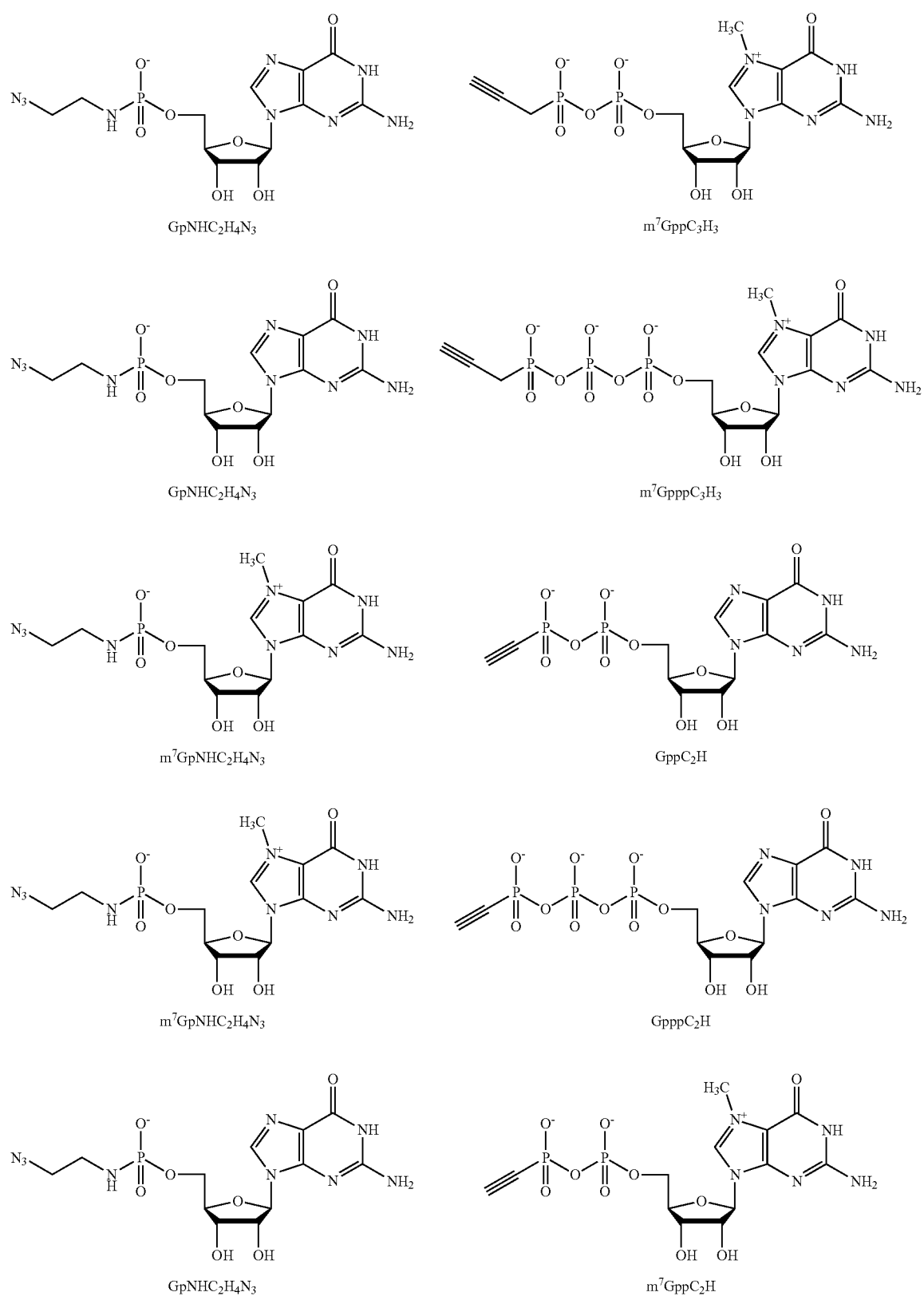

TABLE 1-continued
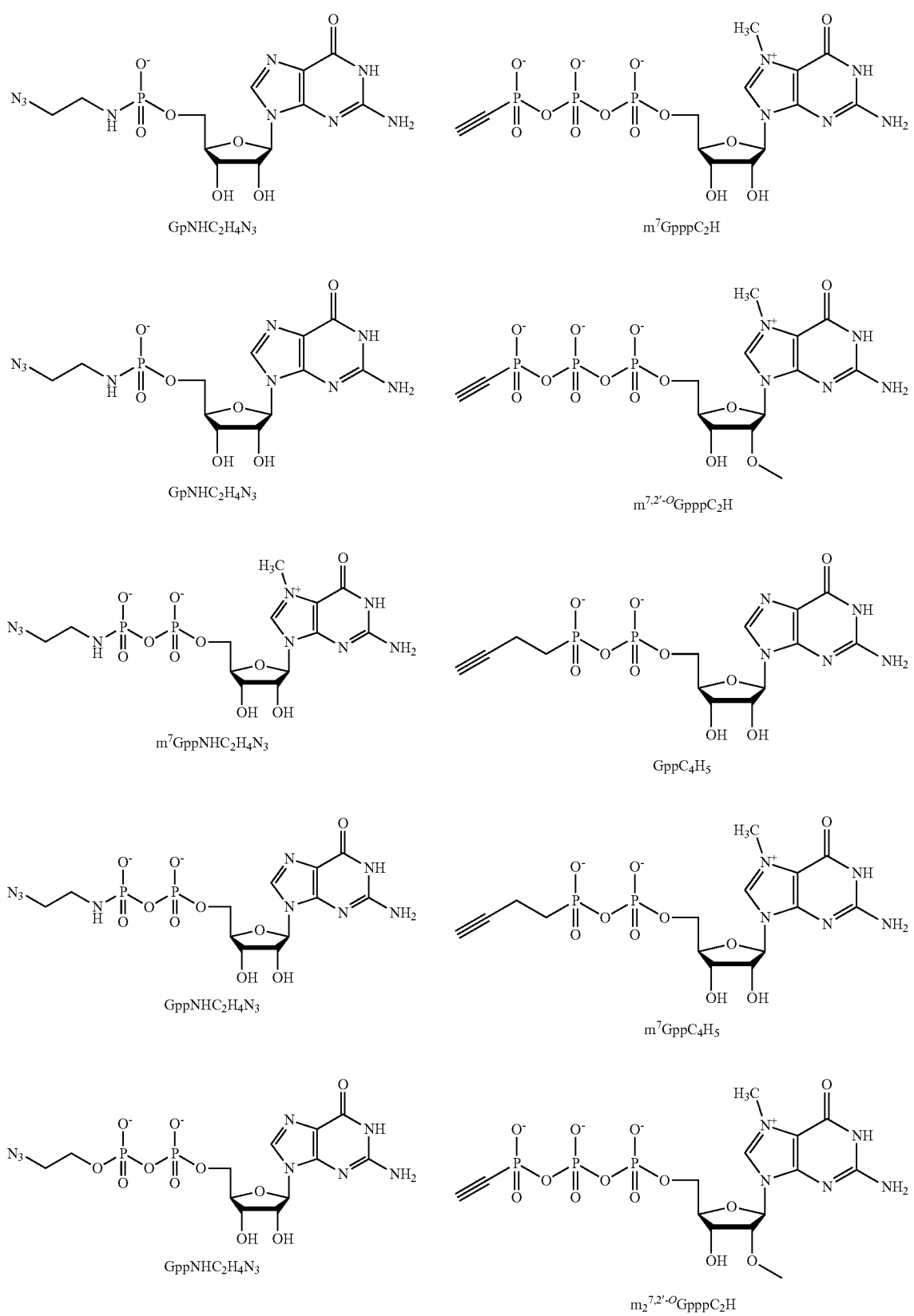

TABLE 1-continued
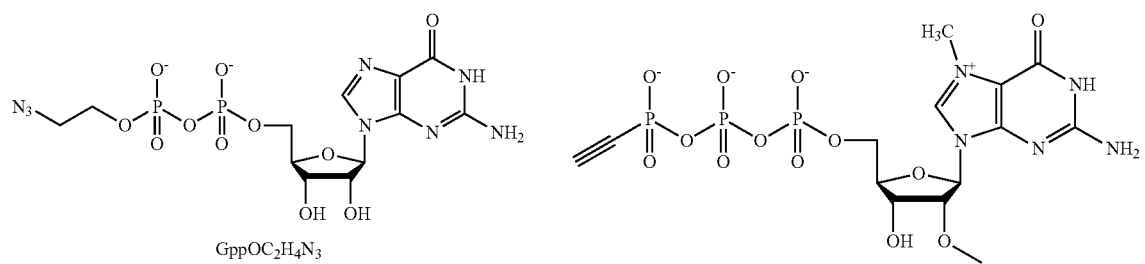
GppOC2H4N3
m2^{7,2'-O}GpppC2H
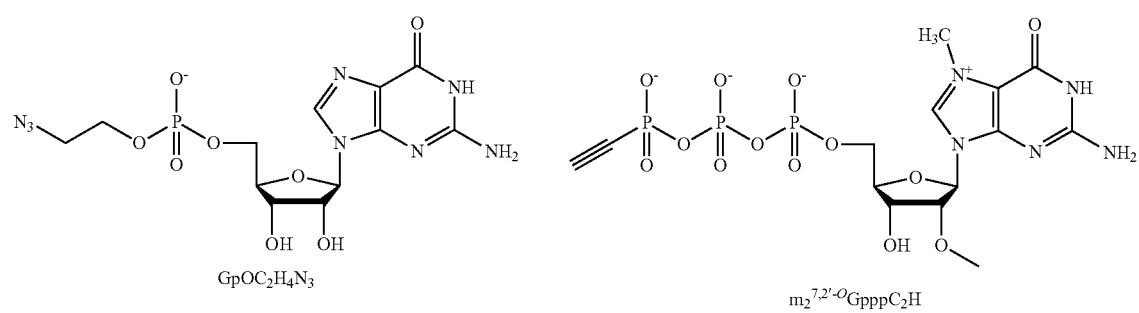
GpOC2H4N3
m2^{7,2'-O}GpppC2H
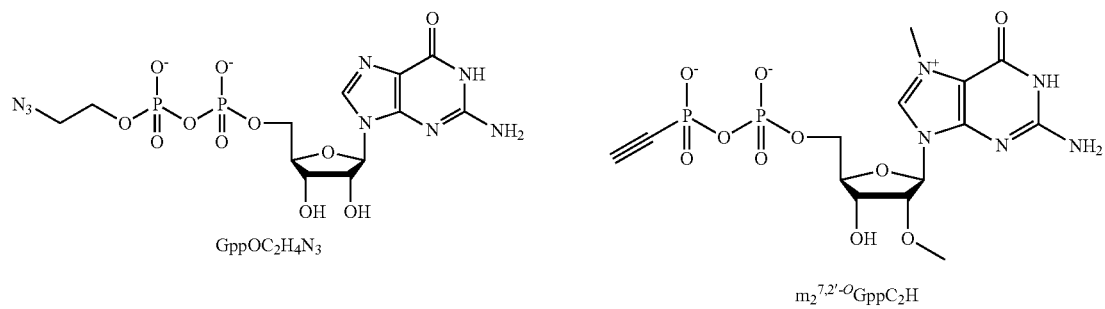
GppOC2H4N3
m2^{7,2'-O}GppC2H
| Phosphotriazole cap analog | HPLC yield |
|---|---|
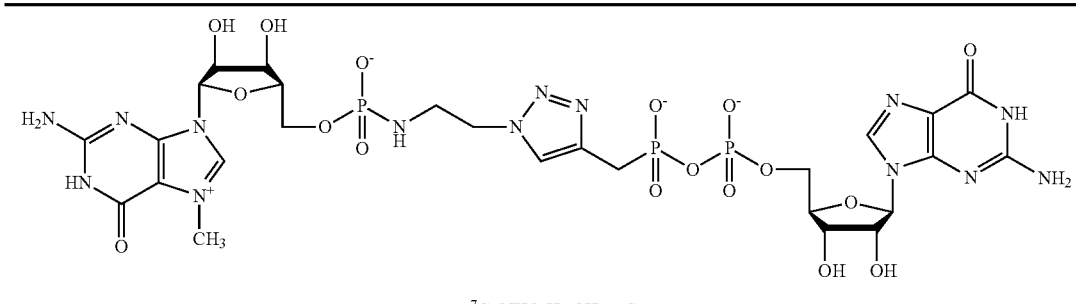
m7GpNHC2H4tCH2ppG
>99%
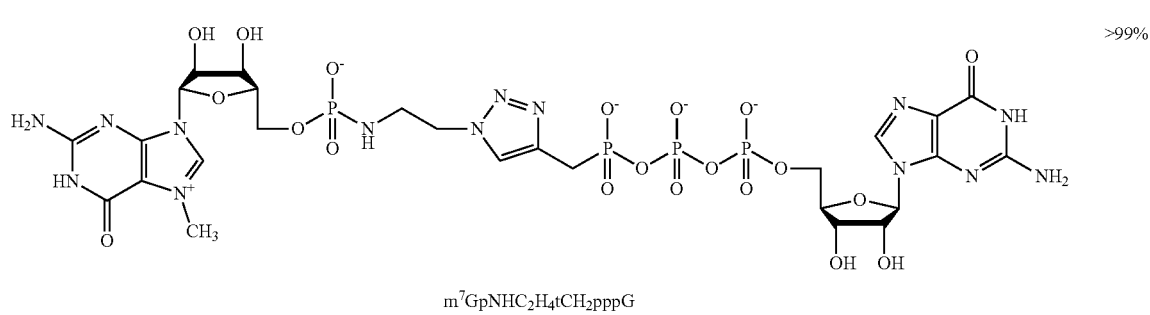
m7GpNHC2H4tCH2pppG
>99%

TABLE 1-continued
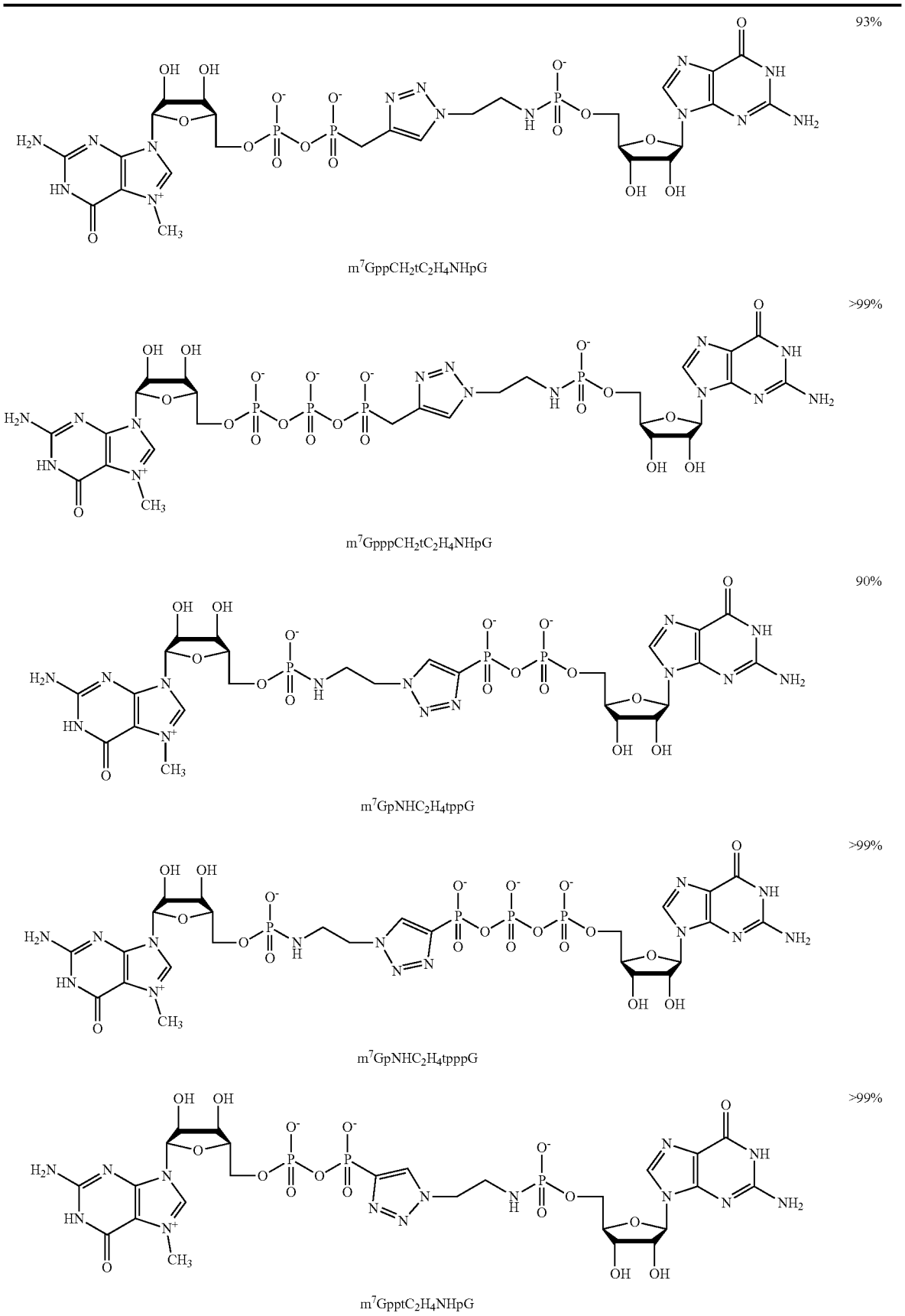
m⁷GppCH₂tC₂H₄NHpG  93%
m⁷GpppCH₂tC₂H₄NHpG  >99%
m⁷GpNHC₂H₄tppG  90%
m⁷GpNHC₂H₄tpppG  >99%
m⁷GpptC₂H₄NHpG  >99%

TABLE 1-continued
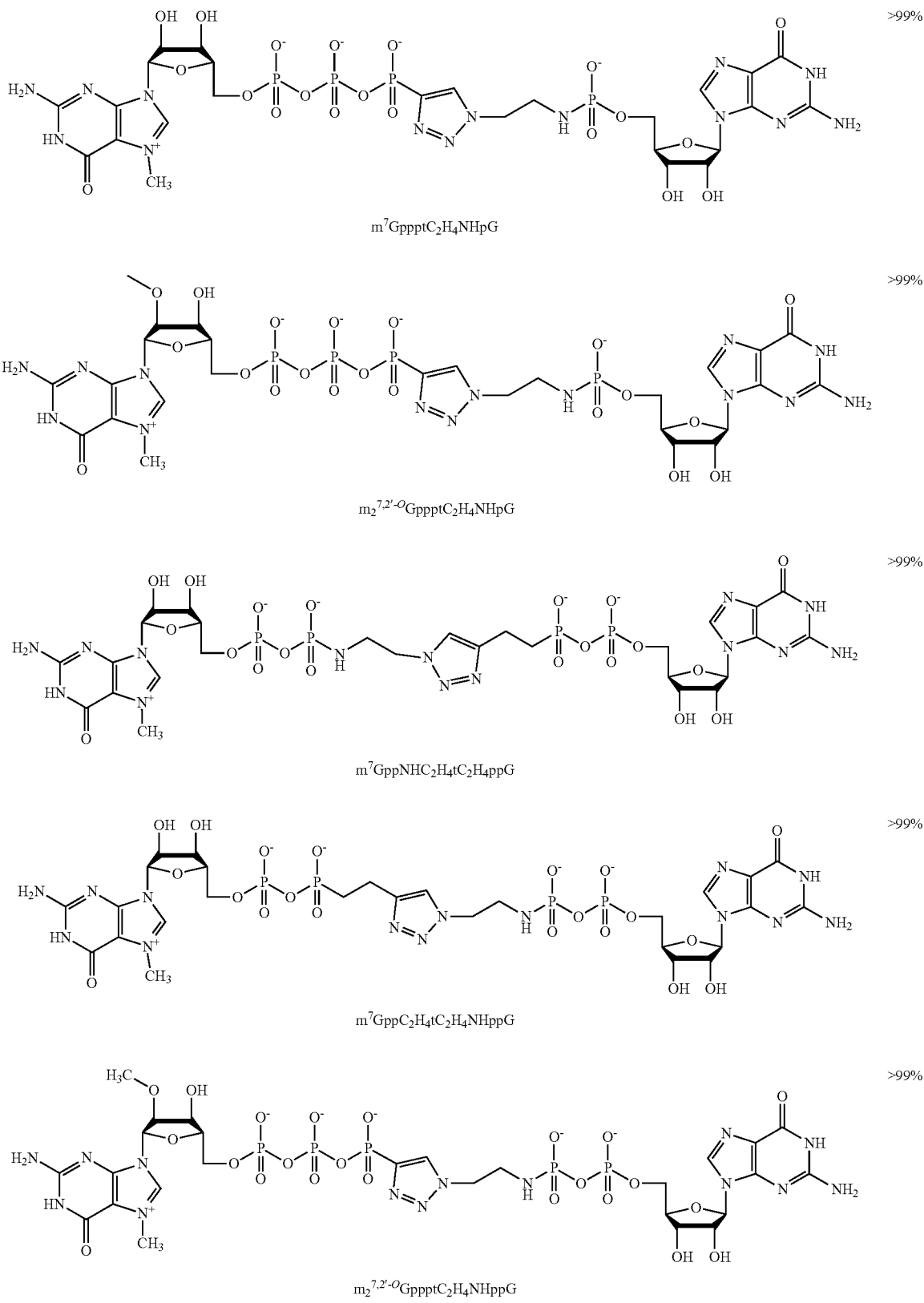
m⁷GppptC₂H₄NHpG >99%
m₂^{7,2'-O}GppptC₂H₄NHpG >99%
m⁷GppNHC₂H₄tC₂H₄ppG >99%
m⁷GppC₂H₄tC₂H₄NHppG >99%
m₂^{7,2'-O}GppptC₂H₄NHppG >99%

TABLE 1-continued

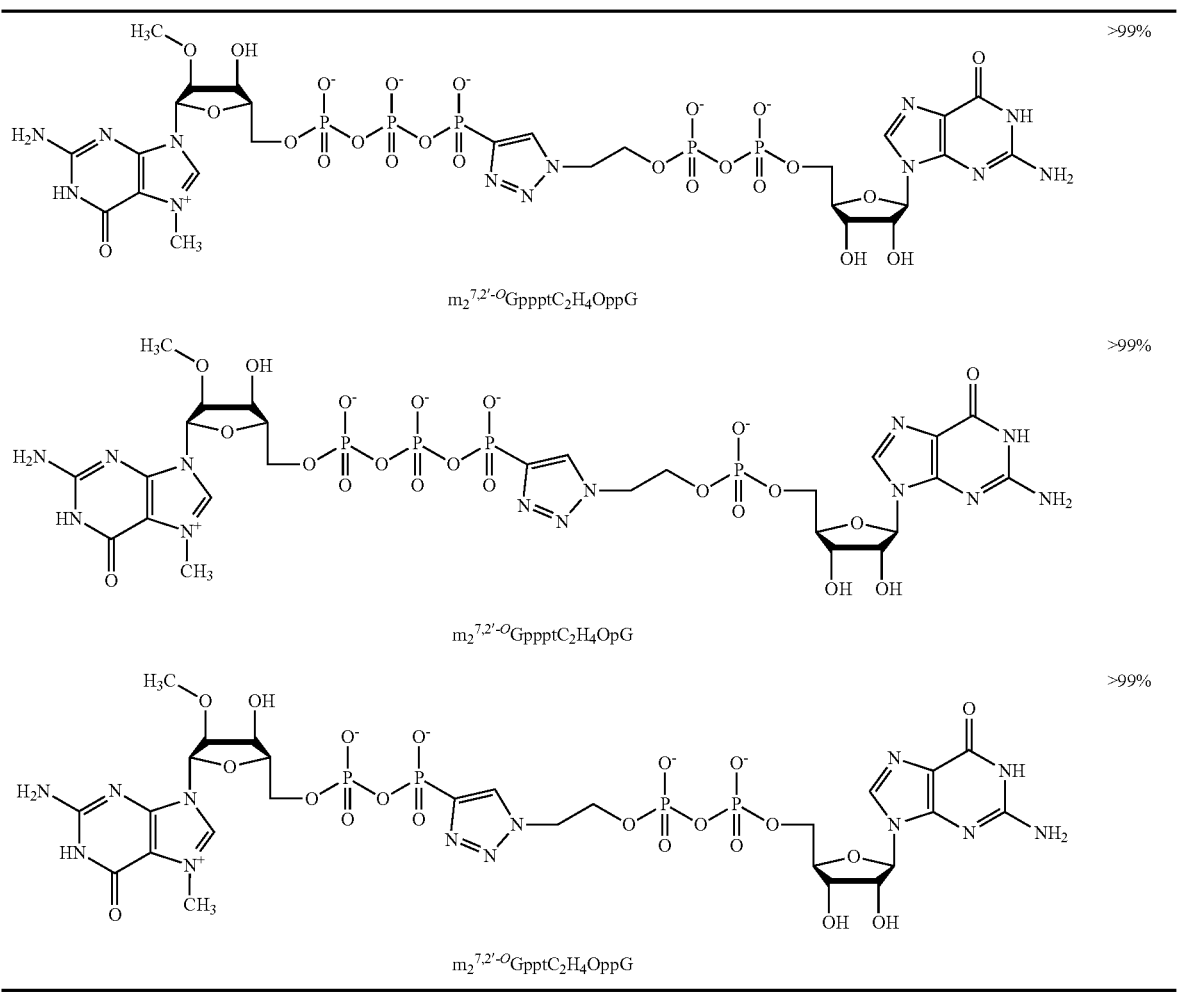

The reactions were quenched with EDTA to ensure the effective removal of copper ions, which could otherwise interfere with subsequent biological experiments, and directly purified by reversed phase high-performance liquid chromatography (RP HPLC). All dinucleotide cap analogues were obtained in good-to-excellent yields (70-100%, usually exceeding 90%) and isolated in high purity. The starting materials were obtained in 2-3 step from commercially available starting materials (Sigma-Aldrich). Alkyne-containing C-phosphonate analogues were obtained by $MgCl_2$-mediated coupling between triethylammonium salts of C-phosphonate subunits and guanosine mono- or diphosphate imidazolides, followed by N7-methylation by methyl iodide. Phosphoramidate analogues containing either an alkyne or azide moiety were synthesized by reacting propargylamine or 2-azidoethylamine and an appropriate guanine nucleotide imidazolide in aqueous buffer. Azide-containing phosphoester analogues were obtained either by $MgCl_2$-mediated coupling between triethylammonium salts of azidoethyl phosphate subunit and guanosine monophosphate imidazolide or by the reaction between protected guanosine H-phosphonate and azidoethanol followed by removal of protecting groups.

1.1. Starting Materials and Chemical Reagents

All solvents and reagents were synthesis grade and used without further treatment, unless otherwise stated. C-phosphonate nucleotide analogues ($GppC_2H$, $GppC_3H_3$, $GppC_4H_5$, $GpppC_2H$, $GpppC_3H_3$, $GpppC_4H_5$),[38] 2'-O-methylguanosine 5'-monophosphate[6],2-azidoethanamine[39] and 2',3'-O,O-isopropylideneguanosine[46] were synthesized as described previously in the respective cited literature.

1.2. Chromatography 1.2.1. Ion-Exchange Chromatography

The synthesized mononucleotide analogues functionalized with either alkyne or azide group were purified by ion-exchange chromatography on DEAE Sephadex A-25 ($HCO_3^-$ form) column. After loading the column with reaction mixture and washing it with water, the products were eluted using different gradients of TEAB in deionized water: 0-0.7 M for nucleoside monophosphates, 0-1.0 M for nucleoside diphosphates or 0-1.2 M nucleoside triphosphates. Fractions containing the desired product were collected together after RP HPLC and spectrophotometric analysis (at 260 nm). Evaporation under reduced pressure with repeated additions of 96% ethanol, then 99.8% ethanol and, at the end, MeCN resulted in isolation of nucleotide analogues as triethylammonium (TEA) salts.

1.2.2. Analytical and Preparative Reverse-Phase (RP) HPLC

Both analytical and semi-preparative HPLC were performed on Agilent Technologies Series 1200 with UV-detection at 254 nm and fluorescence detection (Ex: 260 nm, Em: 370 nm). For chemical and enzymatic reactions, monitoring analytical HPLC was performed using Supelcosil LC-18-T column (4.6×250 mm, 5 μm, flow rate 1.3 mL/min) with one of three different linear gradients of methanol in 0.05 M ammonium acetate buffer (pH 5.9): program A—gradient 0-25% of methanol in 15 min, program B—gradient 0-50% of methanol in 15 min, program C—gradient 0-50% of methanol in 7.5 min and then isocratic elution (50% of methanol) until 15 min. For pH-dependent degradation studies and reactions monitoring of different steps of ARCA analogues synthesis analytical HPLC was performed using Grace VisionHT C18-HL column (4.6×250 mm, 5 μm, flow rate 1.3 mL/min) with linear gradient 0-25% of methanol in 0.05 M ammonium acetate buffer (pH 5.9) in 15 min. Semi-preparative RP HPLC was performed using Discovery RP Amide C-16 HPLC column (25 cm×21.2 mm, 5 μm, flow rate 5.0 mL/min) with linear gradients of acetonitrile in 0.05 M ammonium acetate buffer (pH 5.9). The products, after at least triple lyophilisation, were isolated as ammonium salts.

Figure 2:
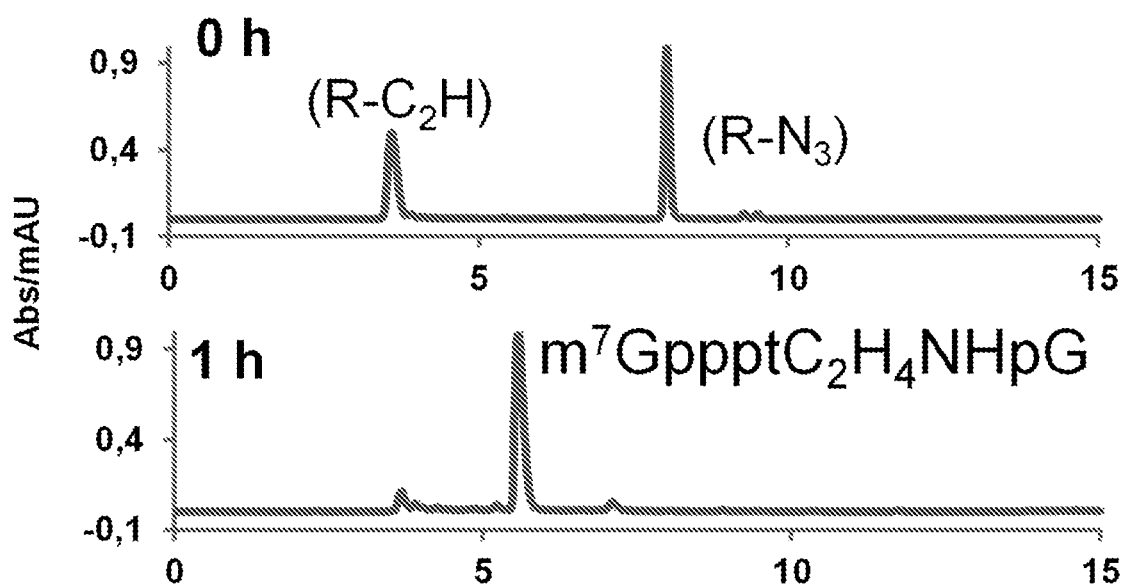
FIG. 2 depicts example RP HPLC analysis of CuAAC reaction leading to phosphotriazole cap analog.

Examplary results for RP HPLC analysis of CuAAC reaction leading to phosphotriazole cap analog are shown in FIG. 2

1.3. Yields and Concentrations Determination

The yields of mononucleotide analogues after ion-exchange purification and the concentrations of mono- and dinucleotide analogues solutions used for biophysical and biological experiments were determined on the basis of absorbance measurements performed at 260 nm in 0.1 M phosphate buffer pH 6.0 for 7-methylguanine mononucleotide analogues and in 0.1 M phosphate buffer pH 7.0 for dinucleotide analogues and guanine mononucleotide analogues. The quantities of obtained ion-exchange purified products were expressed as optical density miliunits (opt. mu=absorbance of the solution by volume in mL). For calculations of yields and concentrations following molar extinction coefficients [$M^{-1}cm^{-1}$] were employed: ε=22600 (dinucleotides), ε=11400 ($m^7G$ mononucleotides), ε=12080 (G mononucleotides). Concentrations of transcripts were determined using NanoDrop 2000c Spectrofotometer (Thermo Scientific).

1.4. NMR Spectroscopy and Mass Spectrometry

The structure and purity of each final product were confirmed by high resolution mass spectrometry using negative or positive electrospray ionization (HRMS (−) ESI or HRMS (+) ESI) and $^1$H NMR, $^{31}$P NMR, gDQCOSY and gHSQCAD spectroscopy. Mass spectra were recorded on Thermo Scientific LTQ OrbitrapVelos spectrometer. NMR spectra were recorded on a Varian INOVA 400 MHz or 500 MHz spectrometer equipped with a high stability temperature unit using 5 mm 4NUC probe, at 25° C. if not stated otherwise, at 399.94/500.61 MHz ($^1$H NMR) and 161.90/202 MHz ($^{31}$P NMR). The $^1$H NMR and $^{31}$P NMR chemical shifts were reported in ppm and referenced to respective internal standards: sodium 3-(trimethylsilyl)-2,2',3,3' tetradeuteropropionate (TSP) and 20% phosphorus acid in $D_2O$. Signals in $^1$H NMR spectra of dinucleotides were assigned according to 2D NMR spectra (gDQCOSY, gHSQCAD). In $^{31}$P signal assignment of dinucleotide cap analogues the phosphates were denoted analogously to $m^7G(p_\delta)p_\gamma p_\beta p_{60}G$.

Some cap analogues hydrolyzed in $D_2O$ gradually. Although pure compounds (see HPLC profiles, Supporting Information 2) were dissolved in $D_2O$ just before measurements, the spectra indicated some level of hydrolysis. % of hydrolysis is provided along with compound characterization data, if higher than 5%.

1.5. Synthesis of Nucleotide Imidazolide Derivatives 1.5.1. Preparation of Compounds for Imidazole-Activation Preparation of Triethylammonium (TEA) Salts The commercially available guanosine 5'-monophosphate (GMP) disodium salt and tetrasodium pyrophosphate were converted into triethylammonium forms by passing their aqueous solutions (ca. 1 g/20 mL) through Dowex 50 W×8 cationite. The collected eluates were evaporated under reduced pressure with repeated additions of ethanol and acetonitrile to dryness yielding the nucleotide triethylammonium salt as a white solid and triethylammonium pyrophosphate as colorless oil.

Triethylammonium phosphate was prepared by slowly adding triethylamine to the low-concentrated solution of $H_2PO_4$ in water until pH 7 was obtained which was followed by evaporation to afford oily, colorless residue.

Synthesis of Guanosine 5'-Diphosphate (GDP), Guanosine 5'-Triphosphate (GTP) and 2'-O-Methylguanosine 5'-Diphosphate ($m^{2'\text{-}O}GDP$)

Triethylammonium phosphate (4 equiv.) or triethylammonium pyrophosphate (4 equiv.) was suspended in DMF (ca. 0.4 M) in the presence of $ZnCl_2$ (4 equiv.) and stirred for ~5 min to obtain a solution. Then, GMP-Im or $m^{2'\text{-}O}$GMP-Im (1 equiv.) along with a second portion of $ZnCl_2$ (4 equiv.) was added and the mixture was stirred for 1-2 h at room temperature. The reaction was stopped by 10-fold dilution with water and addition of EDTA (8 equiv.) and $NaHCO_3$ (ca. 17.6 equiv.). The ion-exchange purification afforded triethylammonium salt of GDP (64%), GTP (79%) and $m^{2'\text{-}O}GDP$ (95%).

N7-Methylation of Guanine Nucleotides (GMP, GDP and GTP)

An appropriate analogue (GMP, GDP or GTP, TEA salt) was dissolved in dry DMSO to obtain ca. 0.1 M solution followed by addition of $CH_3I$ (8 equiv.). The mixture was stirred at room temperature for several hours until HPLC analysis indicated more than 90% conversion of the substrate and the presence of $N^7$-methylated nucleotide as the major product. The reaction was stopped by 10-fold dilution with water and organic-soluble compounds were removed by 3-time washing with diethyl ether. The aqueous phase was then treated with a pinch of $Na_2S_2O_5$ to reduce the residual iodine and the pH of solution was set to 7 by addition of solid $NaHCO_3$. The following ion-exchange purification afforded triethylammonium salt of $m^7GMP$ (63%), $m^7GDP$ (68%) or $m^7GTP$ (58%).

1.5.2. Activation with Imidazole

Synthesis of Nucleotide Imidazolides

Compounds were prepared according to Mukaiyama and Hashimoto.[40] An appropriate nucleotide (1 eq., TEA salt), imidazole (10 equiv.), 2,2'-dithiodipyridine (3 equiv.) were mixed in DMF (~2.5 mL/100 mg of nucleotide) before addition of triethylamine (3 equiv.) and triphenylphosphine (3 equiv.). The mixture was stirred for 6-8 h at room temperature. The addition of a solution of anhydrous $NaClO_4$ (4 equiv.) in dry acetone (~8 volumes of DMF volume) resulted in precipitation of the product as sodium salt. The suspension was cooled at 4° C. and the precipitate was filtered off, washed repeatedly with cold, dry acetone and dried in vacuum over $P_4O_{10}$. Yields 90-100%.

1.6. Synthesis of $m^7G$ C-Phosphonate Nucleotide Analogues

General Procedure B (GP B): $N^7$-Methylation of Guanine Nucleotides Using $CH_3I$ An appropriate nucleotide (TEA salt) was dissolved in dry DMSO to obtain ca. 0.1 M solution followed by addition of $CH_3I$ (8 equiv.). The mixture was stirred at room temperature for several hours until HPLC analysis indicated more than 90% conversion of the substrate and the presence of $N^7$-methylated nucleotide as the major product. The reaction was stopped by 10-fold dilution with water and organic-soluble compounds were removed by 3-time washing with diethyl ether. The aqueous phase was then treated with a pinch of $Na_2S_2O_5$ to reduce the residual iodine and the pH of solution was set to 7 by addition of solid $NaHCO_3$. The product was purified by ion-exchange chromatography on DEAE Sephadex A-25 and evaporated to dryness as described in General Information. Prior to NMR characterization the product was additionally purified by semi-preparative HPLC as described in General Information.

General Procedure C (GP C): $N^7$-Methylation of Guanine Nucleotides Using $(CH_3)_2SO_4$ An appropriate nucleotide (TEA salt) was dissolved at ~0.2 M concentration in ca. 0.5 mM aqueous $CH_3COOH$ (pH 4) to obtain ca. 0.2 M solution. Then, 5 portions of $(CH_3)_2SO_4$ (2 equiv. each) were added every 10 min to the mixture under vigorous stirring and the pH was maintained at 4 by adding 10% KOH if necessary. The stirring was continued at room temperature for several hours until HPLC analysis indicated more than 90% conversion of the substrate and the presence of $N^7$-methylated nucleotide as the major product. The reaction was stopped by 10-fold dilution with water and organic-soluble compounds were removed by 3-time washing with diethyl ether. The pH of aqueous phase was then set to 7 by addition of solid $NaHCO_3$. The product was purified by ion-exchange chromatography on DEAE Sephadex A-25 and evaporated to dryness as described in General Information. Prior to NMR characterization the product was additionally purified by semi-preparative HPLC as described in General Information.

β-C-(2-Ethynyl), β-C-(2-Propargyl) and β-C-(3-Butynyl) Guanosine Diphosphate and γ-C-(2-Ethynyl), γ-C-(2-Propargyl) and γ-C-(3-Butynyl) Guanosine Triphosphate Triethylammonium Salts ($GppC_2H$, $GppC_3H_3$, $GppC_4H_5$, $GpppC_2H$, $GpppC_3H_3$, $GpppC_4H_5$)

Compounds were obtained according to Wanat et al.[38] Briefly, triethylammonium 3-butynyl C-phosphonate, tributylammonium 3-trimethylsilyl-1-propargyl C-phosphonate or triethylammonium 2-ethynyl C-phosphonate (each 2.5 equiv.) was stirred in DMF (ca. 0.4 M) until complete dissolution. Then, an appropriate nucleotide imidazolide (1 equiv.) along with $MgCl_2$ (8 equiv.) were added and the mixture was stirred for 1-2 h at room temperature. The reaction was stopped by 10-fold dilution with water. The product was purified by ion-exchange chromatography on DEAE Sephadex A-25 and evaporated to dryness as described in General Information to afford products in a form of triethylammonium salts. Trimethylsililpropargylophosphonate nucleotide analogues were then deprotected by incubation in TBAF/THF (1 M):ACN (1:3, v/v) mixture (1.1 equiv. of TBAF per nucleotide) at room temperature for 24 h. After removing the solvent under reduced pressure, the crude product was directly subjected to click reactions. Yields: 45-90%.

β-C-(3-Butynyl) 7-Methylguanosine Diphosphate Ammonium Salt ($m^7GppC_4H_5$)

Obtained according to GP B starting from β-C-(3-butynyl) guanosine diphosphate triethylammonium salt (11000 mOD, 0.910 mmol), $CH_3I$ (0.454 mL, 7.285 mmol) and DMSO (9.0 mL). The ion-exchange purification afforded 7061 mOD (0.619 mmol, 68%) of $m^7GppC_4H_5$ triethylammonium salt. Additional HPLC purification of a fraction of obtained product gave $m^7GppC_4H_5$ as ammonium salt.

$^1$H NMR (400 MHz, $D_2O$, 25° C.) $\delta_H$: 9.21 (1H, s, H8), 6.08 (1H, d, $J_{1'-2'}$=3.6, H1'), 4.70 (1H, dd, $J_{1'-2'}$=3.6, $J_{2'-3'}$=4.7, H2'), 4.51 (1H, dd, $J_{2'-3'}$=4.7, $J_{3'-4'}$=5.5, H3'), 4.39-4.43 (1H, m, H4'), 4.34 (1H, ddd, $J_{5'-5''}$=12.0, J=4.2, 2.5, H5'), 4.22 (1H, ddd, $J_{5'-5''}$=12.0, J=5.2, 2.2, H5''), 4.13 (3H, s, $m^7$), 2.46 (2H, dtd, $J_{CH2(C2H)-CH}$=2.6, $J_{CH2(C2H)-CH2(P)}$=8.1, $J_{CH2(C2H)-P\beta}$=10.1, $H_{CH2(C2H)}$), 2.34 (1H, t, $J_{CH-CH2(C2H)}$=2.6, $H_{CH}$), 1.94 (2H, dt, $J_{CH2(C2H)-CH2(P)}$=8.1, $J_{CH2(P)-P\beta}$=16.9, $H_{CH2(P)}$); $^{31}$P NMR (162 MHz, $D_2O$, 25° C.) $\delta_P$: 16.45 (1P, dtt, $J_{CH2(C2H)-P\beta}$=10.1, $J_{CH2(P)-P\beta}$=16.9, $J_{P\alpha-P\beta}$=26.6, Pβ), −11.34 (1P, br d, $J_{P\alpha-P\beta}$=26.6, Pα); HRMS (−) ESI m/z found: 492.0692, calc. for $C_{15}H_{20}N_5O_{10}P_2^-$: 492.0685.

γ-C-(3-Butynyl) 7-Methylguanosine Triphosphate Ammonium Salt ($m^7GpppC_4H_5$)

Obtained according to GP B starting from γ-C-(3-butynyl) guanosine triphosphate triethylammonium salt ($GpppC_4H_5$) (11000 mOD, 0.910 mmol), $CH_3I$ (0.454 mL, 7.285 mmol) and DMSO (9.0 mL). The ion-exchange purification afforded 7677 mOD (0.673 mmol, 74%) of $m^7GpppC_4H_5$ triethylammonium salt. Additional HPLC purification of a fraction of obtained product gave $m^7GpppC_4H_5$ as ammonium salt.

$^1$H NMR (400 MHz, $D_2O$, 25° C.) $\delta_H$: 9.23 (1H, s, H8), 6.08 (1H, d, $J_{1'-2'}$=3.5, H1'), 4.69 (1H, dd, $J_{1'-2'}$=3.5, $J_{2'-3'}$=4.7, H2'), 4.54 (1H, dd, $J_{2'-3'}$=4.7, $J_{3'-4'}$=5.5, H3'), 4.35-4.42 (2H, overlapped H4' and H5'), 4.26 (1H, ddd, $J_{5'-5''}$=12.0, J=5.2, 1.7, H5''), 4.13 (3H, s, $m^7$), 2.44 (2H, dtd, $J_{CH-CH2(C2H)}$=2.5, $J_{CH2(P)-CH2(C2H)}$=8.3, $J_{CH2(C2H)-P\gamma}$=11.2, $H_{CH2(C2H)}$), 2.26 (1H, t, $J_{CH-CH2(C2H)}$=2.5, $H_{CH}$), 1.99 (2H, dt, $J_{CH2(P)-CH2(C2H)}$=8.3, $J_{CH2(P)-P\gamma}$=16.7, $H_{CH2(P)}$); $^{31}$P NMR (162 MHz, $D_2O$, 25° C.) $\delta_P$: 16.46 (1P, dtt, $J_{CH2(C2H)-P\gamma}$=11.2, $J_{CH2(P)-P\gamma}$=16.7, $J_{P\beta-P\gamma}$=25.0, Pγ), −11.47 (1P, br d, $J_{P\alpha-P\beta}$=19.2, Pα), −23.10 (1P, dd, $J_{P\alpha-P\beta}$=19.2, $J_{P\beta-P\gamma}$=25.0, Pβ); HRMS (−) ESI m/z found: 572.0357, calc. for $C_{15}H_{21}N_5O_{13}P_3^-$: 572.0349.

β-C-(2-Propargyl) 7-Methylguanosine Diphosphate Ammonium Salt ($m^7GppC_3H_3$)

Obtained according to GP B starting from β-C-(2-propargyl) guanosine diphosphate triethylammonium salt (8310 mOD, 0.688 mmol), $CH_3I$ 0.343 mL, 5.503 mmol) and DMSO (7.0 mL). The ion-exchange purification afforded 4706 mOD (0.413 mmol, 60%) of $m^7GppC_3H_3$ triethylammonium salt. Additional HPLC purification of a fraction of obtained product gave $m^7GppC_3H_3$ as ammonium salt.

$^1$H NMR (400 MHz, $D_2O$, 25° C.) $\delta_H$: 6.06 (1H, d, $J_{1'-2'}$=3.5, H1'), 4.68 (1H, dd, $J_{1'-2'}$=3.5, $J_{2'-3'}$=5.0, H2'), 4.50 (1H, dd, $J_{2'-3'}$=5.0, $J_{3'-4'}$=5.5, H3'), 4.40-4.42 (1H, m, H4'), 4.36 (1H, ddd, $J_{5'-5''}$=11.8, J=4.0, 2.4, H5'), 4.23 (1H, ddd, $J_{5'-5''}$=11.8, J=5.4, 2.0, H5''), 4.12 (3H, s, $m^7$), 2.76 (2H, dd, $J_{CH2-P\beta}$=21.4, $J_{CH2-CH}$=2.7, $H_{CH2}$), 2.34 (1H, dt, $J_{CH-CH2}$=2.7, $J_{CH-P\beta}$=6.5, $H_{CH}$); $^{31}$P NMR (162 MHz, $D_2O$, 25° C.) $\delta_P$: 9.44 (1P, dtd, $J_{P\alpha-P\beta}$=24.2, $J_{CH2-P\beta}$=21.4, $J_{CH-P\beta}$=6.5, Pβ), −10.76 (1P, br d, $J_{P\alpha-P\beta}$=24.2, Pα); HRMS (−) ESI m/z found: 478.0521, calc. for $C_{14}H_{18}N_5O_{10}P_2^-$: 478.0529.

γ-C-(2-Propargyl) 7-Methylguanosine Triphosphate Ammonium Salt ($m^7GpppC_3H_3$)

Obtained according to GP B starting from γ-C-(2-propargyl) guanosine triphosphate triethylammonium salt (10000 mOD, 0.828 mmol), $CH_3I$ (0.412 mL, 6.622 mmol) and DMSO (8.0 mL). The ion-exchange purification afforded 6324 mOD (0.555 mmol, 67%) of $m^7GpppC_3H_3$ triethylammonium salt. Additional HPLC purification of a fraction of obtained product gave 11d as ammonium salt.

$^1$H NMR (400 MHz, $D_2O$, 25° C.) $\delta_H$: 6.06 (1H, d, $J_{1'-2'}$=3.49, H1'), 4.69 (1H, dd, $J_{1'-2'}$=3.49, $J_{2'-3'}$=4.73, H2'), 4.53 (1H, dd, $J_{2'-3'}$=4.73, $J_{3'-4'}$=5.48, H3'), 4.35-4.42 (1H, overlapped H4' and H5'), 4.24-4.28 (1H, ddd, $J_{5'-5''}$=11.7, J=5.2, 2.0, H5''), 4.13 (3H, s, $m^7$), 2.78 (2H, dd, $J_{CH2-P\gamma}$=21.7, $J_{CH2-CH}$=2.5, $H_{CH2}$), 2.34 (1H, dt, $J_{CH2-CH}$=2.5, $J_{CH-P\gamma}$=6.5, $H_{CH}$); $^{31}$P NMR (162 MHz, $D_2O$, 25° C.) $\delta_P$: 9.38 (1P, dtd, $J_{CH2-P\gamma}$=21.7, $J_{P\beta-P\gamma}$=23.9, $J_{CH-P\gamma}$=6.5, P$\gamma$), −10.85 (1H, br d, $J_{P\alpha-P\beta}$=19.2, P$\alpha$), −22.50 (1P, dd, $J_{P\alpha-P\beta}$=19.2, $J_{P\beta-P\gamma}$=23.9, P$\beta$); HRMS (−) ESI m/z found: 558.0184, calc. for $C_{14}H_{19}N_5O_{13}P_3^-$: 558.0192.

β-C-(2-Ethynyl) 7-Methylguanosine Diphosphate Ammonium Salt ($m^7GppC_2H$)

Obtained according to GP C starting from β-C-(2-ethynyl) guanosine diphosphate triethylammonium salt (10000 mOD, 0.828 mmol), $(CH_3)_2SO_4$ (0.785 mL, 8.278 mmol) and $CH_3COOH$ solution pH 4 (8.0 mL). The ion-exchange purification afforded 4814 mOD (0.422 mmol, 51%) of $m^7GppC_2H$ triethylammonium salt. Additional HPLC purification of a fraction of obtained product gave $m^7GppC_2H$ as ammonium salt.

$^1$H NMR (400 MHz, $D_2O$, 25° C.) $\delta_H$: 6.08 (1H, d, $J_{1'-2'}$=3.7, H1'), 4.70 (1H, dd, $J_{1'-2'}$=3.7, $J_{2'-3'}$=4.7, H2'), 4.51 (1H, dd, $J_{2'-3'}$=4.7, $J_{3'-4'}$=5.5, H3'), 4.41-4.44 (1H, m, H4'), 4.38 (1H, ddd, $J_{5'-5''}$=11.7, J=4.3, 2.4, H5'), 4.24 (1H, ddd, $J_{5'-5''}$=11.7, J=5.3, 2.2, H5''), 4.13 (3H, s, $m^7$), 3.20 (1H, d, $J_{P\gamma-C2H}$=11.6, $H_{C2H}$); $^{31}$P NMR (162 MHz, $D_2O$, 25° C.) $\delta_P$: −10.58 (1P, br d, $J_{P\alpha-P\beta}$=22.0, P$\alpha$), −20.86 (1P, dd, $J_{P\gamma-P\beta}$=22.0, $J_{P\gamma-C2H}$=11.6, P$\beta$); HRMS (−) ESI m/z found: 464.0378, calc. for $C_{13}H_{16}N_5O_{10}P_2^-$: 464.0372.

γ-C-(2-Ethynyl) 7-Methylguanosine Triphosphate Ammonium Salt ($m^7GpppC_2H$)

Obtained according to GP B starting from γ-C-(2-ethynyl) guanosine triphosphate triethylammonium salt (10000 mOD, 0.828 mmol), $(CH_3)_2SO_4$ (0.785 mL, 8.278 mmol) and $CH_3COOH$ solution pH 4 (8.0 mL). The ion-exchange purification afforded 5569 mOD (0.488 mmol, 59%) of $m^7GpppC_2H$ triethylammonium salt. Additional HPLC purification of a fraction of obtained product gave $m^7GpppC_2H$ as ammonium salt.

$^1$H NMR (400 MHz, $D_2O$, 25° C.) $\delta_H$: 6.08 (1H, d, $J_{1'-2'}$=3.9, H1'), 4.70 (1H, dd, $J_{1'-2'}$=3.9, $J_{2'-3'}$=4.9, H2'), 4.54 (1H, dd, $J_{2'-3'}$=4.7, $J_{3'-4'}$=5.3, H3'), 4.41-4.44 (1H, m, H4'), 4.38 (1H, ddd, $J_{5'-5''}$=11.7, J=4.1, 2.5, H5'), 4.24 (1H, ddd, $J_{5'-5''}$=11.7, J=5.1, 2.0, H5''), 4.14 (3H, s, $m^7$), 3.18 (1H, d, J=12.9, $H_{C2H}$); $^{31}$P NMR (162 MHz, $D_2O$, 25° C.) $\delta_P$: −10.80 (1P, br d, $J_{P\alpha-P\beta}$=20.5, P$\alpha$), −21.02 (1P, dd, $J_{P\gamma-P\beta}$=20.5, $J_{P\gamma-C2H}$=11.7, P$\gamma$), −22.93 (1P, t, $J_{P\alpha-P\beta}$=$J_{P\beta-P\gamma}$=20.5, P$\beta$); HRMS (−) ESI m/z found: 544.0042, calc. for $C_{13}H_{17}N_5O_{13}P_3^-$: 544.0036.

β-C-(2-Ethynyl) 2'-O-Methylguanosine Diphosphate Triethylammonium Salt $m^{2'-O}GppC_2H$ Triethylammonium 2-ethynyl C-phosphonate (1.053 mmol, 0.35 M) was stirred in 3 mL DMF until complete dissolution. Then, 2'-O-methylguanosine 5'-monophosphate P-imidazolide sodium salt (4241 mOD, 0.35 mmol) along with $MgCl_2$ (268 mg, 2.8 mmol) were added and the mixture was stirred for 0.5 h at room temperature. The reaction was stopped by 10-fold dilution with water. The product was purified by ion-exchange chromatography on DEAE Sephadex A-25 and evaporated to dryness as described in General Information to afford 3647 mOD, (0.302 mmol, 86%) of $m^{2'-O}GppC_2H$ triethylammonium salt. Additional HPLC purification of a fraction of obtained product gave $m^{2'-O}GppC_2H$ as ammonium salt.

$^1$H NMR (500 MHz, Deuterium Oxide) δ 8.14 (s, 1H, H8), 5.93 (d, J=6.5 Hz, 1H, H1'), 4.85 (dd, J=6.5, 5.2 Hz, 1H, H2'), 4.59 (dd, J=5.2, 3.0 Hz, 1H, H3'), 4.40-4.35 (m, 1H, H4'), 4.28 (ddd, J=11.5, 6.0, 3.4 Hz, 1H, H5'), 4.22 (ddd, J=11.5, 4.9, 3.5 Hz, 1H), 3.18 (d, J=12.9 Hz, 1H, $H_{C2H}$); $^{31}$P NMR (202 MHz, Deuterium Oxide) δ −10.58 (dt, J=18.7, 6.0 Hz, 1P, P$\alpha$), −20.84 (dd, J=18.6, 12.9 Hz, 1P, P$\delta$), −22.53 (t, J=18.0 Hz, 1P, P$\beta$ or P$\gamma$), −23.04 (t, J=18.0 Hz, 1P, P$\beta$ or P$\gamma$); HRMS (−) ESI m/z found: 464.0379, calc. for $C_{13}H_{16}N_5O_{10}P_2^-$ 464.0378.

γ-C-(2-Ethynyl) 2'-O-Methylguanosine Triphosphate Triethylammonium Salt ($m^{2'-O}GpppC_2H$)

Triethylammonium 2-ethynyl C-phosphonate (1.698 mmol, 0.2 M) was stirred in 8.5 mL DMF until complete dissolution. Then, 2'-O-methylguanosine 5'-diphosphate β-P-imidazolide trisodium salt (6842 mOD, 0.566 mmol) along with $MgCl_2$ (431 mg, 4.531 mmol) were added and the mixture was stirred for 1 h at room temperature. The reaction was stopped by 10-fold dilution with water. The product was purified by ion-exchange chromatography on DEAE Sephadex A-25 and evaporated to dryness as described in General Information to afford 6385 mOD (0.528 mmol, 93%) of $m^{2'-O}GpppC_2H$ triethylammonium salt. Additional HPLC purification of a fraction of obtained product gave $m^{2'-O}GpppC_2H$ as ammonium salt.

$^1$H NMR (400 MHz, $D_2O$, 25° C.) $\delta_H$: 8.13 (1H, s, H8), 5.99 (1H, d, $J_{1'-2'}$=6.5, H1'), 4.74 (1H, dd, $J_{2'-3'}$=5.1, $J_{3'-4'}$=3.1, H3'), 4.56 (1H, dd, $J_{2'-3'}$=5.1, $J_{1'-2'}$=6.5, H2'), 4.36-4.39 (1H, m, H4'), 4.28 (1H, ddd, $J_{5'-5''}$=11.7, $J_{P\alpha-5'}$=5.9, $J_{4'-5'}$=3.5, H5'), 4.24 (1H, ddd, $J_{5'-5''}$=11.7, $J_{4'-5''}$=5.1, $J_{P\alpha-5''}$=3.4, H5''), 3.47 (3H, s, $m^{2'O}$), 3.18 (1H, d, $J_{C2H-P\gamma}$=13.1, $H_{C2H}$); $^{31}$P NMR (162 MHz, $D_2O$, 25° C.) $\delta_P$: −10.80 (1P, ddd, $J_{P\alpha-P\beta}$=20.5, $J_{P\alpha-5'}$=5.9, $J_{P\alpha-5''}$=3.4, P$\alpha$), −21.02 (1P, dd, $J_{C2H-P\gamma}$=13.1, $J_{P\beta-P\gamma}$=19.1, P$\gamma$), −22.99 (1P, dd, $J_{P\beta-P\gamma}$=10.1, $J_{P\alpha-P\beta}$=20.5, P$\beta$); HRMS (−) ESI m/z found: 544.0044, calc. for $C_{13}H_{17}N_5O_{13}P_3^-$: 544.0036.

β-C-(2-Ethynyl) 2'-O—N7-Dimethylguanosine Diphosphate Ammonium Salt ($m_2^{7,2'-O}GppC_2H$)

Obtained according to GP C starting from β-C-(2-ethynyl) 2'-O'methylguanosine diphosphate triethylammonium salt (3100 mOD, 0.257 mmol), $(CH_3)SO_4$ (0.292 mL, 3.08 mmol) and $CH_3COOH$ solution pH 4 (3.1 mL). The ion-exchange purification afforded 2180 mOD, (0.191 mmol, 74%) of $m_2^{7,2'-O}GppC_2H$ triethylammonium salt. Additional HPLC purification of a fraction of obtained product gave $m_2^{7,2'-O}GppC_2H$ as ammonium salt.

$^1$H NMR (500 MHz, Deuterium Oxide) δ 6.16 (d, J=3.5 Hz, 1H, H1'), 4.62 (t, J=4.9, 5.5 Hz, 1H, H3'), 4.41 (dd, J=4.9, 3.5 Hz, 1H, H2'), 4.40-4.38 (m, 1H, H4'), 4.36 (ddd, J=11.8, 4.3, 2.4 Hz, 1H, H5'), 4.23 (ddd, J=11.8, 5.2, 2.1 Hz, 1H, H5''), 4.13 (s, 3H, $m^7$), 3.60 (s, 3H, $m^{2'O}$), 3.19 (d, J=12.5 Hz, 1H, $C_2H$); $^{31}$P NMR (202 MHz, Deuterium Oxide) δ −11.00 (dt, J=22.1, 4.5 Hz, 1P, P$\alpha$), −20.80 (dd, J=22.1, 12.5 Hz, 1P, P$\beta$); HRMS (−) ESI m/z found: 478.0537, calc. for: $C_{14}H_{18}N_5O_{10}P_2^-$ 478.0534.

γ-C-(2-Ethynyl) 2'-O—N7-Dimethylguanosine Triphosphate Ammonium Salt ($m_2^{7,2'-O}GpppC_2H$)

Obtained according to GP C starting from γ-C-(2-ethynyl) 2'-O'methylguanosine triphosphate triethylammonium salt (5380 mOD, 0.445 mmol), $(CH_3)SO_4$ (0.422 mL, 4.454 mmol) and $CH_3COOH$ solution pH 4 (5.0 mL). The ion-exchange purification afforded 4014 mOD (0.352 mmol, 79%) of $m_2^{7,2'-O}GpppC_2H$ triethylammonium salt. Additional HPLC purification of a fraction of obtained product gave $m_2^{7,2'-O}GpppC_2H$ as ammonium salt.

$^1$H NMR (400 MHz, $D_2O$, 25° C.) $\delta_H$: 6.16 (1H, d, $J_{1'-2'}$=3.1, H1'), 4.65 (1H, dd, J=5.1, 5.5, H3'), 4.36-4.42 (3H, overlapped H2', H4' and H5'), 4.26 (1H, ddd, $J_{5'-5''}$=12.5, $J_{P\alpha-5'}$=4.8, $J_{4'-5''}$=2.7, H5''), 4.14 (3H, s, $m^7$), 3.61 (3H, s, $m^{2'O}$), 3.18 (1H, d, $J_{P\gamma-C2H}$=12.9, $H_{C2H}$); $^{31}$P NMR (162 MHz, $D_2O$, 25° C.) $\delta_P$: −10.80 (1P, ddd, $J_{P\alpha-P\beta}$=20.5, $J_{P\alpha\text{-}5'}$=7.3, $J_{P\alpha\text{-}5''}$=4.8, P$\alpha$), −21.05 (1P, dd, $J_{P\beta\text{-}P\gamma}$=19.1, $J_{P\gamma\text{-}C2H}$=12.9, P$\gamma$), −22.91 (1P, dd, $J_{P\beta\text{-}P\gamma}$=19.1, $J_{P\alpha\text{-}P\beta}$=20.5, P$\beta$); HRMS (−) ESI m/z found: 558.0200, calc. for $C_{14}H_{19}N_5O_{13}P_3^-$: 558.0192.

1.7. Synthesis of Phosphoramidate Nucleotide Analogues

General Procedure D (GP D): Coupling of Nucleotide Imidazolides with Amine Linker Compounds were synthesized analogously as described in Guranowski et al. for the reaction of diamine linkers with guanosine 5'-phosphorimidazolide.[41] An appropriate nucleotide imidazolide was dissolved in 0.1 M Tris-HCl buffer pH 8.0 (approx. 1 mL per 100 mg nucleotide) and propargylamine or 2-azidoethyloamine (8 equiv.) was added. The mixture was stirred at room temperature for 24 h. The reaction was diluted with ten volumes of water and washed with diethyl ether. After setting pH to 7 with 5% HCl, the aqueous phase was either subjected to ion-exchange chromatography purification as described in General Information to afford the desired product as triethylammonium salt or directly purified by semi-preparative HPLC to afford the desired product as ammonium salt.

1.7.1. Synthesis of Azide-Modified Phosphoramidate Nucleotide Analogues

N-(2-Azidoethyl) Phosphoramidate Guanosine Monophosphate Ammonium Salt (GpNHC$_2$H$_4$N$_3$)

Obtained according to GP D starting from guanosine 5'-monophosphate P-imidazolide sodium salt (200 mg, 4800 mOD, 0.397 mmol), 2-azidoethylamine (0.349 mL, 3.179 mmol) and 2.0 mL of Tris-HCl buffer. The ion-exchange purification afforded 4004 mOD (0.331 mmol, 83%) of GpNHC$_2$H$_4$N$_3$ triethylammonium salt. Additional HPLC purification of a fraction of obtained product gave GpNHC$_2$H$_4$N$_3$ as ammonium salt.

$^1$H NMR (400 MHz, D$_2$O, 25° C.) $\delta_H$: 8.11 (1H, s, H8), 5.93 (1H, d, $J_{1'\text{-}2'}$=5.9, H1'), 4.84 (1H, dd, $J_{1'\text{-}2'}$=5.9, $J_{2'\text{-}3'}$=5.1, H2'), 4.51 (1H, dd, $J_{2'\text{-}3'}$=5.1, $J_{3'\text{-}4'}$=3.9, H3'), 4.31-4.34 (1H, m, H4'), 4.04 (1H, ddd, $J_{5'\text{-}5''}$=11.7, J=4.7, 3.1, H5'), 4.00 (1H, ddd, $J_{5'\text{-}5''}$=11.7, J=5.1, 3.5), 3.24 (2H, br t, $J_{CH2(N3)\text{-}CH2(NH)}$=5.9, H$_{CH2(N3)}$), 2.89 (2H, dt, $J_{CH2(N3)\text{-}CH2(NH)}$=5.9, $J_{CH2(N3)\text{-}P\alpha}$=10.2, H$_{CH2(NH)}$); $^{31}$P NMR (162 MHz, D$_2$O, 25° C.) $\delta_P$: 9.37-9.55 (1P, m, P$\alpha$); HRMS (−) ESI m/z found: 430.0991, calc. for $C_{12}H_{17}N_9O_7P^-$: 430.0989.

N-(2-Azidoethyl) β-Phosphoramidate Guanosine Diphosphate Ammonium Salt (GppNHC$_2$H$_4$N$_3$)

Obtained according to GP D starting from guanosine 5'-diphosphate β-P-imidazolide disodium salt (458 mg, 8244 mOD, 0.682 mmol), 2-azidoethylamine (0.600 mL, 5.460 mmol) and 4.5 mL of Tris-HCl buffer. The ion-exchange purification afforded 7085 mOD (0.586 mmol, 86%) of GppNHC$_2$H$_4$N$_3$ triethylammonium salt. Additional HPLC purification of a fraction of obtained product gave GppNHC$_2$H$_4$N$_3$ as ammonium salt.

$^1$H NMR (400 MHz, D$_2$O, 25° C.) $\delta_H$: 8.12 (1H, s, H8), 5.93 (1H, d, $J_{1'\text{-}2'}$=6.3, H1'), 4.80 (1H, overlapped with HDO, H2'), 4.53 (1H, dd, J=3.7, 5.3, H3'), 4.33-4.36 (1H, m, H4'), 4.18-4.21 (1H, m, H5' and H5''), 3.32 (2H, br t, $J_{CH2(N3)\text{-}CH2(NH)}$=5.9, H$_{CH2(N3)}$), 3.03 (2H, dt, $J_{CH2(N3)\text{-}CH2(NH)}$=5.9, $J_{CH2(N3)\text{-}P\beta}$=10.4, H$_{CH2\text{-}NH}$); $^{31}$P NMR (162 MHz, D$_2$O, 25° C.) $\delta_P$: −1.04 (1P, dt, $J_{CH2(N3)\text{-}P\beta}$=10.4, $J_{P\alpha\text{-}P\beta}$=22.0, P$\beta$), −10.26 (1P, br d, $J_{P\alpha\text{-}P\beta}$=22.0, P$\alpha$); HRMS (−) ESI m/z found: 510.0657, calc. for $C_{12}H_{18}N_9O_{10}P_2^-$: 510.0652; hydrolysis in D$_2$O: 15%.

N-(2-Azidoethyl) Phosphoramidate 7-Methylguanosine Monophosphate Ammonium Salt (m$^7$GpNHC$_2$H$_4$N$_3$)

Obtained according to GP D starting from 7-methyl guanosine 5'-monophosphate P-imidazolide sodium salt (450 mg, 9900 mOD, 0.868 mmol), 2-azidoethylamine (0.764 mL, 6.944 mmol) and 4.5 mL of Tris-HCl buffer. The directly following HPLC purification afforded 3520 mOD of m$^7$GpNHC$_2$H$_4$N$_3$ (0.309 mmol, 36%) as ammonium salt.

$^1$H NMR (400 MHz, D$_2$O, 25° C.) $\delta_H$: 6.08 (1H, d, $J_{1'\text{-}2'}$=3.9, H1'), 4.68 (1H, dd, $J_{1'\text{-}2'}$=3.9, $J_{2'\text{-}3'}$=4.9, H2'), 4.48 (1H, dd, $J_{2'\text{-}3'}$=4.9, $J_{3'\text{-}4'}$=5.4, H3'), 4.38-4.41 (1H, m, H4'), 4.18 (1H, ddd, $J_{5'\text{-}5''}$=11.7, J=4.4, 2.4, H5'), 4.12 (3H, s, m$^7$), 4.06 (1H, ddd, $J_{5'\text{-}5''}$=11.7, J=4.9, 2.9, H5''), 3.35 (2H, t, $J_{CH2(N3)\text{-}CH2(NH)}$=5.9, H$_{CH2(N3)}$), 3.0 (2H, dt, $J_{CH2(N3)\text{-}CH2(NH)}$=5.9, $J_{P\alpha\text{-}CH2(NH)}$=10.3, H$_{CH2(NH)}$); $^{31}$P NMR (162 MHz, D$_2$O, 25° C.) $\delta_P$: 9.32-9.44 (1P, m, P$\alpha$); HRMS (−) ESI m/z found: 444.1146, calc. for $C_{13}H_{19}N_9O_7P^-$: 444.1145.

N-(2-Azidoethyl) β-Phosphoramidate 7-Methylguanosine Diphosphate Ammonium Salt (m$^7$GppNHC$_2$H$_4$N$_3$)

Obtained according to GP D starting from 7-methylguanosine 5'-diphosphate β-P-imidazolide disodium salt (238 mg, 3641 mOD, 0.319 mmol), 2-azidoethylamine (0.281 mL, 2.555 mmol) and 2.5 mL of Tris-HCl buffer. The ion-exchange purification afforded 1785 mOD (0.156 mmol, 49%) of m$^7$GppNHC$_2$H$_4$N$_3$ triethylammonium salt. Additional HPLC purification of a fraction of obtained product gave m$^7$GppNHC$_2$H$_4$N$_3$ as ammonium salt.

$^1$H NMR (400 MHz, D$_2$O, 25° C.) $\delta_H$: 6.08 (1H, d, $J_{1'\text{-}2'}$=3.5, H1'), 4.68 (1H, dd, $J_{1'\text{-}2'}$=3.5, $J_{2'\text{-}3'}$=4.7, H2'), 4.51 (1H, $J_{2'\text{-}3'}$=4.7, $J_{3'\text{-}4'}$=5.5, H3'), 4.39-4.42 (1H, m, H4'), 4.34 (1H, ddd, $J_{5'\text{-}5''}$=12.1, J=4.3, 2.4, H5'), 4.22 (1H, ddd, $J_{5'\text{-}5''}$=12.1, J=5.5, 2.4, H5''), 4.13 (3H, s, m$^7$), 3.41 (2H, t, $J_{CH2(N3)\text{-}CH2(NH)}$=5.9, H$_{CH2(N3)}$), 3.10 (2H, dt, $J_{CH2(N3)\text{-}CH2(NH)}$=5.9, $J_{CH2(NH)\text{-}P\beta}$=10.5, H$_{CH2(NH)}$); $^{31}$P NMR (162 MHz, D$_2$O, 25° C.) $\delta_P$: −0.82 (1P, dt, $J_{CH2\text{-}P\beta}$=10.5, $J_{P\alpha\text{-}P\beta}$=22.7, P$\beta$), −10.28 (1P, br d, $J_{P\alpha\text{-}P\beta}$=22.7, P$\alpha$); HRMS (−) ESI m/z found: 524.0819, calc. for $C_{13}H_{20}N_9O_{10}P_2^-$: 524.0808.

1.8 Synthesis of Azide-Containing Phosphoester Analogues

Azidoethyl Phosphate

H$_3$PO$_4$ (50 mg, 0.610 mmol, 1 equiv.) was added to a flask and dissolved in 2-azidoethanol (1.385 ml, 18.293 mmol, 30 equiv.). Then, TEA (253 µl, 1.819 mmol, 3 equiv.) was added and the mixture was stirred for 5 min. Next, iodine (308 mg, 1.22 mmol, 2 equiv.) was gradually added and the mixture was stirred for 96 h at room temperature. The product was precipitated upon addition of the mixture of 350 µl of cyclohexylamine in 15.8 mL acetone. The precipitate was filtered off, washed repeatedly with cold, dry acetone until it turned white and then dried in vacuum over P$_2$O$_5$.

$^{31}$P NMR (202 MHz, Deuterium Oxide) δ 4.10 (t, J=6.2 Hz).

2',3'-O,O-Isopropylideneguanosine H-Phosphonate 2'3'-iPr-GpH

2',3'-O,O-isopropylideneguanosine H-phosphonate was synthesized by stirring 2',3'-O,O-isopropylideneguanosine (1.010 g, 3.128 mmol, 1 equiv.) with PCl$_3$ (312 µl, 3.567 mmol, 1.1 equiv.) in the presence of 15.24 mL of trimethyl phosphate at 0° C. for 1 h. Then the mixture was diluted with approx. 150 ml of water and the pH was set to 7 using solid NaHCO$_3$. The ion-exchange purification afforded 17760 mOD, (1.470 mmol, 47%) of 2'3'-iPr-GpH triethylammonium salt.

O-(2-Azidoethyl) Guanosine Phosphate Ammonium Salt (GpOC$_2$H$_4$N$_3$)

To the flask containing 2'3'-iPr-GpH (3000 mOD, 0.248 mmol, 1 equiv.) BSA (607 µl, 2.48 mmol, 10 equiv.) and ACN (607 µl) were added. The mixture was stirred for 15 min after which TEA (102 µl, 0.744 mmol, 3 equiv.) along with 2-azidoethanol (564 µl, 7.44 mmol, 30 equiv.) were added and the stirring was continued for 5 min. Next, iodine (126 mg, 0.496 mmol, 2 equiv.) was gradually added and the reaction was stirred for 7 days at 45° C. After that, it was diluted with approx. 30 mL of water and the pH was set to 1.5 with conc. HCl. The resulting mixture was stirred at 60° C. for 1.5 h and then the pH was set to 7 with solid $NaHCO_3$. The mixture was subjected to ion-exchange purification which afforded 1350 mOD (0.112 mmol, 45%) of $GpOC_2H_4N_3$ triethylammonium salt. Additional HPLC purification of a fraction of obtained product gave $GpOC_2H_4N_3$ as ammonium salt.

$^1$H NMR (500 MHz, Deuterium Oxide) δ 8.20 (s, 1H, H8), 5.95 (d, J=5.4 Hz, 1H, H1'), 4.81 (dd, J=5.3, 5.4 Hz, 1H, H2', overlapped with HDO), 4.52 (dd, J=5.2, 4.0 Hz, 1H, H3'), 4.34-4.36 (m, 1H, H4'), 4.20-4.08 (m, 2H, H5', H5"), 3.98-3.88 (m, 2H, $CH_2$—$N_3$), 3.46-3.36 (m, 2H, $CH_2$—O); $^{31}$P NMR (202 MHz, Deuterium Oxide) δ 0.94-1.05 (m, 1P, Pα); HRMS (−) ESI m/z found: 431.06262, calc. for: $C_{12}H_{16}N_8O_8P$−431.0834196(2).

β-O-(2-Azidoethyl) Guanosine Diphosphate Ammonium Salt ($GppOC_2H_4N_3$)

DMF (3.7 mL) and $MgCl_2$ (74.2 mg, 0.78 mmol, 4 equiv.) were added to a flask with dry azidoethyl phosphate cyclohexylammonium salt (ca. 0.610 mmol, 3 equiv.) and the mixture was stirred at room temperature until complete dilution of the phosphate subunit. Then, guanosine 5'-monophosphate imidazolide (106 mg, 2353 mOD, 0.195 mmol, 1 equiv.) along with second portion of $MgCl_2$ (74.2 mg, 0.78 mmol, 4 equiv.) were added. The mixture was stirred at room temperature for 24 h. The reaction was then stopped by diluting with ten volumes of water and subjected to ion-exchange purification which afforded 2047 mOD, (0.170 mmol, 87%) of $GppOC_2H_4N_3$ triethylammonium salt. Additional HPLC purification of a fraction of obtained product gave $GppOC_2H_4N_3$ as ammonium salt.

$^1$H NMR (500 MHz, Deuterium Oxide) δ 8.35 (s, 1H, H8), 5.97 (d, J=5.5 Hz, 1H, H1'), 4.78 (dd, J=5.1, 5.5 Hz, 1H, H2'), 4.53 (dd, J=5.1, 3.9 Hz, 1H, H3'), 4.37 (dt, J=3.9, 2.3 Hz, 1H, H4'), 4.30-4.18 (m, 2H, H5' and H5"), 4.06-4.09 (m, 2H, $CH_{2linker\ CH2-O}$), 3.48 (t, J=5.0 Hz, 2H, $CH_{2linker\ CH2-N3}$); $^{31}$P NMR (202 MHz, Deuterium Oxide) δ −10.57-−10.30 (m, 2P, overlapped Pα and Pβ); HRMS (−) ESI m/z found: 511.0503, calc. for: $C_{12}H_{17}N_8O_{11}P_2^-$ 511.0498.

1.9. Synthesis of Dinucleotide Cap Analogues

General Procedure G (GP G): Synthesis of Dinucleotide Cap Analogues Containing Triazole Located Between P-Subunits (Phosphoramidate Analogues)

Aqueous solutions of an alkyne-containing nucleotide (1 equiv., 0.2-1.0 M) and an azide-containing nucleotide (1 equiv., 0.2-1.0 M) were mixed together followed by addition of $H_2O$ (to the concentration of each analogue ca. 50-150 mM) and aqueous solutions of $CuSO_4.5H_2O$ (0.2 equiv., 0.5-6.0 M) and sodium ascorbate (0.4 equiv., 1-12 M). The reaction was stirred at room temperature for several hours and monitored by RP HPLC. Additional portions of $CuSO_4$ or sodium ascorbate solutions were added upon slow kinetics. Final concentrations of reagents are given in the detailed procedures below. When completed, the reaction was quenched by 5-fold dilution with water and addition of $Na_2EDTA$ (ten equivalents of added $CuSO_4$) directly followed by semi-preparative RP HPLC purification.

General Procedure G (GP H): Synthesis of Dinucleotide Cap Analogues Containing Triazole Located Between P-Subunits (Phosphorester Analogues)

Aqueous solutions of an alkyne-containing nucleotide (1 equiv., 0.2-0.5 M) and an azide-containing nucleotide (1 equiv., 0.2-0.5 M) were mixed together followed by addition of $H_2O$ and the mixture of $H_2O$:t-BuOH (1:1, v/v) (to the concentration of each analogue ca. 26-53 mM, final $H_2O$:t-BuOH (2-5:1, v/v)) and aqueous solutions of $CuSO_4.5H_2O$ (0.4 equiv., 0.6-0.65 M) and sodium ascorbate (0.8 equiv., 1.2-1.3 M). The reaction was stirred at room temperature for 0.5-1 h and monitored by RP HPLC. Final concentrations of reagents are given in the detailed procedures below. When completed, the reaction was quenched by 5-fold dilution with water and addition of $Na_2EDTA$ (ten equivalents of added $CuSO_4$) directly followed by semi-preparative RP HPLC purification.

$m^7GpNHC_2H_4$-Triazole-$CH_2$ppG

Obtained according to GP G from $GppC_3H_3$ (848 mOD, 0.070 mmol, 150 mM) and $m^7GpNHC_2H_4N_3$ (800 mOD, 0.070 mmol, 150 mM) while stirring with $CuSO_4$ (3.5 mg, 0.014 mmol, 30 mM) and sodium ascorbate (5.5 mg, 0.028 mmol, 60 mM) in 0.70 mL of $H_2O$ for 1 h. After quenching the reaction with $Na_2EDTA$ (52.2 mg, 0.14 mmol), the product was subjected to RP HPLC purification which afforded $m^7GpNHC_2H_4$-triazole-$CH_2$ppG as ammonium salt.

$^1$H NMR (400 MHz, $D_2O$, 25° C.) $δ_H$: 8.03 (1H, s, H8 G), 7.84 (1H, s, J=2.0, $H_{triazole}$), 5.98 (1H, d, $J_{1'-2'}$=3.9, H1' $m^7G$), 5.88 (1H, d, $J_{1'-2'}$=5.9, H1' G), 4.77 (1H, dd, $J_{1'-2'}$=5.9, $J_{2'-3'}$=5.1, H2' G), 4.69 (1H, dd, $J_{1'-2'}$=3.9, $J_{2'-3'}$=5.1, H2' $m^7G$), 4.50 (1H, dd, $J_{2'-3'}$=5.1, $J_{3'-4'}$=3.9, H3' G), 4.42 (1H, dd, $J_{2'-3'}$=5.1, $J_{3'-4'}$=5.5, H3' $m^7G$), 4.37 (2H, br t, $J_{CH2(triazole)m7G-CH2(NH)}$=6.1, $H_{CH2(triazole)m7G}$), 4.31-4.34 (2H, m, overlapped H4' G and $m^7G$), 4.14-4.21 (2H, m, H5' and H5" G), 4.00 (1H, ddd, $J_{5'-5''}$=11.7, J=4.7, 2.7, H5' $m^7G$), 3.90 (1H, ddd, $J_{5'-5''}$=11.7, J=4.9, 3.3, H5" $m^7G$), 3.23-3.28 (2H, m, $H_{CH2(NH)}$), 3.16 (2H, d, $J_{Pβ-CH2(P)}$=20.2, $H_{CH2(P)}$); $^{31}$P NMR (162 MHz, $D_2O$, 25° C.) $δ_P$: 11.70 (1P, dt, $J_{Pβ-CH2(P)}$=20.2, $J_{Pα-Pβ}$26.4, Pβ), 9.01-9.14 (1P, m, Pδ), −10.40 (1P, br d, $J_{Pα-Pβ}$=26.4, Pα); HRMS (−) ESI m/z found: 909.1618, calc. for $C_{26}H_{36}N_{14}O_{17}P_3^-$: 909.1596; hydrolysis in $D_2O$: 11%.

m'$GpNHC_2H_4$-Triazole-$CH_2$pppG

Obtained according to GP G from $GpppC_3H_3$ (742 mOD, 0.061 mmol, 150 mM) and $m^7GpNHC_2H_4N_3$ (700 mOD, 0.061 mmol, 150 mM) while stirring with $CuSO_4$ (3.0 mg, 0.012 mmol, 30 mM) and sodium ascorbate (4.8 mg, 0.024 mmol, 60 mM) in 0.409 mL of $H_2O$ for 1 h. After quenching the reaction with $Na_2EDTA$ (44.7 mg, 0.12 mmol), the product was subjected to RP HPLC purification which afforded $m^7GpNHC_2H_4$-triazole-$CH_2$pppG as ammonium salt.

$^1$H NMR (400 MHz, $D_2O$, 25° C.) δH: 8.06 (1H, s, H8 G), 7.88 (1H, d, J=2.0, $H_{triazole}$), 5.98 (1H, d, $J_{1'-2'}$=3.9, H1' $m^7G$), 5.86 (1H, d, $J_{1'-2'}$=6.3, H1' G), 4.79 (1H, dd, $J_{1'-2'}$=6.3, $J_{2'-3'}$=5.1, H2' G), 4.74 (1H, dd, $J_{1'-2'}$=3.9, $J_{2'-3'}$=5.1, H2' $m^7G$), 4.54 (1H, dd, $J_{2'-3'}$=5.1, $J_{3'-4'}$=3.5, H3' G), 4.37 (1H, dd, $J_{2'-3'}$=5.1, $J_{2'-3'}$=5.1, H3' $m^7G$), 4.37 (2H, br t, $J_{CH2(triazole)m7G-CH2(NH)}$=6.6, $H_{CH2(triazole)m7G}$), 4.32-4.35 (2H, overlapped H4' G and H4' $m^7G$ and H5' G), 4.28 (1H, ddd, $J_{5'-5''}$=11.7, J=5.3, 3.3, H5' $m^7G$), 4.23 (1H, ddd, $J_{5'-5''}$=11.7, J=5.9, 3.9, H5" $m^7G$), 4.06 (3H, s, $m^7$), 4.02 (1H, ddd, $J_{5'-5''}$=11.7, J=4.7, 2.7, H5' G), 3.86 (1H, ddd, $J_{5'-5''}$=11.7, J=5.1, 3.5, H5" G), 3.21-3.26 (2H, m, $H_{CH2(NH)}$), 3.22 (2H, d, $J_{CH2(P)-Pγ}$=20.4, $H_{CH2(P)}$); $^{31}$P NMR (162 MHz, $D_2O$, 25° C.) $δ_P$: 14.20 (1P, dt, $J_{Pβ-Pγ}$=24.9, $J_{P\gamma\text{-}CH2(P)}$=20.4, Pγ), 11.20-11.32 (1P, m, Pε), −8.35 (1P, dt, $J_{P\alpha\text{-}P\beta}$=19.1 $J_{P\alpha\text{-}5'/5''}$=4.4, Pα), 20.05 (1P, $J_{P\alpha\text{-}P\beta}$=19.1, $J_{P\beta\text{-}P\gamma}$=24.9, Pβ); HRMS (−) ESI m/z found: 989.1276, calc. for $C_{26}H_{37}N_{14}O_{20}P_4^-$: 989.1259; hydrolysis in $D_2O$: 7%.

m⁷GppCH₂-Triazole-C₂H₄NHpG

Obtained according to GP G from m⁷GppC₃H₃ (1132 mOD, 0.099 mmol, 150 mM) and GpNHC₂H₄N₃ (1200 mOD, 0.099 mmol, 150 mM) while stirring with CuSO₄ (4.9 mg, 0.020 mmol, 30 mM) and sodium ascorbate (7.9 mg, 0.040 mmol, 60 mM) in 0.662 mL of H₂O for 2 h. After quenching the reaction with Na₂EDTA (74.5 mg, 0.20 mmol), the product was subjected to RP HPLC purification which afforded m⁷GppCH₂-triazole-C₂H₄NHpG as ammonium salt.

¹H NMR (400 MHz, D₂O, 25° C.) $\delta_H$: 8.01 (1H, s, H8 G), 7.82 (1H, d, J=2.0, $H_{triazole}$), 6.02 (1H, d, $J_{1'\text{-}2'}$=3.5, H1' m⁷G), 5.86 (1H, d, $J_{1'\text{-}2'}$=5.5, H1' G), 4.83 (1H, dd, $J_{1'\text{-}2'}$=5.5, $J_{2'\text{-}3'}$=5.5, H2'G), 4.68 (1H, dd, $J_{1'\text{-}2'}$=3.5, $J_{2'\text{-}3'}$=4.7, H2' m⁷G), 4.46 (2H, overlapped H3' G and m⁷G), 4.35-4.37 (1H, m, H4' G or m⁷G), 4.28-4.31 (3H, overlapped H4' G or m⁷G, $H_{CH2(triazole)G'}$), 4.24 (1H, ddd, $J_{5'\text{-}5''}$=11.7, J=4.3, 2.4, H5' G or m⁷G), 4.16 (1H, ddd, $J_{5'\text{-}5''}$=11.7, J=5.5, 2.4, H5'' G or m⁷G), 4.08 (3H, s, m⁷), 3.96 (1H, ddd, $J_{5'\text{-}5''}$=11.7, J=4.7, 3.1, H5'' G or m⁷G), 3.88-3.93 (1H, m, H5'' G or m⁷G), 3.22 (2H, d, $J_{CH2(P)\text{-}P\gamma}$=20.5, $H_{CH2(P)}$), 3.13-3.20 (2H, m, $H_{CH2(NH)}$); ³¹P NMR (162 MHz, D₂O, 25° C.) $\delta_P$: 11.95 (1P, dt, $J_{P\gamma\text{-}CH2(P)}$=20.5, $J_{P\gamma\text{-}P\delta}$=26.4, Pγ), 9.05-9.18 (1P, m, Pα), −10.34 (1P, br d, $J_{P\alpha\text{-}P\beta}$=26.4, Pδ); HRMS (−) ESI m/z found: 909.1603, calc. for $C_{26}H_{36}N_{14}O_{17}P_3^-$: 909.1596.

m⁷GpppCH₂-Triazole-C₂H₄NHpG

Obtained according to GP G from m⁷GpppC₃H₃ (742 mOD, 0.061 mmol, 100 mM) and GpNHC₂H₄N₃ (700 mOD, 0.061 mmol, 100 mM) while stirring with CuSO₄ (6.0 mg, 0.024 mmol, 40 mM) and sodium ascorbate (9.6 mg, 0.048 mmol, 80 mM) in 0.614 mL of H₂O for 24 h. After quenching the reaction with Na₂EDTA (89.4 mg, 0.24 mmol), the product was subjected to RP HPLC purification which afforded m⁷GpppCH₂-triazole-C₂H₄NHpG as ammonium salt.

¹H NMR (400 MHz, D₂O, 25° C.) $\delta_H$: 8.00 (1H, s, H8 G), 7.84 (1H, d, $J_{CH2(P)\text{—}H(triazole)}$=2.2, $H_{triazole}$), 6.00 (1H, d, $J_{1'\text{-}2'}$=3.5, H1' m⁷G), 5.86 (1H, d, $J_{1'\text{-}2'}$=5.5, H1' G), 4.89 (1H, dd, $J_{1'\text{-}2'}$=5.5, $J_{2'\text{-}3'}$=5.1, H2' G), 4.69 (1H, dd, $J_{1'\text{-}2'}$=3.5, $J_{2'\text{-}3'}$=5.1, H2' m⁷G), 4.56 (1H, dd, $J_{2'\text{-}3'}$=5.1, $J_{3'\text{-}4'}$=5.5, H3' m⁷G), 4.47 (1H, dd, $J_{2'\text{-}3'}$=5.1, $J_{2'\text{-}3'}$=4.3, H3' G), 4.36-4.41 (2H, overlapped H4' and H5' m⁷G), 4.23-4.30 (4H, overlapped H5'' m⁷G, H4'G, $H_{CH2(triazole)G}$), 4.08 (3H, s, m⁷), 3.98 (1H, ddd, $J_{5'\text{-}5''}$=11.7, J=4.3, 2.9, H5'G), 3.89-3.95 (1H, m, H5'' G), 3.26 (2H, dd, $J_{CH2\text{-}P\gamma}$=20.5, $J_{CH2(P)\text{—}H(triazole)}$=2.2, $H_{CH2(P)}$), 3.07-3.18 (2H, m, $H_{CH2(NH)}$); ³¹P NMR (162 MHz, D₂O, 25° C.) $\delta_P$: 14.11 (1H, dt, $J_{P\gamma\text{-}P\delta}$=24.9, $J_{CH2(P)\text{—}P\gamma}$=20.5, Pγ), 11.18-11.37 (1P, m, Pα), −8.40 (1P, br d, $J_{P\epsilon\text{-}P\delta}$=19.1, Pε), −19.96 (1P, dd, $J_{P\epsilon\text{-}P\delta}$=19.1, $J_{P\gamma\text{-}P\delta}$=24.9, Pδ); HRMS (−) ESI m/z found: 494.0598, calc. for $C_{26}H_{36}N_{14}O_{20}P_4^{2-}$: 494.0590; hydrolysis in $D_2O$: 9%.

m⁷GpNHC₂H₄-Triazole-ppG

Obtained according to GP G from GpppC₃H₃ (700 mOD, 0.061 mmol, 100 mM) and m⁷GpNHC₂H₄N₃ (742 mOD, 0.061 mmol, 100 mM) while stirring with CuSO₄ (6.0 mg, 0.024 mmol, 40 mM) and sodium ascorbate (9.6 mg, 0.048 mmol, 80 mM) in 0.614 mL of H₂O for 1 h. After quenching the reaction with Na₂EDTA (89.4 mg, 0.24 mmol), the product was subjected to RP HPLC purification which afforded m⁷GpNHC₂H₄-triazole-ppG as ammonium salt.

¹H NMR (400 MHz, D₂O, 25° C.) $\delta_H$: 8.25 (1H, s, H8 G or $H_{triazole}$), 7.94 (1H, s, H8 G or $H_{triazole}$), 5.98 (1H, d, $J_{1'\text{-}2'}$=3.9, H1' m⁷G), 5.83 (1H, d, $J_{1'\text{-}2'}$=5.9, H1' G), 4.66 (1H, dd, $J_{1'\text{-}2'}$=5.9, $J_{2'\text{-}3'}$=5.1, H2' G), 4.62 (1H, dd, $J_{1'\text{-}2'}$=3.9, $J_{2'\text{-}3'}$=5.1, H2' m⁷G), 4.42-4.46 (3H, overlapped $H_{CH2(triazole)m7G'}$ and $H3'G$), 4.37 (1H, dd, $J_{2'\text{-}3'}$=5.1, $J_{3'\text{-}4'}$=5.1, H3' m⁷G), 4.29-4.32 (1H, m, H4' m⁷G), 4.25-4.28 (1H, m, H4' G), 4.13-4.15 (2H, m, H5' and H5'' G), 4.06 (3H, s, m⁷), 3.92 (1H, ddd, $J_{5'\text{-}5''}$=11.7, J=4.7, 2.7, H5' m⁷G), 3.82 (1H, ddd, $J_{5'\text{-}5''}$=11.7, J=5.1, 3.1, H5' m⁷G), 3.25-3.31 (2H, m, $H_{CH2(NH)}$); ³¹P NMR (162 MHz, D₂O, 25° C.) $\delta_P$: 8.92-9.04 (1P, m, Pδ), −6.87 (1P, d, $J_{P\alpha\text{-}P\beta}$=22.7, Pβ), −10.80 (1P, dt, $J_{P\alpha\text{-}P\beta}$=22.7, $J_{P\alpha\text{-}5'/5''}$=6.6, Pα); HRMS (−) ESI m/z found: 895.1456, calc. for $C_{25}H_{34}N_{14}O_{17}P_3^-$: 895.1439; hydrolysis in $D_2O$: 14%.

m⁷GpNHC₂H₄-Triazole-pppG

Obtained according to GP G from GpppC₂H (700 mOD, 0.061 mmol, 100 mM) and m⁷GpNHC₂H₄N₃ (742 mOD, 0.061 mmol, 100 mM) while stirring with CuSO₄ (6.0 mg, 0.024 mmol, 40 mM) and sodium ascorbate (9.6 mg, 0.048 mmol, 80 mM) in 0.614 mL of H₂O for 2.5 h. After quenching the reaction with Na₂EDTA (89.4 mg, 0.24 mmol), the product was subjected to RP HPLC purification which afforded m⁷GpNHC₂H₄-triazole-pppG as ammonium salt.

¹H NMR (400 MHz, D₂O, 25° C.) $\delta_H$: 8.30 (1H, s, H8 G or $H_{triazole}$), 7.03 (1H, s, H8 G or $H_{triazole}$), 5.98 (1H, d, $J_{1'\text{-}2'}$=3.7, H1' m⁷G), 5.85 (1H, d, $J_{1'\text{-}2'}$=6.3, H1' G), 4.73 (1H, dd, $J_{1'\text{-}2'}$=6.3, $J_{2'\text{-}3'}$=5.1, H2' G), 4.66 (1H, dd, $J_{1'\text{-}2'}$=3.7, $J_{2'\text{-}3'}$=4.7, H2' m⁷G), 4.48 (1H, dd, $J_{2'\text{-}3'}$=5.1, $J_{3'\text{-}4'}$=3.5, H3' G), 4.45 (2H, br t, $J_{CH2(triazole)m7G\text{-}CH2(NH)}$=5.9, $H_{CH2(triazole)m7G}$), 4.38 (1H, dd, $J_{2'\text{-}3'}$=4.7, $J_{3'\text{-}4'}$=5.9, H3' m⁷G), 4.31-4.34 (1H, m, H4' m⁷G), 4.27-4.30 (1H, m, H4' G), 4.14-4.16 (2H, m, H5' and H5'' G), 4.06 (3H, s, m⁷), 3.96 (1H, ddd, $J_{5'\text{-}5''}$=11.7, J=4.7, 2.7, H5' m⁷G), 3.84 (1H, ddd, $J_{5'\text{-}5''}$=11.7, J=5.1, 3.5, H5' m⁷G), 3.29 (1H, dt, $J_{CH2(triazole)\text{-}CH2(NH)}$=5.9, $J_{CH2(NH)\text{—}P\epsilon}$=10.6, $H_{CH2(NH)'}$ and $H_{CH2(NH)''}$); ³¹P NMR (162 MHz, D₂O, 25° C.) $\delta_P$: 8.94-9.12 (1P, m, Pε), −6.56 (1P, d, $J_{P\beta\text{-}P\gamma}$=22.0, Pγ), −10.61 (1P, dt, $J_{P\alpha\text{-}P\beta}$=19.1, $J_{P\alpha\text{-}5'/5''}$=5.1, Pα), −22.49 (1p, dd, $J_{P\alpha\text{-}P\beta}$=22.7, $J_{P\alpha\text{-}P\beta}$=19.1, Pβ); HRMS (−) ESI m/z found: 975.1124, calc. for $C_{25}H_{35}N_{14}O_{20}P_4^-$: 975.1103; hydrolysis in $D_2O$: 9%.

m⁷Gpp-Triazole-C₂H₄NHpG

Obtained according to GP G from m⁷GppC₂H (742 mOD, 0.061 mmol, 100 mM) and GpNHC₂H₄N₃ (700 mOD, 0.061 mmol, 100 mM) while stirring with CuSO₄ (6.0 mg, 0.024 mmol, 40 mM) and sodium ascorbate (9.6 mg, 0.048 mmol, 80 mM) in 0.614 mL of H₂O for 2 h. After quenching the reaction with Na₂EDTA (89.4 mg, 0.24 mmol), the product was subjected to RP HPLC purification which afforded m⁷Gpp-triazole-C₂H₄NHpG as ammonium salt.

¹H NMR (400 MHz, D₂O, 25° C.) $\delta_H$: 8.24 (1H, s, H8 G or $H_{triazole}$), 8.03 (1H, s, H8 G or $H_{triazole}$), 5.99 (1H, d, $J_{1'\text{-}2'}$=3.3, H1' m⁷G), 5.84 (1H, d, $J_{1'\text{-}2'}$=5.9, H1' G), 4.75 (1H, dd, $J_{1'\text{-}2'}$=5.9, $J_{2'\text{-}3'}$=5.1, H2' G), 4.64 (1H, dd, $J_{1'\text{-}2'}$=3.3, $J_{2'\text{-}3'}$=4.7, H2' m⁷G), 4.41-4.45 (2H, overlapped with H3' G and H3' m⁷G), 4.39 (2H, br t, $J_{CH2(triazole)G\text{-}CH2(NH)}$=6.3, $H_{CH2(triazole)G}$), 4.34-4.36 (1H, m, H4' m⁷G), 4.24-4.29 (2H, m, overlapped H5' m⁷G and H4' G), 4.18 (1H, ddd, $J_{5'\text{-}5''}$=11.9, J=5.5, 2.3, H5'' m⁷G), 4.04 (3H, s, m⁷), 3.90 (1H, ddd, J=$J_{5'\text{-}5''}$=11.7, J=4.5, 2.9, H5' G), 3.77-3.83 (1H, m, H5'' G), 3.17-3.28 (2H, m, $H_{CH2(NH)}$); ³¹P NMR (162 MHz, D₂O, 25° C.) $\delta_P$: 8.93-9.1 (1P, m, Pα), −6.62 (1P, d, $J_{P\gamma\text{-}P\beta}$23.5, Pγ), −10.75 (1P, br d, $J_{P\gamma\text{-}P\delta}$=23.5, Pδ); HRMS (−) ESI m/z found: 895.1454, calc. for $C_{25}H_{34}N_{14}O_{17}P_3^-$: 895.1439.

m⁷Gppp-Triazole-C₂H₄NHpG

Obtained according to GP G from m⁷GpppC₂H (742 mOD, 0.061 mmol, 50 mM) and GpNHC₂H₄N₃ (700 mOD, 0.061 mmol, 50 mM) while stirring with CuSO₄ (6.0 mg, 0.024 mmol, 20 mM) and sodium ascorbate (9.6 mg, 0.048 mmol, 40 mM) in 1.228 mL of H$_2$O for 1 h. After quenching the reaction with Na$_2$EDTA (89.4 mg, 0.24 mmol), the product was subjected to RP HPLC purification which afforded m$^7$Gppp-triazole-C$_2$H$_4$NHpG as ammonium salt.

$^1$H NMR (400 MHz, D$_2$O, 25° C.) δ$_H$: 8.23 (1H, s, H8 G or H$_{triazole}$), 8.02 (1H, s, H8 G or H$_{triazole}$), 6.00 (1H, d, J$_{1'-2'}$=3.5, H1' m$^7$G), 5.86 (1H, d, J$_{1'-2'}$=5.5, H1' G), 4.84 (1H, dd, J$_{1'-2'}$=5.5, J$_{2'-3'}$=5.1, H2' G), 4.66 (1H, dd, J$_{1'-2'}$=3.5, J$_{2'-3'}$=4.7, H2' m$^7$G), 4.51 (1H, dd, J$_{2'-3'}$=4.7, J$_{3'-4'}$=5.5, H3' m$^7$G), 4.44 (1H, dd, J$_{2'-3'}$=5.1, J$_{2'-3'}$=3.9, H3' G), 4.27-4.37 (5H, overlapped H4' G and H4' m$^7$G and H5' G or m$^7$G, H$_{CH2(triazole)}$), 4.20 (1H, ddd, J$_{5'-5''}$=11.7, J=5.5, 2.4, H5'' G or m$^7$G), 4.07 (3H, s, m$^7$), 3.94 (1H, ddd, J$_{5'-5''}$=11.5, J=4.3, 3.1, H5' m$^7$G or G), 3.84-3.89 (1H, m, H5' m$^7$G or G), 3.13-3.24 (2H, m, H$_{CH2(NH)}$); $^{31}$P NMR (162 MHz, D$_2$O, 25° C.) δ$_P$: 11.0.8-11.21 (1P, m, Pα), −4.38 (1P, d, J$_{Pβ-Pγ}$=22.0, Pγ), −8.41 (1P, br d, J$_{Pα-Pβ}$=19.1, Pε), −20.26 (1p, dd, J$_{Pα-Pβ}$=22.0, J$_{Pα-Pβ}$=19.1, Pγ); HRMS (−) ESI m/z found: 975.1122, calc. for C$_{25}$H$_{35}$N$_{14}$O$_{20}$P$_4$$^-$: 975.1103; hydrolysis in D$_2$O: 13%.

m$_2$$^{7,2'-O}$Gppp-Triazole-C$_2$H$_4$NHpG

Obtained according to GP G from m$_2$$^{7,2'-O}$GpppC$_2$H (650 mOD, 0.057 mmol, 100 mM) and GpNHC$_2$H$_4$N$_3$ (689 mOD, 0.061 mmol, 50 mM) while stirring with CuSO$_4$·5H$_2$O (2.7 mg, 0.011 mmol, 20 mM) and sodium ascorbate (4.4 mg, 0.022 mmol, 40 mM) in 0.570 mL of H$_2$O:t-BuOH (2:1, v/v) for 2 h. After quenching the reaction with Na$_2$EDTA (89.4 mg, 0.24 mmol), the product was subjected to RP HPLC purification which afforded m$_2$$^{7,2'-O}$Gppp-triazole-C$_2$H$_4$NHpG as ammonium salt.

$^1$H NMR (400 MHz, D$_2$O, 25° C.) δ$_H$: 9.14 (1H, q, J$_{H8-m7}$=0.8, H8 m$^7$G), 8.24 (1H, s, H8 G or H$_{triazole}$), 8.02 (1H, s, H8 G or H$_{triazole}$), 6.06 (1H, d, J$_{1'-2'}$=2.7, H1' m$^7$G), 5.84 (1H, d, J$_{1'-2'}$=5.5, H1' G), 4.80 (1H, overlapped with HDO, H2' G), 4.58 (1H, dd, J=6.2, 4.7, H3' m$^7$G), 4.42 (1H, dd, J=5.1, 3.9, H3' G), 4.27-4.36 (6H, overlapped H2'm$^7$G, H4' G and m$^7$G, H5' G or m$^7$G, H$_{CH2(triazole)}$), 4.18 (1H, ddd, J$_{5'-5''}$=12.3, J=5.3, 2.7, H5'' G or m$^7$G), 4.06 (3H, d, J$_{H8-m7}$=0.8, m$^7$), 3.92 (1H, ddd, J$_{5'-5''}$=11.7, J=4.3, 3.1, H5' G or m$^7$G), 3.84 (1H, ddd, J$_{5'-5''}$=11.7, J=5.1, 4.7), 3.59 (3H, s, m$^{2'O}$), 3.12-3.26 (2H, m, H$_{CH2(NH)}$); $^{31}$P NMR (162 MHz, D$_2$O, 25° C.) δ$_P$: 8.95-9.15 (1P, m, Pα), −6.57 (1P, d, J$_{Pγ-Pδ}$=21.3, Pγ), −10.64 (1P, ddd, J$_{Pε-Pδ}$=19.1, J$_{Pε-5}$=4.4, J$_{Pε-5''}$=2.9, Pε), −22.42 (1P, dd, J$_{Pγ-Pδ}$=21.3, J$_{Pε-Pδ}$=19.1, Pδ); HRMS (−) ESI m/z found: 989.1272, calc. for C$_{26}$H$_{37}$N$_{14}$O$_{20}$P$_4$$^-$: 989.1259; hydrolysis in D$_2$O: 8%.

m$^7$GppNHC$_2$H$_4$-Triazole-C$_2$H$_4$ppG

Obtained according to GP G from GppC$_4$H$_5$ (580 mOD, 0.048 mmol, 100 mM) and m$^7$GppNHC$_2$H$_4$N$_3$ (437 mOD, 0.038 mmol, 80 mM) while stirring with CuSO$_4$ (4.8 mg, 0.019 mmol, 40 M) and sodium ascorbate (7.5 mg, 0.038 mmol, 80 mM) in 0.485 mL of H$_2$O for 0.5 h. After quenching the reaction with Na$_2$EDTA (0.7 mg, 0.19 mmol), the product was subjected to RP HPLC purification which afforded m$^7$GppNHC$_2$H$_4$-triazole-C$_2$H$_4$ppG as ammonium salt.

$^1$H NMR (400 MHz, D$_2$O, 25° C.) δ$_H$: 9.16 (1H, s, H8 m$^7$G), 8.06 (1H, s, H8 G or H$_{triazole}$), 7.71 (1H, s, H8 G or H$_{triazole}$), 6.00 (1H, d, J$_{1'-2'}$=2.7, H1' G or m$^7$G), 5.88 (1H, d, J$_{1'-2'}$=5.5, H1' G or m$^7$G), 4.80 (1H, overlapped with HDO, H2' G or m$^7$G), 4.69 (2H, dd, J$_{1'-2'}$=2.7, J$_{3'-4'}$=5.1, H2' G or m$^7$G), 4.49-4.54 (2H, overlapped H3' G and m$^7$G), 4.35-4.39 (4H, overlapped H4' G and m$^7$G, H$_{CH2(triazole)m7G}$), 4.18-4.33 (4H, overlapped H5' and H5''G and m$^7$G), 4.06 (3H, s, m$^7$), 3.30 (2H, dt, J$_{CH2(NH)—Pδ}$=11.9, J$_{CH2(NH)—CH2(triazole)m7G}$=6.5, H$_{CH2(NH)}$), 2.78 (2H, m, H$_{CH2(triazole)G}$ or H$_{CH2(P)}$), 1.99 (2H, m, H$_{CH2(triazole)G}$ or H$_{CH2(P)}$); $^{31}$P NMR (162 MHz, D$_2$O, 25° C.) δ$_P$: 17.61-18.01 (1P, m, Pβ), −1.54 (1P, dt, J$_{Pδ-Pε}$=21.3, J$_{Pδ-CH2(NH)}$=11.9, Pδ), −10.27 (1P, br d, J$_{Pδ-Pε}$=21.3, Pε), −10.52 (1P, br d, J$_{Pα-Pβ}$=27.9, Pα); HRMS (−) ESI m/z found: 1003.1435, calc. for C$_{27}$H$_{39}$N$_{14}$O$_{20}$P$_4$$^-$: 1003.1421; hydrolysis in D$_2$O: 11%.

m$^7$GppC$_2$H$_4$-Triazole-C$_2$H$_4$NHppG

Obtained according to GP G from m$^7$GppC$_4$H$_5$ (375 mOD, 0.033 mmol, 100 mM) and GppNHC$_4$H$_5$N$_3$ (397 mOD, 0.033 mmol, 100 mM) while stirring with CuSO$_4$ (1.6 mg, 0.0066 mmol, 20 mM) and sodium ascorbate (2.6 mg, 0.013 mmol, 40 mM) in 0.328 mL of H$_2$O for 1 h. After quenching the reaction with Na$_2$EDTA (24.6 mg, 0.066 mmol), the product was subjected to RP HPLC purification which afforded m$^7$GppC$_2$H$_4$-triazole-C$_2$H$_4$NHppG as ammonium salt.

$^1$H NMR (400 MHz, D$_2$O, 25° C.) δ$_H$: 9.18 (1H, s, H8 m$^7$G), 8.12 (1H, s, H8 G or H$_{triazole}$), 7.69 (1H, s, H8 G or H$_{triazole}$), 6.02 (1H, d, J$_{1'-2'}$=3.5, H1' G or m$^7$G), 5.88 (1H, d, J$_{1'-2'}$=5.5, H1' G or m$^7$G), 4.72-4.76 (2H, overlapped H2' G and m$^7$G), 4.50-4.54 (2H, overlapped H3' G and m$^7$G), 4.40-4.43 (1H, m, H4 G or m$^7$G), 4.33-4.39 (2H, overlapped H4' G or m$^7$G and H5' G or m$^7$G), 4.28 (2H, br t, J$_{CH2(triazole)G-CH2(NH)}$=6.6, H$_{CH2(triazole)G}$), 4.17-4.29 (3H, overlapped H5'' G and m$^7$G and H5' G or m$^7$G), 4.06 (3H, s, m$^7$), 3.20-3.28 (2H, m, H$_{CH2(NH)}$), 2.79-2.85 (2H, m, H$_{CH2(triazole)m7G}$ or H$_{CH2(P)}$), 1.99-2.08 (2H, m, H$_{CH2(triazole)m7G}$ or H$_{CH2(P)}$); $^{31}$P NMR (162 MHz, D$_2$O, 25° C.) δ$_P$: 17.61-18.10 (1P, m, Pδ), −1.64 (1P, dt, J$_{Pα-Pβ}$=22.0, J$_{Pβ-CH2(NH)}$=12.5, Pβ), −10.22 (1P, br d, J$_{Pα-Pβ}$=22.0, Pα), −10.50 (1P, br d, J$_{Pδ-Pε}$=24.9, Pε); HRMS (−) ESI m/z found: 1003.1444, calc. for C$_{27}$H$_{39}$N$_{14}$O$_{20}$P$_4$$^-$: 1003.1421; hydrolysis in D$_2$O: 10%.

m$_2$$^{7,2'-O}$Gppp-Triazole-C$_2$H$_4$NHppG (m$_2$$^{7,2'-O}$Gppptr$_2$H$_4$NHppG)

Obtained according to GP H from m$_2$$^{7,2'-O}$GpppC$_2$H (377 mOD, 0.033 mmol, 50 mM) and GppNHC$_2$H$_4$N$_3$ (400 mOD, 0.033 mmol, 50 mM) while stirring with CuSO$_4$ (3.3 mg, 0.013 mmol, 20 mM) and sodium ascorbate (5.2 mg, 0.026 mmol, 40 mM) in 662 mL of H$_2$O:t-BuOH (2:1, v/v) for 0.5 h. After quenching the reaction with Na$_2$EDTA (48.4 mg, 0.13 mmol), the product was subjected to RP HPLC purification which afforded m$^7$Gppp-triazole-C$_2$H$_4$NHppG as ammonium salt.

$^1$H NMR (500 MHz, Deuterium Oxide) δ 9.13 (s, 1H, H8 m$^7$G), 8.24 (s, 1H, H8 G or H$_{triazole}$), 8.06 (s, 1H, H8 G or H$_{triazole}$), 6.08 (d, J=3.1 Hz, 1H, H1' m$^7$G), 5.87 (d, J=5.8 Hz, 1H, H1' G), 4.82 (overlapped with HDO, 1H, H2' G), 4.59 (dd, J=6.1, 4.9 Hz, 1H, H3' m$^7$G), 4.52 (dd, J=5.3, 3.7 Hz, 1H, H3' G), 4.42 (t, J=6.4 Hz, 2H, H$_{CH2-triazole}$), 4.35-4.26 (m, 4H, overlapped H2' m$^7$G, H4' G and m$^7$G, H5' G or m$^7$G), 4.25-4.13 (m, 3H, overlapped H5' G or m$^7$G, H5'' G and m$^7$G), 4.07 (s, 3H, m$^7$), 3.59 (s, 3H, m$^{2'O}$), 3.32 (dt, J=12.6, 6.4 Hz, 2H, H$_{CH2-NH}$); $^{31}$P NMR (202 MHz, Deuterium Oxide) δ −1.36-−1.72 (m, 1P, Pβ), −6.34 (d, J=21.8 Hz, 1P, Pδ), −10.04-−10.29 (m, 1P, Pα), −10.49-−10.65 (m, 1P, Pζ), −22.34 (dd, J=21.8, 19.7 Hz, 1P, Pε); HRMS (−) ESI m/z found: 1069.0946, calc. for: C$_{26}$H$_{38}$N$_{14}$O$_{23}$P$_5$$^-$ 1069.0928.

m$_2$$^{7,2'-O}$Gppp-Triazole-C$_2$H$_4$OppG (m$_2$$^{7,2'-O}$Gpppt C$_2$H$_4$OppG)

Obtained according to GP H from m$_2$$^{7,2'-O}$GpppC$_2$H (330 mOD, 0.029 mmol, 48 mM) and GppOC$_2$H$_4$N$_3$ (350 mOD, 0.029 mmol, 48 mM) while stirring with CuSO$_4$ (2.9 mg, 0.012 mmol, 19 mM) and sodium ascorbate (4.6 mg, 0.023 mmol, 38 mM) in 0.600 mL of H$_2$O:t-BuOH (5:1, v/v) for 1 h. After quenching the reaction with Na$_2$EDTA (44.7 mg, 0.12 mmol), the product was subjected to RP HPLC purification which afforded m⁷Gppp-triazole-C₂H₄OppG as ammonium salt.

¹H NMR (500 MHz, Deuterium Oxide) δ 9.15 (s, 1H, H8 G or m⁷G or H$_{triazole}$), 8.38 (s, 1H, H8 G or m⁷G or H$_{triazole}$), 8.30 (s, 1H, H8 G or m⁷G or H$_{triazole}$), 6.09 (d, J=3.1 Hz, 1H, H1' m⁷G), 5.93 (d, J=5.3 Hz, 1H, H1' G), 4.77 (t, 1H, overlapped with HDO, H2' G), 4.66 (t, J=5.4 Hz, 2H, CH2$_{linker\ CH2-N}$), 4.58 (dd, J=6.0, 4.9 Hz, 1H, H3' m⁷G), 4.48 (dd, J=5.1, 4.0 Hz, 1H, H3' G), 4.39-4.26 (m, 6H, overlapped H2' m 7G, CH2$_{linker\ CH2-O}$, H4'G, H4' m⁷G, H5' G or m⁷G), 4.11-4.23 (m, 3H, H4' m⁷G, H5' G or m⁷G, H5' and H5" G or m⁷G), 4.08 (s, 3H, m⁷), 3.59 (s, 3H, m$^{2'-O}$); ³¹P NMR (202 MHz, Deuterium Oxide) δ −6.58 (d, J=21.6 Hz, 1P), −10.08−−10.87 (m, 3P, overlapped), −22.34 (t, J=20.6 Hz, 1P, Pδ); HRMS (−) ESI m/z found: 1070.0792, calc. for: C₂₆H₃₇N₁₃O₂₄P₅⁻ 1070.0768.

m₂$^{7,2'-O}$Gppp-Triazole-C₂H₄OpG (m₂$^{7,2'-O}$ Gpppt C₂H₄OpG)

Obtained according to GP H from m₂$^{7,2'-O}$GpppC₂H (330 mOD, 0.029 mmol, 25 mM) and GpOC₂H₄N₃ (350 mOD, 0.029 mmol, 25 mM) while stirring with CuSO₄ (2.9 mg, 0.012 mmol, 10 mM) and sodium ascorbate (4.6 mg, 0.023 mmol, 20 mM) in 1.150 mL of H₂O:t-BuOH (3:1, v/v) for 0.5 h. After quenching the reaction with Na₂EDTA (44.7 mg, 0.12 mmol), the product was subjected to RP HPLC purification which afforded m⁷Gppp-triazole-C₂H₄OpG as ammonium salt.

1H NMR (500 MHz, Deuterium Oxide) δ 9.14 (s, 1H, H8 G or m⁷G H$_{triazole}$), 8.31 (s, 1H, H8 G or m⁷G or H$_{triazole}$), 8.05 (s, 1H, H8 G or m⁷G H$_{triazole}$), 6.06 (d, J=2.9 Hz, 1H, H1' m⁷G), 5.83 (d, J=5.8 Hz, 1H, H1' G), 4.70 (dd, J=5.2, 5.8 Hz, 1H, H2' G), 4.65 (t, J=5.2 Hz, 2H, CH₂ $_{linker\ CH2-N3}$), 4.57 (dd, J=6.3, 4.9 Hz, 1H, H3' m⁷G), 4.27-4.34 (m, 4H, overlapped H2' m⁷G and H3' G, H4' G or H5' or H5" m⁷G), 4.27-4.22 (m, 1H, H4' G), 4.16-4.21 (m, 3H, overlapped CH₂ $_{linker\ CH2-O}$ and H4' G or H5' or H5" m⁷G), 4.06 (s, 3H, m⁷), 3.87 (ddd, J=11.6, 4.6, 2.9 Hz, 1H), 3.81 (ddd, J=11.6, 5.2, 4.0 Hz, 1H), 3.60 (s, 3H, m$^{2'-O}$); ³¹P NMR (202 MHz, Deuterium Oxide) δ 0.65-0.67 (m, 1P, Pα), −6.73 (d, J=22.2 Hz, 1P, Pγ), −10.69 (m, 1P, Pε), −22.36 (dd, J=22.2, 18.7 Hz, 1P, Pδ); HRMS (−) ESI m/z found: 990.1097, calc. for: C₂₆H₃₆N₁₃O₂₁P₄⁻ 990.11047.

m₂$^{7,2'-O}$Gpp-Triazole-C₂H₄OppG (m₂$^{7,2'-O}$ Gppt C₂H₄OppG)

Obtained according to GP H from m₂$^{7,2'-O}$GppC₂H (330 mOD, 0.029 mmol, 48 mM) and GppOC₂H₄N₃ (350 mOD, 0.029 mmol, 48 mM) while stirring with CuSO₄ (2.9 mg, 0.012 mmol, 19 mM) and sodium ascorbate (4.6 mg, 0.023 mmol, 38 mM) in 0.600 mL of H₂O:t-BuOH (5:1, v/v) for 1 h. After quenching the reaction with Na₂EDTA (44.7 mg, 0.12 mmol), the product was subjected to RP HPLC purification which afforded m⁷Gpp-triazole-C₂H₄OppG as ammonium salt.

¹H NMR (500 MHz, Deuterium Oxide) δ 9.13 (s, 1H, H8 G or m⁷G or H$_{triazole}$), 8.31 (s, 1H, H8 G triazole, or m⁷G or H$_{triazole}$), 8.09 (s, 1H, H8 G or m⁷G or H$_{triazole}$), 6.06 (d, J=3.0 Hz, 1H, H1' m⁷G), 5.85 (d, J=6.0 Hz, 1H, H1' G), 4.75 (dd, J=5.1, 6.0 Hz, 1H, H2' G), 4.68 (t, J=5.1 Hz, 2H, CH2$_{linker\ CH2-N}$), 4.53 (dd, J=6.1, 4.9 Hz, 1H, H3 m⁷G), 4.47 (dd, J=5.1, 3.4 Hz, 1H, H3' G), 4.38-4.29 (m, 5H, overlapped overlapped H2' m⁷G, CH2$_{linker\ CH2-O}$, H4'G, H4' m⁷G), 4.26 (ddd, J=11.9, 4.7, 2.6 Hz, 1H, H5' G or m7G), 4.12-4.19 (m, 2H, overlapped H5' G or m⁷G, H5" G or m⁷G), 4.05-4.10 (m, 1H, H5" G or m⁷G), 4.04 (s, 3H, m⁷), 3.59 (s, 3H, m$^{2'-O}$); ³¹P NMR (202 MHz, Deuterium Oxide) δ −6.52 (d, J=24.3 Hz, 1P), −10.70−−10.37 (m, 3P); HRMS (−) ESI m/z found: 990.1133, calc. for: C₂₆H₃₆N₁₃O₂₁P₄⁻ 990.1105.

Example 2—Determination of K$_{AS}$ for Cap Analogue-eIF4E Complexes

Association constants for cap analogue-eIF4E complexes were determined using fluorescence quenching titration method as described previously.[42] Measurements were performed using a quartz cuvette with optical path length of 4 mm for absorption and 10 mm for emission on LS-50B spectrofluorometer Perkin-Elmer Co. (Waltham, Mass., USA). Titration experiments were carried out at 20° C. in 50 mM Hepes/KOH buffer, pH 7.20 containing 100 mM KCl, 0.5 mM EDTA, and 1 mM DTT. During the experiment 1 µl aliquots of ligand solution was added to the 1400 µl of 0.1 µM protein solution. Protein fluorescence was monitored at 337 or 345 nm (excitation 280 or 295 nm, respectively). For data analysis fluorescence intensity correction was applied for sample dilution and inner filter effect. Association constants were determined by fitting theoretical dependence of fluorescence intensity on total ligand concentration. Each experiment was performed in triplicate, the association constants were calculated as weighted averages.

Table 2. lists the K$_{AS}$ values for complexes of eIF4E and selected phosphotriazole cap analogues compared to reference cap analogues.

TABLE 2

| Compound | K$_{AS}$ [µM⁻¹] |
| --- | --- |
| m⁷GpNHC₂H₄tpppG | 3.10 ± 0.18 |
| m⁷GppptC₂H₄NHpG | 21.94 ± 0.69 |
| m⁷GppptCH₂tC₂H₄NHpG | 18.21 ± 0.72 |
| m⁷GMP | 0.806 ± 0.067[42] |
| m⁷GDP | 20.4 ± 1.5[42] |
| m⁷GpppG | 12.5 ± 0.3[43] |
| m₂$^{7,3'-O}$GpppG | 10.2 ± 0.6[43] |

Example 3—Incorporation of Dinucleotide Cap Analogues at the 5' End of Transcripts Table 3. lists sequences of DNA and RNA of oligonucleotides used in molecular biology experiments.

TABLE 3

| SEQ ID NO | Name | Sequence | Description |
| --- | --- | --- | --- |
| 1 | DNA1 | ATACGATTTAGGTGACACTATAGAAGAAGCGGGCATGC GGCCAGCCATAGCCGATCA | DNA template for SEQ ID NO: 4 transcritpion; synthetic |
| 2 | DNA2 | TGATCGGCTATGGCTGGCCGCATGCCCGCTTCTTCTAT AGTGTCACCTAAATCGTAT | DNA template for SEQ ID NO: 4 transcription; synthetic |

TABLE 3-continued

| SEQ ID NO | Name | Sequence | Description |
|---|---|---|---|
| 3 | DNA3 (DNazyme10-23)[12] | TGATCGGCTAGGCTAGCTACAACGAGGCTGGCCGC | DNazyme10-23[12]; synthetic |
| 4 | RNA1 (35 nt) | GAAGAAGCGGGCAUGCGGCCAGCCAUAGCCGAUCA | RNA substrate of DNA-catalyzed trimming; synthetic |
| 5 | RNA2 (25 nt) | GAAGAAGCGGGCAUGCGGCCAGCCA | RNA product of DNA-catalyzed trimming of SEQ ID NO: 4; synthetic |
| 6 | DNA4 | ATTTAGGTGACACTATAGAAGTACTGTTGGTAAAGCCACCATGGAAGACGCCAAAAACAT | DNA primer used for the synthesis of a template for luciferase mRNA transcription; synthetic |
| 7 | DNA5 | TTACAATTTGGACTTTCCGCCCT | DNA primer used for the synthesis of a template for luciferase mRNA transcription; synthetic |

3.1. Synthesis of Transcripts for Capping Efficiency Determination

Prior to in vitro transcription annealing of a template was performed. DNA1 (SEQ ID NO: 1) and DNA2 (SEQ ID NO: 2) (20 µM each) were incubated in the presence of 4 mM Tris-HCl pH 8.0, 15 mM NaCl and 0.1 mM EDTA at 95° C. for 2 min and then at room temperature for 30 min. After 10-fold dilution the mixture was directly used for in vitro transcription.

In vitro transcription was performed on pre-annealed DNA1 (SEQ ID NO: 1) and DNA2 (SEQ ID NO: 2) (0.5 µM) with SP6 RNA polymerase (New England BioLabs) (1 U/µl) in the presence of 1×RNA Pol Reaction Buffer (New England BioLabs), 5 mM DTT, RiboLock RNase Inhibitor (ThermoFisher Scientific) (2.0 U/µl), 0.5 mM UTP, 0.5 mM ATP, 0.5 mM CTP, 0.125 mM GTP and 1.25 mM of appropriate triazole-modified dinucleotide cap analogue ($m_2^{7,2'-O}$Gppp-triazole-G, $m_2^{7,2'-O}$Gppp-triazole-$C_2H_4$NHpG, $m_2^{7,2'-O}$Gppp-triazole-$C_2H_4$NHppG, $m_2^{7,2'-O}$Gppp-triazole-$C_2H_4$OppG, $m_2^{7,2'-O}$Gppp-triazole-$C_2H_4$OpG, $m_2^{7,2'-O}$Gpp-triazole-$C_2H_4$OppG) and reference GpppG, $m^7$GpppG and $m_2^{7,3'-O}$GpppG.[6] The reaction mixture was incubated at 40° C. for 1.5 h followed by addition of TURBO Dnase (Ambion) (0.1 U/µl) and incubation at 37° C. for another 30 min. The reaction was quenched by addition of 2 µl of 0.5 M EDTA pH 8.0 and purified with RNA Clean&Concentrator-5 kit (Zymo Research) to afford capped RNA1 (SEQ ID NO: 4) strands.

Figure 3:
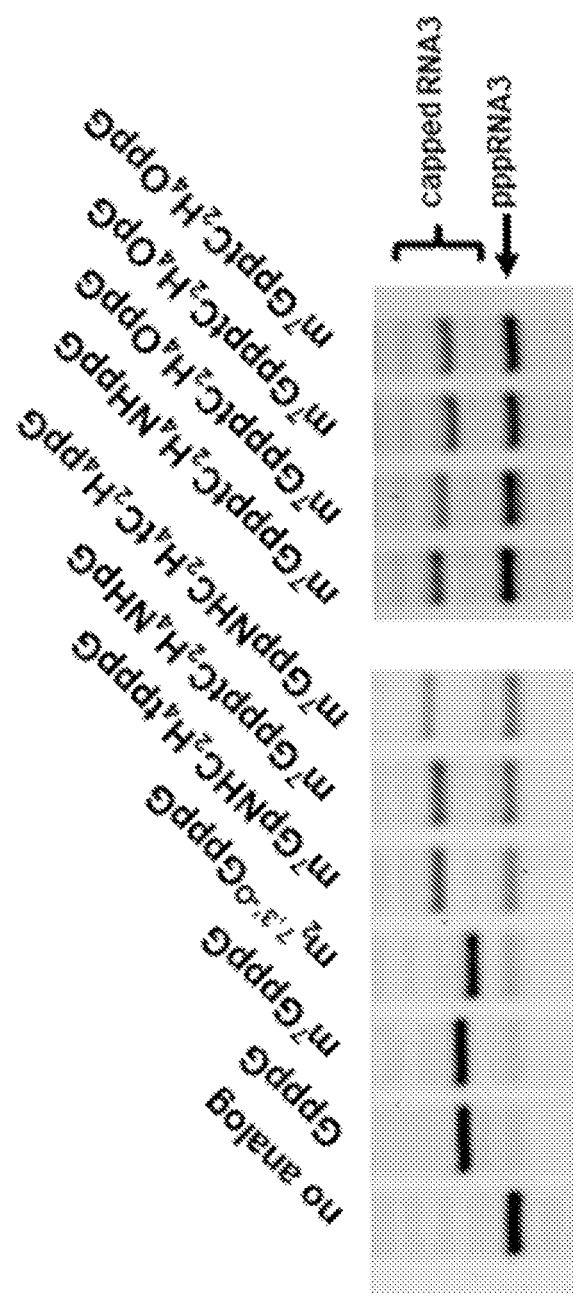
FIG. 3 depicts polyacrylamide gel analysis of short RNAs obtained by in vitro transcription in the presence of selected phosphotriazole cap analogues along with several reference cap analogues.

To reduce heterogeneity, each capped RNA1 (11.42 ng/µl, ca. 1 µM) was incubated in presence of 50 mM Tris-HCl pH 8.0, 50 mM $MgCl_2$, RiboLock RNase Inhibitor (ThermoFisher Scientific) (2.0 U/µl) and DNA3 (SEQ ID NO: 3) (1 µM) at 37° C. for 1 h to afford RNA2 (SEQ ID NO: 5).[44] The reaction was stopped by freezing in liquid nitrogen and directly analyzed by PAGE (FIG. 3).

Relative bands intensity was determined using CLIQS v1.0 program.

Example 4—Translation Studies 4.1. Synthesis of Transcripts

In vitro transcription was performed on PCR product coding Firefly luciferase under the control of SP6 promoter (obtained from pGEN-luc (Promega) using primers: DNA4 (SEQ ID NO: 6) and DNA5 (SEQ ID NO:7) (5 ng/µl) with SP6 RNA polymerase (1 U/µl) (New England BioLabs) in the presence of 1×RNA Pol Reaction Buffer (New England BioLabs), 5 mM DTT, RiboLock RNase Inhibitor (ThermoFisher Scientific) (2.0 U/µl), 0.5 mM UTP, 0.5 mM ATP, 0.5 mM CTP, 0.125 mM GTP and 1.25 mM of appropriate triazole-modified dinucleotide cap analogue and reference GpppG, $m^7$GpppG and $m_2^{7,3'-O}$GpppG. The reaction mixture was incubated at 40° C. for 1.5 h followed by addition of TURBO Dnase (Ambion) (0.1 U/µl) and incubation at 37° C. for another 30 min. The reaction was quenched by addition of 2 µl of 0.5 M EDTA pH 8.0 and purified with NucleoSpin RNA Clean-up XS kit (Macherey-Nagel) to afford luciferase-coding RNA strands capped with appropriate cap analogue.

4.2. Translation

For each capped luciferase-coding RNA four diluted solutions were prepared—3.0 ng/µl, 1.5 ng/µl, 0.75 ng/µl, 0.375 ng/µl. Translation studies were performed using Rabbit Reticulocyte Lysate System (Promega). 9 µl of a mixture containing Rabbit Reticulocyte Lysate (4 µl), Amino Acid Mixture Minus Leucine (0.05 µl of 1 mM solution), Amino Acid Mixture Minus Methionine (0.05 µl of 1 mM solution), potassium acetate (1.9 µl of 1 M solution), $MgCl_2$ (0.4 µl of 25 mM solution) and 2.1 µl of water was incubated at 30° C. for 1 h after which 1 µl of appropriate luciferase-coding RNA solution was added and incubation of the reaction was continued at 37° C. for another hour. The reaction was stopped by freezing in liquid nitrogen.

Figure 4:
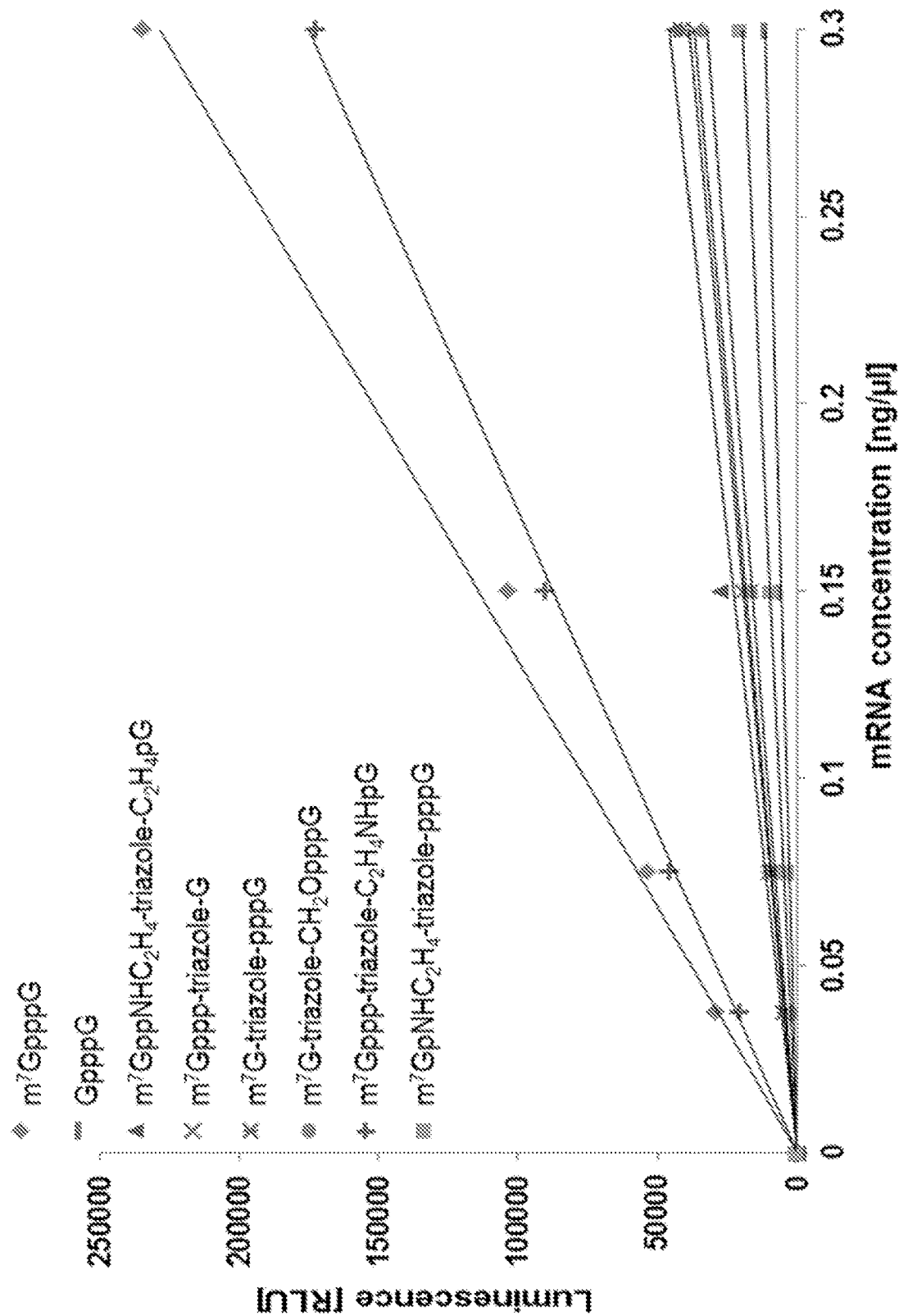
FIG. 4 depicts representative results of a single translation efficiency experiment for luciferase mRNAs capped with different cap structures in rabbit reticulocyte lysates.

Translation efficiency was determined using Luciferase Reporter System (Promega). The samples were defrosted just before the experiment. To every sample 50 µl of Luciferase Assay Reagent was added just before measurement of luminescence on Synergy H1 Microplate Reader (Bio Tek). The measurement were performed for every four samples independently due to low stability of luminescence signal. The results are presented on. FIG. 4 as proportions between regression coefficients of linear relationships between capped luciferase-coding RNA concentration in translation reaction (300 pg/µl, 150 pg/µl, 75 pg/µl, 37.5 pg/µl) and corresponding luminescence signal.

Table 4. lists capping efficiencies for short oligonucleotides terminated with phospotriazole cap analogs and translation efficiencies in rabbit reticulocyte lysates for mRNAs encoding firefly luciferase capped with different phosphotriazole analogs. It also lists corresponding data for unmodified cap analog ($m^7$GpppG), unmodified ARCA ($m_2^{7,3'-O}$GpppG), and example cap analogs containing triazole moiety within the nucleoside moiety for comparison ($m^7$GtpppG and $m^7$GtCH$_2$OpppG).

TABLE 4

| Cap analogue | Capping efficiency | Translation efficiency |
|---|---|---|
| GpppG | 92% | 0.058 ± 0.008 |
| $m^7$GpppG | 90% | 1 |
| $m^7$GpNHC$_2$H$_4$tCH$_2$ppG | 47% | 0.085 ± 0.017 |
| $m^7$GpNHC$_2$H$_4$tCH$_2$pppG | 62% | 0.060 ± 0.004 |
| $m^7$GppCH$_2$tC$_2$H$_4$NHpG | 54% | 0.155 ± 0.019 |
| $m^7$GpppCH$_2$tC$_2$H$_4$NHpG | 44% | 0.94 ± 0.11 |
| $m^7$GpNHC$_2$H$_4$tppG | 57% | 0.075 ± 0.009 |
| $m^7$GpNHC$_2$H$_4$tpppG | 57% | 0.103 ± 0.027 |
| $m^7$GpptC$_2$H$_4$NHpG | 56.8% | 0.50 ± 0.06 |
| $m^7$GppptC$_2$H$_4$NHpG | 52% | 0.89 ± 0.11 |
| $m^7$GppNHC$_2$H$_4$tC$_2$H$_4$ppG | 30% | 0.239 ± 0.028 |

TABLE 4-continued

| Cap analogue | Capping efficiency | Translation efficiency |
|---|---|---|
| $m^7$GppC$_2$H$_4$tC$_2$H$_4$NHppG | 48.8% | 0.085 ± 0.017 |
| $m_2^{7,3'-O}$GpppG | 83% | 1.526 ± 0.043 |
| $m_2^{7,2'-O}$GppptC$_2$H$_4$NHpG | 41% | 1.462 ± 0.182 |
| $m^7$GtpppG | 80% | 0.17 ± 0.02 |
| $m^7$GtCH$_2$OpppG | 78% | 0.14 ± 0.04 |
| $m_2^{7,2'-O}$GppptC$_2$H$_4$NHppG | 43.0% | 2.226 ± 0.399 |
| $m_2^{7,2'-O}$GppptC$_2$H$_4$OppG | 38.0% | 1.749 ± 0.263 |
| $m_2^{7,2'-O}$GppptC$_2$H$_4$OpG | 47.6% | 2.773 ± 0.293 |
| $m_2^{7,2'-O}$GpptC$_2$H$_4$OppG | 44.2% | 1.675 ± 0.168 |

Example 5 Susceptibility to Degradation by hDcp2

The reaction mixture containing synthesized RNA2 (SEQ ID NO: 5) capped with $m_2^{7,3'-O}$GpppG, $m_2^{7,2'-O}$Gppp-triazole-G and $m_2^{7,2'-O}$Gppp-triazole-C$_2$H$_4$NHpG (for details of the synthesis see 1.4.1) was precipitated and the pellet was dissolved in water and incubated in the presence of 1×TURBO DNase Buffer (Ambion), RiboLock RNase Inhibitor (ThermoFisher Scientific) (2.0 U/µl) and TURBO Dnase (Ambion) (0.1 U/µl) at 37° C. for 30 min. The reaction was then subjected to phenol-chloroform extraction followed by precipitation. The resulting RNA2 water solution was directly used for Dcp2-catalyzed decapping experiments.

Figure 5:
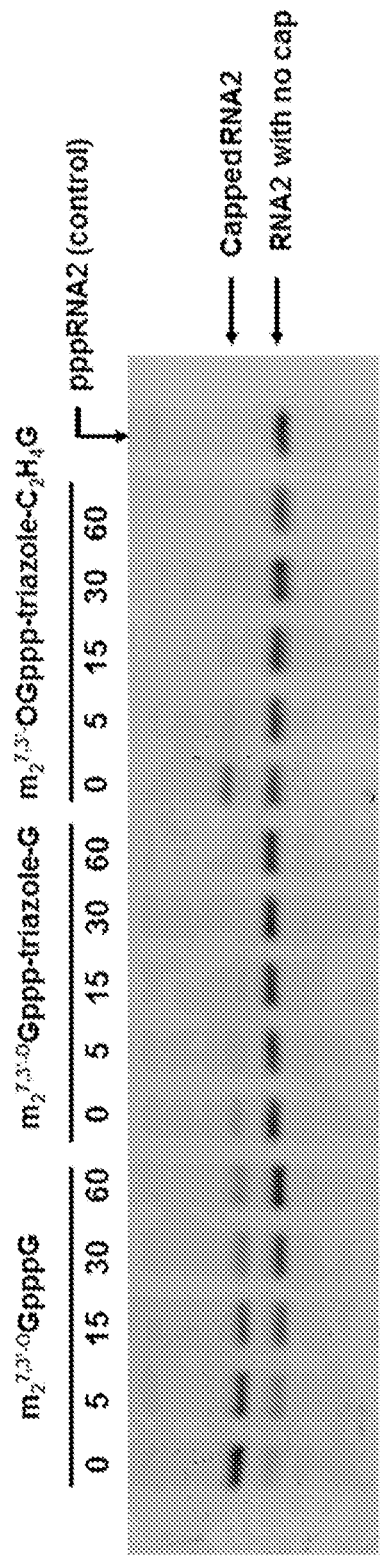
FIG. 5 depicts polyacrylamide gel electrophoretic analysis of decapping reactions catalyzed by Dcp2.
Figure 6:
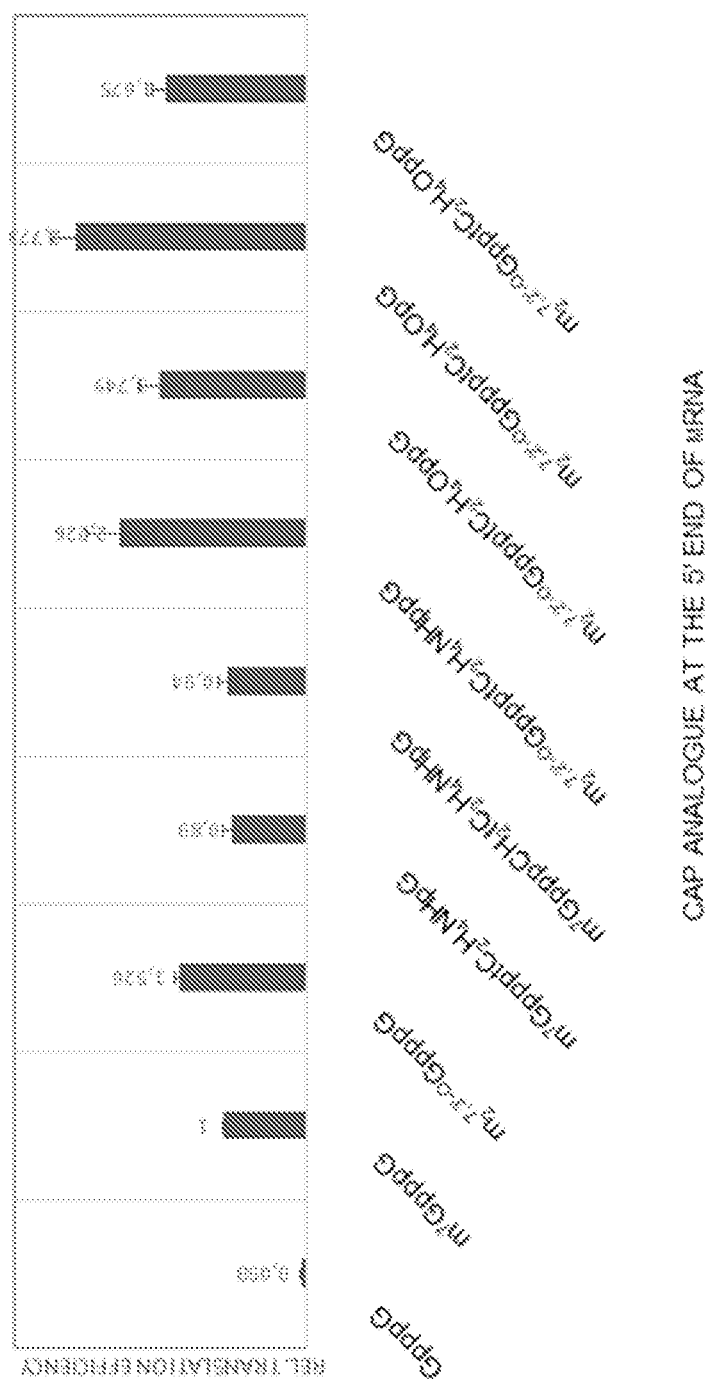
FIG. 6 depicts relative translation efficiency of selected phosphotriazole cap analogues along with several reference cap analogues.

Appropriate RNA2 was incubated in the presence of 50 mM NH$_4$Cl, 5 mM MgCl$_2$, 50 mM Tris-HCl pH 8.0, 0.01% IGEPAL CA-630 (Sigma Aldrich), 2 mM MnCl$_2$, 1 mM DTT and 7 nM hDcp2 at 37° C. 5 µl aliquots of the reaction were collected after 5, 15, 30, 60 min of incubation or just after addition of the enzyme ("0 min" timepoint) and quenched with loading dye (5 M urea, 44% formamide, 20 mM EDTA, 0.03% bromophenol blue, 0.03% xylene cyanol) and directly analyzed by 15% PAGE (FIG. 5).

Example 6—Stability Studies

Analogues $m_2^{7,2'-O}$Gppp-triazole-C$_2$H$_4$NHppG, $m_2^{7,2'-O}$Gppp-triazole-C$_2$H$_4$OppG, $m_2^{7,2'-O}$Gppp-triazole-C$_2$H$_4$OpG, $m_2^{7,2'-O}$Gpp-triazole-C$_2$H$_4$OppG were incubated in sealed vials at 20 µM and at room temperature in four different buffers: 0.1 M formate buffer pH 3.0, 0.1 M acetate buffer pH 5.0, 0.1 M HEPES pH 7.0 and 0.1 M borate buffer pH 9.0. Samples of 50 µl for each condition were taken after 0, 2 and 24 h and analysed by RP HPLC. The starting compound peak area was determined for each time-point and % of remaining cap was calculated in reference to the time-point 0 h.

TABLE 5

| | Bufor pH 3 | | Bufor pH 5 | | Bufor pH 7 | | Bufor pH 9 | |
|---|---|---|---|---|---|---|---|---|
| | 4 h | 24 h | 4 h | 24 h | 4 h | 24 h | 4 h | 24 h |
| $m_2^{7,2'-O}$Gppp-triazole-C$_2$H$_4$NHppG | 19.0% | 72.9% | 0 | 0 | 0 | 0 | 0.5% | 3.0% |
| $m_2^{7,2'-O}$Gppp-triazole-C$_2$H$_4$OppG | 0 | 0 | 0 | 0 | 0 | 0 | 1.1% | 4.0% |
| $m_2^{7,2'-O}$Gppp-triazole-C$_2$H$_4$OpG | 0 | 0 | 0 | 0 | 0 | 0 | 0.1% | 1.2% |
| $m_2^{7,2'-O}$Gppp-triazole-C$_2$H$_4$OppG | 0 | 0 | 0 | 0 | 0 | 0 | 1.0% | 4.5% |

REFERENCES (The numbers within the application written in upper index indicate one of the below literature document to which they refer)

1. Moore, M., From birth to death: The complex lives of eukaryotic mRNAs. *Science* 2005, 309 (5740), 1514-1518.
2. Ziemniak, M.; Strenkowska, M.; Kowalska, J.; Jemielity, J., Potential therapeutic applications of RNA cap analogs. *Future Medicinal Chemistry* 2013, 5 (10), 1141-1172.
3. Grudzien-Nogalska, E.; Stepinski, J.; Jemielity, J.; Zuberek, J.; Stolarski, R.; Rhoads, R. E.; Darzynkiewicz, E., Synthesis of anti-reverse cap analogs (ARCAs) and their applications in mRNA translation and stability. *Translation Initiation: Cell Biology, High-Throughput Methods, and Chemical-Based Approaches* 2007, 431, 203-227.
4. Sahin, U.; Kariko, K.; Tureci, O., mRNA-based therapeutics—developing a new class of drugs. *Nature Reviews Drug Discovery* 2014, 13 (10), 759-780.
5. Stepinski, J.; Waddell, C.; Stolarski, R.; Darzynkiewicz, E.; Rhoads, R. E., Synthesis and properties of mRNAs containing the novel "anti-reverse" cap analogs 7-methyl (3'-O-methyl)GpppG and 7-methyl(3'-deoxy)GpppG. *Rna—a Publication of the Rna Society* 2001, 7 (10), 1486-1495.
6. Jemielity, J.; Fowler, T.; Zuberek, J.; Stepinski, J.; Lewdorowicz, M.; Niedzwiecka, A.; Stolarski, R.; Darzynkiewicz, E.; Rhoads, R. E., Novel "anti-reverse" cap analogs with superior translational properties. *Rna—a Publication of the Rna Society* 2003, 9 (9), 1108-1122.
7. Jemielity, J.; Kowalska, J.; Rydzik, A. M.; Darzynkiewicz, E., Synthetic mRNA cap analogs with a modified triphosphate bridge—synthesis, applications and prospects. *New Journal of Chemistry* 2010, 34 (5), 829-844.
8. Grudzien-Nogalska, E.; Jemielity, J.; Kowalska, J.; Darzynkiewicz, E.; Rhoads, R. E., Phosphorothioate cap analogs stabilize mRNA and increase translational efficiency in mammalian cells. *Rna—a Publication of the Rna Society* 2007, 13 (10), 1745-1755.
9. Kuhn, A. N.; Diken, M.; Kreiter, S.; Selmi, A.; Kowalska, J.; Jemielity, J.; Darzynkiewicz, E.; Huber, C.; Tureci, O.; Sahin, U., Phosphorothioate cap analogs increase stability and translational efficiency of RNA vaccines in immature dendritic cells and induce superior immune responses in vivo. *Gene Therapy* 2010, 17 (8), 961-971.
10. Grudzien, E.; Kalek, M.; Jemielity, J.; Darzynkiewicz, E.; Rhoads, R. E., Differential inhibition of mRNA degradation pathways by novel cap analogs. *Journal of Biological Chemistry* 2006, 281 (4), 1857-1867.
11. Gates, K. S.; Nooner, T.; Dutta, S., Biologically relevant chemical reactions of N7-alkylguanine residues in DNA. *Chemical Research in Toxicology* 2004, 17 (7), 839-856.
12. Mikkola, S.; Salomaki, S.; Zhang, Z.; Maki, E.; Lonnberg, H., Preparation and properties of mRNA 5'-cap structure. *Current Organic Chemistry* 2005, 9 (10), 999-1022.
13. Kadokura, M.; Wada, T.; Urashima, C.; Sekine, M., Efficient synthesis of gamma-methyl-capped guanosine 5'-triphosphate as a 5'-terminal unique structure of U6 RNA via a new triphosphate bond formation involving activation of methyl phosphorimidazolidate using ZnCl2 as a catalyst in DMF under anhydrous conditions. *Tetrahedron Letters* 1997, 38 (48), 8359-8362.
14. Jessen, H. J.; Ahmed, N.; Hofer, A., Phosphate esters and anhydrides—recent strategies targeting nature's favoured modifications. *Organic & Biomolecular Chemistry* 2014, 12 (22), 3526-3530.
15. Kowalska, J.; Lewdorowicz, M.; Zuberek, J.; Grudzien-Nogalska, E.; Bojarska, E.; Stepinski, J.; Rhoads, R. E.; Darzynkiewicz, E.; Davis, R. E.; Jemielity, J., Synthesis and characterization of mRNA cap analogs containing phosphorothioate substitutions that bind tightly to eIF4E and are resistant to the decapping pyrophosphatase DcpS. *Rna—a Publication of the Rna Society* 2008, 14 (6), 1119-1131.
16. Schulz, D.; Rentmeister, A., Current Approaches for RNA Labeling in Vitro and in Cells Based on Click Reactions. *Chembiochem* 2014, 15 (16), 2342-2347.
17. Phelps, K.; Morris, A.; Beal, P. A., Novel Modifications in RNA. *Acs Chemical Biology* 2012, 7 (1), 100-109.
18. Luo, Y.; Eldho, N. V.; Sintim, H. O.; Dayie, T. K., RNAs synthesized using photocleavable biotinylated nucleotides have dramatically improved catalytic efficiency. *Nucleic Acids Research* 2011, 39 (19), 8559-8571.
19. Dojahn, C. M.; Hesse, M.; Arenz, C., A chemo-enzymatic approach to specifically click-modified RNA. *Chemical Communications* 2013, 49 (30), 3128-3130.
20. Seidu-Larry, S.; Krieg, B.; Hirsch, M.; Helm, M.; Domingo, O., A modified guanosine phosphoramidite for click functionalization of RNA on the sugar edge. *Chemical Communications* 2012, 48 (89), 11014-11016.
21. Samanta, A.; Krause, A.; Jaeschke, A., A modified dinucleotide for site-specific RNA-labelling by transcription priming and click chemistry. *Chemical Communications* 2014, 50 (11), 1313-1316.
22. Schulz, D.; Holstein, J. M.; Rentmeister, A., A Chemo-Enzymatic Approach for Site-Specific Modification of the RNA Cap. *Angewandte Chemie—International Edition* 2013, 52 (30), 7874-7878.
23. Yamada, T.; Peng, C. G.; Matsuda, S.; Addepalli, H.; Jayaprakash, K. N.; Alam, M. R.; Mills, K.; Maier, M. A.; Charisse, K.; Sekine, M.; Manoharan, M.; Rajeev, K. G., Versatile Site-Specific Conjugation of Small Molecules to siRNA Using Click Chemistry. *Journal of Organic Chemistry* 2011, 76 (5), 1198-1211.
24. Averick, S. E.; Paredes, E.; Dey, S. K.; Snyder, K. M.; Tapinos, N.; Matyjaszewski, K.; Das, S. R., Autotransfecting Short Interfering RNA through Facile Covalent Polymer Escorts. *Journal of the American Chemical Society* 2013, 135 (34), 12508-12511.
25. Dohmen, C.; Froehlich, T.; Laechelt, U.; Roehl, I.; Vornlocher, H.-P.; Hadwiger, P.; Wagner, E., Defined Folate-PEG-siRNA Conjugates for Receptor-specific Gene Silencing. *Molecular Therapy—Nucleic Acids* 2012, 1.
26. Iversen, F.; Yang, C.; Dagnaes-Hansen, F.; Schaffert, D. H.; Kjems, J.; Gao, S., Optimized siRNA-PEG Conjugates for Extended Blood Circulation and Reduced Urine Excretion in Mice. *Theranostics* 2013, 3 (3), 201-209.
27. Paredes, E.; Das, S. R., Click Chemistry for Rapid Labeling and Ligation of RNA. *Chembiochem* 2011, 12 (1), 125-131.
28. Birts, C. N.; Sanzone, A. P.; El-Sagheer, A. H.; Blaydes, J. P.; Brown, T.; Tavassoli, A., Transcription of Click-Linked DNA in Human Cells. *Angewandte Chemie—International Edition* 2014, 53 (9), 2362-2365.
29. El-Sagheer, A. H.; Sanzone, A. P.; Gao, R.; Tavassoli, A.; Brown, T., Biocompatible artificial DNA linker that is read through by DNA polymerases and is functional in *Escherichia coli*. *Proceedings of the National Academy of Sciences of the United States of America* 2011, 108 (28), 11338-11343.
30. El-Sagheer, A. H.; Brown, T., New strategy for the synthesis of chemically modified RNA constructs exemplified by hairpin and hammerhead ribozymes. *Proceedings of the National Academy of Sciences of the United States of America* 2010, 107 (35), 15329-15334.
31. Chen, X.; El-Sagheer, A. H.; Brown, T., Reverse transcription through a bulky triazole linkage in RNA: implications for RNA sequencing. *Chemical Communications* 2014, 50 (57), 7597-7600.
32. Efthymiou, T. C.; Vanthi, H.; Oentoro, J.; Peel, B.; Desaulniers, J.-P., Efficient synthesis and cell-based silencing activity of siRNAS that contain triazole backbone linkages. *Bioorganic & Medicinal Chemistry Letters* 2012, 22 (4), 1722-1726.
33. Mutisya, D.; Selvam, C.; Kennedy, S. D.; Rozners, E., Synthesis and properties of triazole-linked RNA. *Bioorganic & Medicinal Chemistry Letters* 2011, 21 (11), 3420-3422.
34. Piecyk, K.; Lukaszewicz, M.; Darzynkiewicz, E.; Jankowska-Anyszka, M., Triazole-containing monophosphate mRNA cap analogs as effective translation inhibitors. *Rna—a Publication of the Rna Society* 2014, 20 (10), 1539-1547.

35. Kolb, H. C.; Finn, M. G.; Sharpless, K. B., Click chemistry: Diverse chemical function from a few good reactions. *Angewandte Chemie—International Edition* 2001, 40 (11), 2004-+.
36. Rydzik, A. M.; Lukaszewicz, M.; Zuberek, J.; Kowalska, J.; Darzynkiewicz, Z. M.; Darzynkiewicz, E.; Jemielity, J., Synthetic dinucleotide mRNA cap analogs with tetraphosphate 5',5' bridge containing methylenebis(phosphonate) modification. *Organic & Biomolecular Chemistry* 2009, 7 (22), 4763-4776.
37. Rydzik, A. M.; Kulis, M.; Lukaszewicz, M.; Kowalska, J.; Zuberek, J.; Darzynkiewicz, Z. M.; Darzynkiewicz, E.; Jemielity, J., Synthesis and properties of mRNA cap analogs containing imidodiphosphate moiety—Fairly mimicking natural cap structure, yet resistant to enzymatic hydrolysis. *Bioorganic and Medicinal Chemistry* 2012, 20 (5), 1699-1710.
38. Wanat, P.; Walczak, S.; Wojtczak, B. A.; Nowakowska, M.; Jemielity, J.; Kowalska, J., Ethynyl, 2-Propynyl, and 3-Butynyl C-Phosphonate Analogues of Nucleoside Di- and Triphosphates: Synthesis and Reactivity in CuAAC. *Organic Letters* 2015, 17 (12), 3062-3065.
39. Bandyopadhyay, S.; Mukherjee, S.; Dey, A., Modular synthesis, spectroscopic characterization and in situ functionalization using "click" chemistry of azide terminated amide containing self-assembled monolayers. *Rsc Advances* 2013, 3 (38), 17174-17187.
40. Mukaiyam. T; Hashimot. M, SYNTHESIS OF OLIGOTHYMIDYLATES AND NUCLEOSIDE CYCLIC PHOSPHATES BY OXIDATION-REDUCTION CONDENSATION. *Journal of the American Chemical Society* 1972, 94 (24), 8528-&.
41. Guranowski, A.; Wojdyla, A. M.; Rydzik, A. M.; Stepinski, J.; Jemielity, J., Plant nucleoside 5'-phosphoramidate hydrolase; simple purification from yellow lupin (Lupinus luteus) seeds and properties of homogeneous enzyme. *Acta Biochimica Polonica* 2011, 58 (1), 131-136.
42. Niedzwiecka, A.; Marcotrigiano, J.; Stepinski, J.; Jankowska-Anyszka, M.; Wyslouch-Cieszynska, A.; Dadlez, M.; Gingras, A. C.; Mak, P.; Darzynkiewicz, E.; Sonenberg, N.; Burley, S. K.; Stolarski, R., Biophysical studies of eIF4E cap-binding protein: Recognition of mRNA 5' cap structure and synthetic fragments of eIF4G and 4E-BP1 proteins. *Journal of Molecular Biology* 2002, 319 (3), 615-635.
43. Zuberek, J.; Jemielity, J.; Jablonowska, A.; Stepinski, J.; Dadlez, M.; Stolarski, R.; Darzynkiewicz, E., Influence of electric charge variation at residues 209 and 159 on the interaction of eIF4E with the mRNA 5' terminus. *Biochemistry* 2004, 43 (18), 5370-5379.
44. Coleman, T. M.; Wang, G. C.; Huang, F. Q., Superior 5' homogeneity of RNA from ATP-initiated transcription under the T7 phi 2.5 promoter. *Nucleic Acids Research* 2004, 32 (1).
45. Walczak S. et al. Synthesis and properties of dinucleotide cap analogs containing a triazole ring within the oligophosphate bridge, Collection of Czechoslovak Chemical Communications, 2015, Volume 14, Pages 289-290.
46. Warminski, M.; Kowalska, J.; Buck, J.; Zuberek, J.; Lukaszewicz, M.; Nicola, C.; Kuhn, A. N.; Sahin, U.; Darzynkiewicz, E.; Jemielity, J.; The synthesis of isopropylidene mRNA cap analogs modified with phosphorothioate moiety and their evaluation as promoters of mRNA translation, *Bioorg Med Chem Lett.* 2013, 23(13), 3753-8.

The invention claimed is:

1. A compound of formula (I)

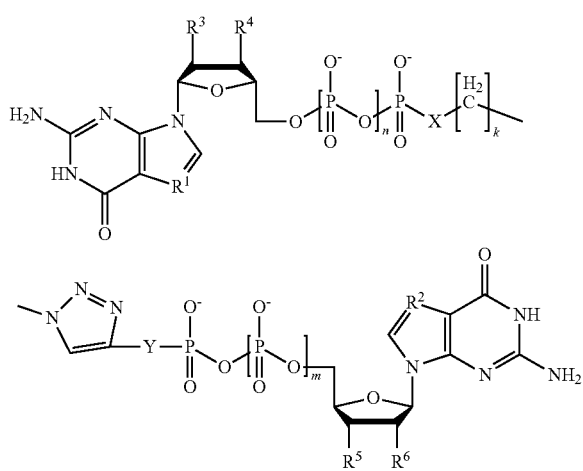

Formula I or a stereoisomer or salt thereof, wherein $R^1$ and $R^2$ are selected from the group consisting of N, $N^+$—$CH_3$, $N^+$—$C_2H_5$, $N^+$—$C_3H_8$, $N^+$—$C_4H_5$, $N^+$—$CH_2C_6H_5$ wherein at least one of $R^1$, $R^2$ is not N;

n and m are independently chosen from the group consisting of 0, 1 and 2;

X is selected from the group consisting of O, NH, S, $CH_2$ k is 1 or 2

Y is either void or selected from the group of —$CH_2$—, —$CH_2CH_2$—, —$CH_2O$—, —$CH_2S$—, —$CH_2NH$—, —$CH_2CH_2O$—, —$CH_2CH_2NH$—, —$CH_2CH_2S$—

$R^3$, $R^4$, $R^5$, $R^6$ are selected from the group consisting of H, OH, $OCH_3$, or $OCH_2CH_3$; wherein $R^3$ and $R^4$ may be the same or different; $R^5$ and $R^6$ may be the same or different; if either of $R^3$, $R^4$ is different than OH than $R^5$ and $R^6$ are both OH; if either of $R^5$, $R^6$ is different than OH than $R^3$ and $R^4$ are both OH.

2. The compound according to claim 1, wherein $R^1$ is $N^+$—$CH_3$, $R^3$ and $R^4$ are selected from the group consisting of OH and $OCH_3$ and at least one of $R^3$, $R^4$ is not OH, $R^5$ and $R^6$ are both OH, and n is at least 1.

3. The compound according to claim 1, wherein $R^2$ is $N^+$—$CH_3$, $R^5$ and $R^6$ are selected from the group consisting of OH and $OCH_3$ and at least one of $R^5$, $R^6$ is not OH, $R^3$ and $R^4$ are both OH, and m is at least 1.

4. The compound according to claim 1, wherein the compound is selected from the group consisting of the following:
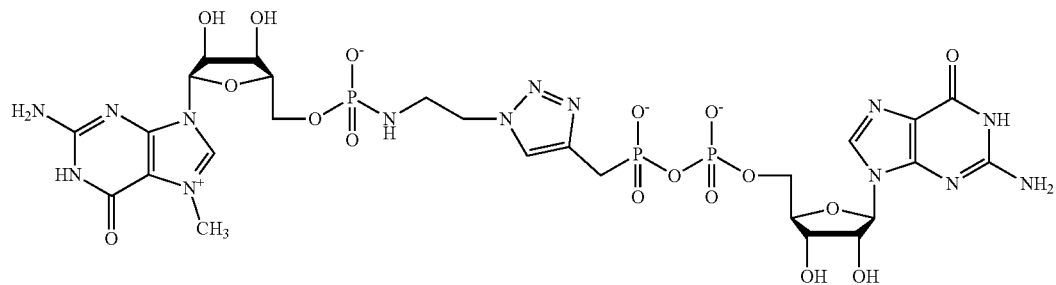
m⁷GpNHC₂H₄tCH₂ppG
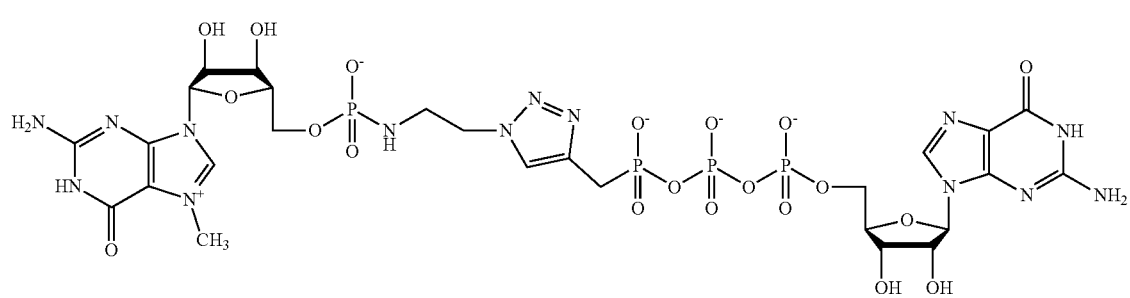
m⁷GpNHC₂H₄tCH₂pppG
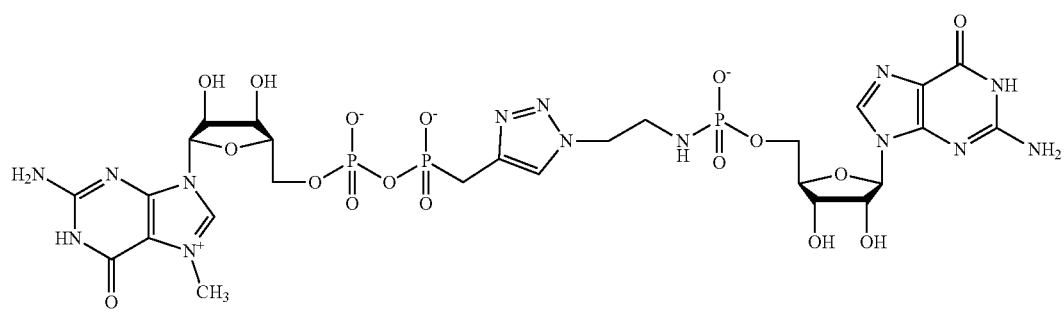
m⁷GppCH₂t C₂H₅NHpG
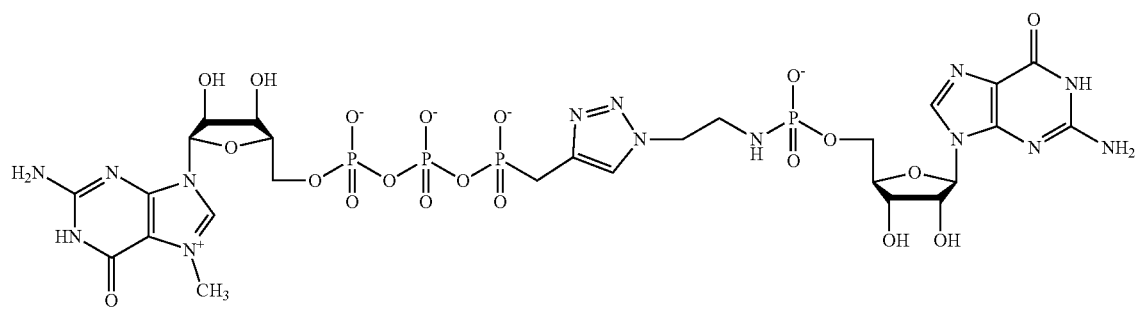
m⁷GpppCH₂t C₂H₄NHpG -continued
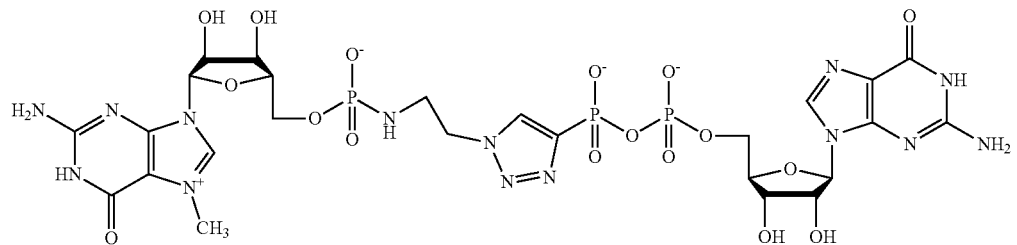
m⁷GpNHC₂H₄tppG
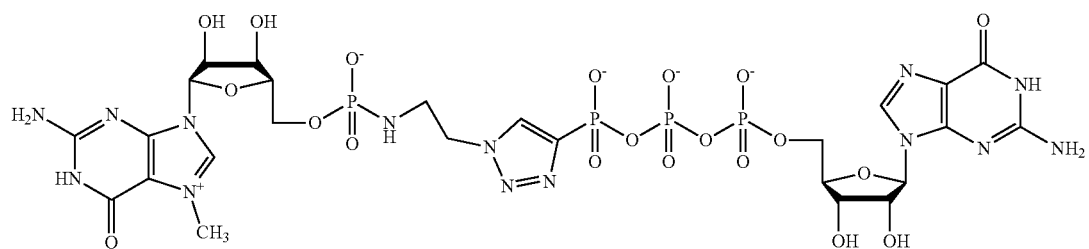
m⁷GpNHC₂H₄tpppG
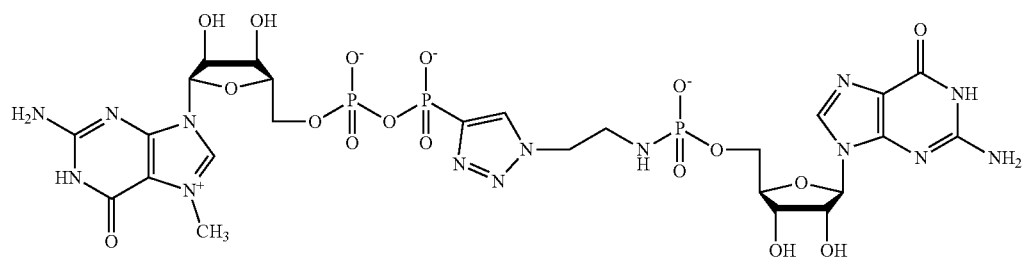
m⁷GpptC₂H₄NHpG
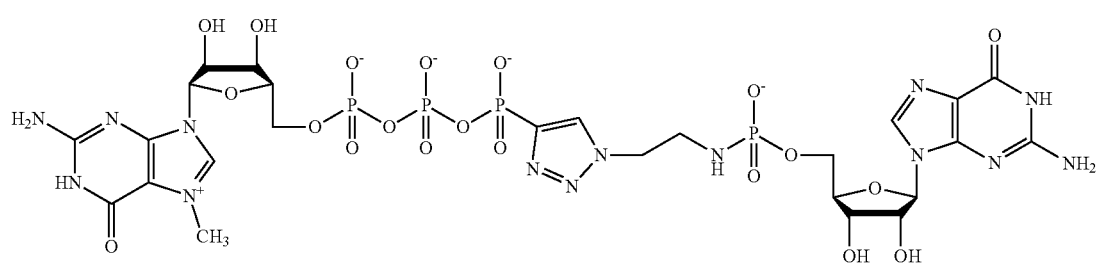
m⁷GppptC₂H₄NHpG
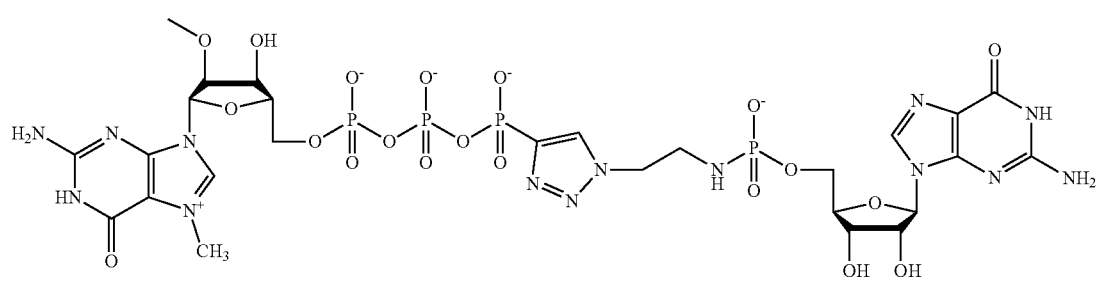
m₂^{7,2'-O}GppptC₂H₄NHpG -continued
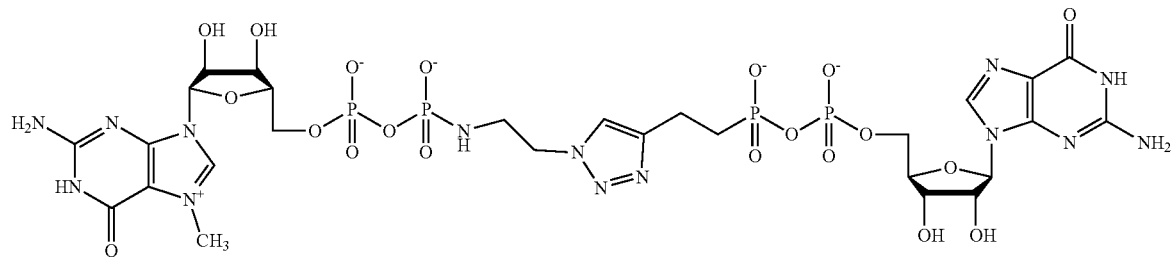
m⁷GppNHC₂H₄tC₂H₄ppG
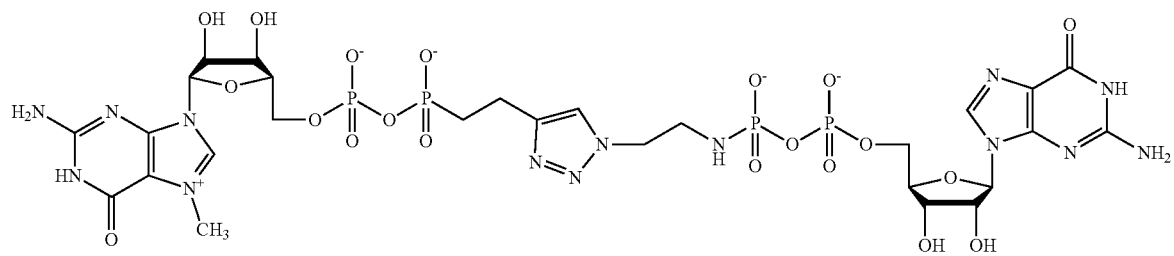
m⁷GppC₂H₄tC₂H₄NHppG
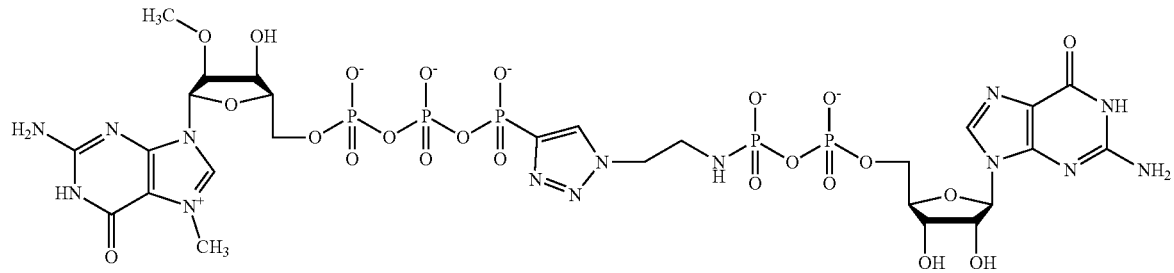
m₂^{7,2'-O}GppptC₂H₄NHppG
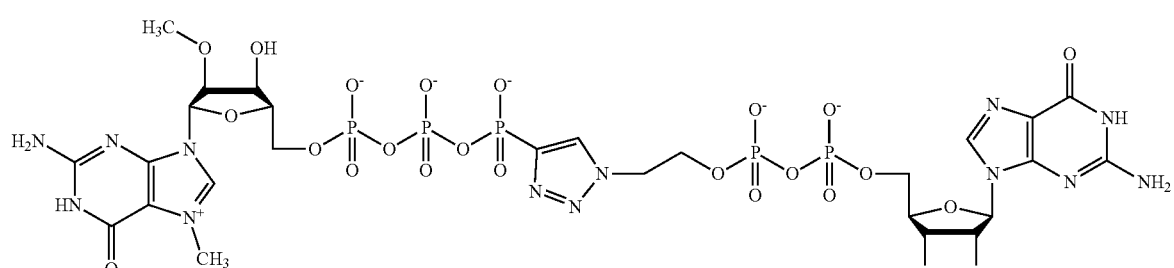
m₂^{7,2'-O}GppptC₂H₄OppG
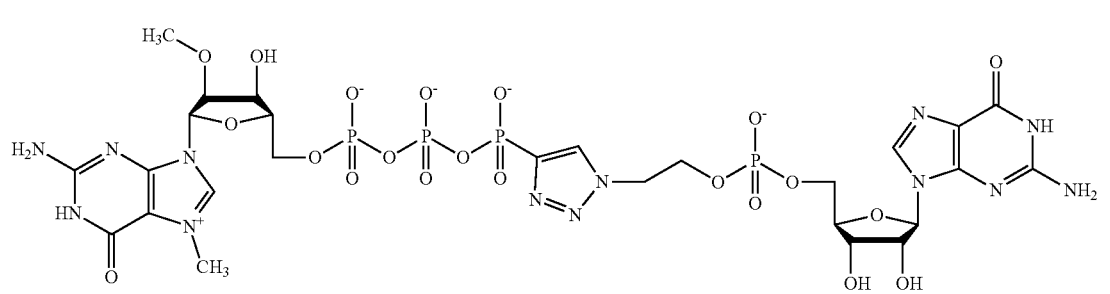
m₂^{7,2'-O}GppptC₂H₄OpG

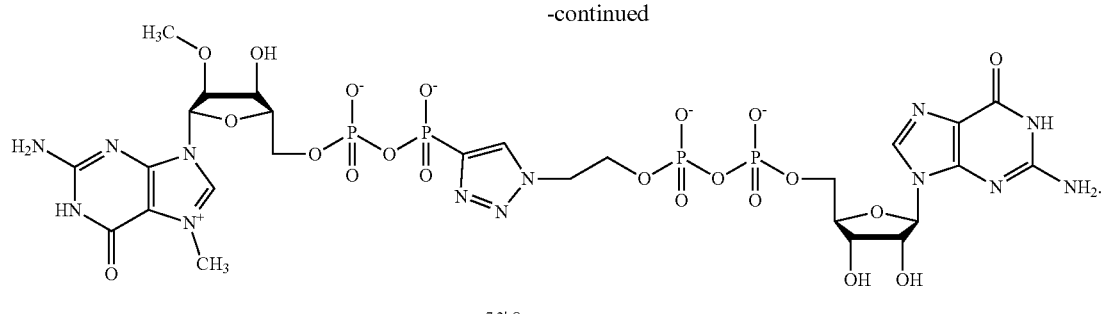

$m_2^{7,2'-O}GpptC_2H_4OppG$

5. A composition comprising at least one compound as defined in claim 1 or at least one stereoisomer or salt thereof and a suitable carrier or diluent.

6. An RNA molecule whose 5' end incorporates the compound as defined in claim 1.

7. A method of synthesizing, in vitro or in vivo, the RNA molecule whose 5' end incorporates the compound as defined in claim 1, said method comprising reacting ATP, CTP, UTP, and GTP, the compound of claim 1, and a polynucleotide template in the presence of RNA polymerase, in conditions enabling transcription by the RNA polymerase of the polynucleotide template into an RNA copy; whereby some of the RNA copies will incorporate the compound of any of claim 1 to make the RNA molecule.

8. A method of synthesizing a protein or peptide in vitro, said method comprising translating the RNA molecule as defined in claim 6 in a cell-free protein synthesis system, wherein the RNA molecule comprises an open reading frame, in conditions enabling translation of the open reading frame of the RNA molecule into the protein or peptide encoded by the open reading frame.

9. A method of synthesizing a protein or peptide in vivo or in cultured cells, said method comprising translating the RNA molecule as defined in claim 6 in vivo or in cultured cells, wherein the RNA molecule comprises an open reading frame, under conditions enabling translation of the open reading frame of the RNA molecule into the protein or peptide encoded by the said open reading frame.

\* \* \* \* \*